(12) United States Patent
Salahieh et al.

(10) Patent No.: US 10,098,694 B2
(45) Date of Patent: Oct. 16, 2018

(54) TISSUE ABLATION AND MONITORING THEREOF

(71) Applicant: APAMA MEDICAL, INC., Campbell, CA (US)

(72) Inventors: Amr Salahieh, Saratoga, CA (US); John P. Claude, Redwood City, CA (US); Tom Saul, Moss Beach, CA (US)

(73) Assignee: Apama Medical, Inc., Campbell, CA (US)

( * ) Notice: Subject to any disclaimer, the term of this patent is extended or adjusted under 35 U.S.C. 154(b) by 466 days.

(21) Appl. No.: 14/749,507

(22) Filed: Jun. 24, 2015

(65) Prior Publication Data

US 2016/0051321 A1 Feb. 25, 2016

Related U.S. Application Data

(63) Continuation-in-part of application No. 14/248,288, filed on Apr. 8, 2014, now Pat. No. 9,717,557.
(Continued)

(51) Int. Cl.
*A61B 18/14* (2006.01)
*A61B 8/12* (2006.01)
(Continued)

(52) U.S. Cl.
CPC ...... *A61B 18/1492* (2013.01); *A61B 1/00082* (2013.01); *A61B 1/00096* (2013.01);
(Continued)

(58) Field of Classification Search
CPC ........ A61B 18/1492; A61B 2018/1467; A61B 2018/0022; A61B 2018/1465;
(Continued)

(56) References Cited

U.S. PATENT DOCUMENTS

| 4,448,188 A | 5/1984 | Loeb |
| 4,547,193 A | 10/1985 | Rydell |

(Continued)

FOREIGN PATENT DOCUMENTS

| CN | 1085416 A | 4/1994 |
| CN | 1781161 A | 5/2006 |

(Continued)

OTHER PUBLICATIONS

Salahieh et al.; U.S. Appl. No. 15/375,027 entitled "Steerable medical devices, systems, and methods of use," filed Dec. 9, 2017.
(Continued)

*Primary Examiner* — Thomas Giuliani
(74) *Attorney, Agent, or Firm* — Faegre Baker Daniels LLP

(57) ABSTRACT

An ablation catheter includes an elongate shaft and an inflatable ablation member. The inflatable ablation member includes a flexible circuit with a conductor in electrical communication with an ablation electrode. The flexible circuit is disposed outside of and carried by an outer surface of an inflatable balloon. The inflatable ablation member includes an ultrasound monitoring member configured for use in monitoring at least one aspect of tissue ablation with the ablation electrode.

9 Claims, 33 Drawing Sheets

Related U.S. Application Data

(60) Provisional application No. 61/809,629, filed on Apr. 8, 2013, provisional application No. 61/809,646, filed on Apr. 8, 2013, provisional application No. 61/895,880, filed on Oct. 25, 2013, provisional application No. 61/809,636, filed on Apr. 8, 2013, provisional application No. 61/864,335, filed on Aug. 9, 2013, provisional application No. 61/829,985, filed on May 31, 2013, provisional application No. 61/820,992, filed on May 8, 2013, provisional application No. 61/821,001, filed on May 8, 2013, provisional application No. 61/821,014, filed on May 8, 2013, provisional application No. 61/934,640, filed on Jan. 31, 2014, provisional application No. 61/939,185, filed on Feb. 12, 2014, provisional application No. 61/934,647, filed on Jan. 31, 2014, provisional application No. 61/945,005, filed on Feb. 26, 2014, provisional application No. 61/947,950, filed on Mar. 4, 2014, provisional application No. 62/043,357, filed on Aug. 28, 2014, provisional application No. 62/025,378, filed on Jul. 16, 2014, provisional application No. 62/127,651, filed on Mar. 3, 2015, provisional application No. 62/142,398, filed on Apr. 2, 2015, provisional application No. 62/150,207, filed on Apr. 20, 2015, provisional application No. 62/016,585, filed on Jun. 24, 2014, provisional application No. 62/149,438, filed on Apr. 17, 2015, provisional application No. 62/154,978, filed on Apr. 30, 2015.

(51) Int. Cl.

| | | |
|---|---|---|
| *A61B 8/00* | (2006.01) | |
| *A61B 1/00* | (2006.01) | |
| *A61B 1/05* | (2006.01) | |
| *A61B 1/06* | (2006.01) | |
| *A61B 1/313* | (2006.01) | |
| *A61M 25/10* | (2013.01) | |
| *A61B 18/00* | (2006.01) | |
| *A61B 5/00* | (2006.01) | |
| *A61N 1/05* | (2006.01) | |
| *A61B 5/01* | (2006.01) | |
| *A61B 5/053* | (2006.01) | |
| *A61B 18/12* | (2006.01) | |
| *A61B 18/18* | (2006.01) | |
| *A61M 25/01* | (2006.01) | |
| *A61M 25/04* | (2006.01) | |
| *A61B 17/00* | (2006.01) | |
| *A61B 17/22* | (2006.01) | |
| *A61M 25/06* | (2006.01) | |
| *A61B 90/00* | (2016.01) | |
| *A61B 90/30* | (2016.01) | |

(52) U.S. Cl.
CPC ............ *A61B 1/05* (2013.01); *A61B 1/0676* (2013.01); *A61B 1/313* (2013.01); *A61B 8/12* (2013.01); *A61B 8/445* (2013.01); *A61B 8/4494* (2013.01); *A61M 25/10* (2013.01); *A61M 25/1011* (2013.01); *A61B 5/01* (2013.01); *A61B 5/0538* (2013.01); *A61B 5/6853* (2013.01); *A61B 5/6858* (2013.01); *A61B 18/1206* (2013.01); *A61B 18/1815* (2013.01); *A61B 90/30* (2016.02); *A61B 90/361* (2016.02); *A61B 90/37* (2016.02); *A61B 2017/003* (2013.01); *A61B 2017/0011* (2013.01); *A61B 2017/00106* (2013.01); *A61B 2017/00867* (2013.01); *A61B 2017/22038* (2013.01); *A61B 2018/00011* (2013.01); *A61B 2018/0016* (2013.01); *A61B 2018/0022* (2013.01); *A61B 2018/00023* (2013.01); *A61B 2018/00029* (2013.01); *A61B 2018/00083* (2013.01); *A61B 2018/0088* (2013.01); *A61B 2018/00214* (2013.01); *A61B 2018/00232* (2013.01); *A61B 2018/00238* (2013.01); *A61B 2018/00267* (2013.01); *A61B 2018/00285* (2013.01); *A61B 2018/00291* (2013.01); *A61B 2018/00351* (2013.01); *A61B 2018/00357* (2013.01); *A61B 2018/00375* (2013.01); *A61B 2018/00577* (2013.01); *A61B 2018/00613* (2013.01); *A61B 2018/00642* (2013.01); *A61B 2018/00702* (2013.01); *A61B 2018/00744* (2013.01); *A61B 2018/00791* (2013.01); *A61B 2018/00797* (2013.01); *A61B 2018/00815* (2013.01); *A61B 2018/00839* (2013.01); *A61B 2018/00875* (2013.01); *A61B 2018/00898* (2013.01); *A61B 2018/00982* (2013.01); *A61B 2018/124* (2013.01); *A61B 2018/1465* (2013.01); *A61B 2090/0454* (2016.02); *A61B 2090/064* (2016.02); *A61B 2090/065* (2016.02); *A61B 2090/309* (2016.02); *A61B 2090/364* (2016.02); *A61B 2090/3614* (2016.02); *A61B 2090/371* (2016.02); *A61B 2090/373* (2016.02); *A61B 2090/3966* (2016.02); *A61B 2217/007* (2013.01); *A61B 2218/002* (2013.01); *A61B 2562/125* (2013.01); *A61B 2562/164* (2013.01); *A61M 25/0108* (2013.01); *A61M 25/0133* (2013.01); *A61M 25/0147* (2013.01); *A61M 25/04* (2013.01); *A61M 2025/0681* (2013.01); *A61N 1/05* (2013.01); *C08L 2201/12* (2013.01)

(58) Field of Classification Search
CPC ........... A61B 2018/00982; A61B 2018/00011; A61B 2018/00839; A61B 2018/00023; A61B 2018/00636; A61B 2018/0016; A61B 2018/00285; A61B 2018/00357; A61B 8/12; A61B 8/445; A61B 8/4494; A61B 1/05; A61B 1/00096; A61B 5/6853; A61B 2017/0011; A61B 2017/00106; A61M 25/10
USPC ........ 606/41, 42, 47; 607/99, 101, 105, 116, 607/122
See application file for complete search history.

(56) References Cited

U.S. PATENT DOCUMENTS

| | | |
|---|---|---|
| 4,602,281 A | 7/1986 | Nagasaki et al. |
| 4,611,888 A | 9/1986 | Prenovitz et al. |
| 4,633,879 A | 1/1987 | Ong |
| 4,634,432 A | 1/1987 | Kocak |
| 4,638,207 A | 1/1987 | Radice |
| 4,646,721 A | 3/1987 | Arakawa |
| 4,692,139 A | 9/1987 | Stiles |
| 4,726,382 A | 2/1988 | Boehmer et al. |
| 4,739,766 A | 4/1988 | Riederer |
| 4,784,133 A | 11/1988 | Mackin |
| 4,809,680 A | 3/1989 | Yabe |
| 4,827,907 A | 5/1989 | Tashiro |
| 4,832,003 A | 5/1989 | Yabe |
| 4,843,275 A | 6/1989 | Radice |
| 4,890,623 A | 1/1990 | Cook et al. |
| 4,961,738 A | 10/1990 | Mackin |
| 4,968,306 A | 11/1990 | Huss et al. |
| 5,010,895 A | 4/1991 | Maurer et al. |
| 5,029,574 A | 7/1991 | Shimamura et al. |

(56) References Cited

U.S. PATENT DOCUMENTS

| | | | |
|---|---|---|---|
| 5,041,089 | A | 8/1991 | Mueller et al. |
| 5,069,674 | A | 12/1991 | Fearnot et al. |
| 5,090,959 | A | 2/1992 | Samson et al. |
| 5,109,861 | A | 5/1992 | Walinsky et al. |
| 5,115,472 | A | 5/1992 | Park et al. |
| 5,135,001 | A * | 8/1992 | Sinofsky ................ A61B 8/12 600/459 |
| 5,180,376 | A | 1/1993 | Fischell |
| 5,187,572 | A | 2/1993 | Nakamura et al. |
| 5,209,741 | A | 5/1993 | Spaeth |
| 5,213,576 | A | 5/1993 | Abiuso et al. |
| 5,228,442 | A | 7/1993 | Imran |
| 5,233,416 | A | 8/1993 | Inoue |
| 5,301,090 | A | 4/1994 | Hed |
| 5,306,250 | A | 4/1994 | March et al. |
| 5,309,910 | A | 5/1994 | Edwards et al. |
| 5,311,866 | A | 5/1994 | Kagan et al. |
| 5,325,847 | A | 7/1994 | Matsuno |
| 5,343,860 | A | 9/1994 | Metzger et al. |
| 5,377,682 | A | 1/1995 | Ueno et al. |
| 5,385,148 | A | 1/1995 | Lash et al. |
| 5,391,200 | A | 2/1995 | KenKnight et al. |
| 5,409,000 | A | 4/1995 | Imran |
| 5,411,016 | A | 5/1995 | Kume et al. |
| 5,430,475 | A | 7/1995 | Goto et al. |
| 5,443,470 | A | 8/1995 | Stern et al. |
| 5,494,483 | A | 2/1996 | Adair |
| 5,505,730 | A | 4/1996 | Edwards |
| 5,515,848 | A | 5/1996 | Corbett et al. |
| 5,524,338 | A | 6/1996 | Martyniuk et al. |
| 5,540,679 | A | 7/1996 | Fram et al. |
| 5,558,672 | A | 9/1996 | Edwards et al. |
| 5,562,720 | A | 10/1996 | Stern et al. |
| 5,569,241 | A | 10/1996 | Edwards |
| 5,571,086 | A | 11/1996 | Kaplan et al. |
| 5,571,088 | A | 11/1996 | Lennox et al. |
| 5,573,520 | A | 11/1996 | Schwartz et al. |
| 5,575,772 | A | 11/1996 | Lennox |
| 5,575,788 | A | 11/1996 | Baker et al. |
| 5,594,497 | A | 1/1997 | Ahern et al. |
| 5,607,436 | A | 3/1997 | Pratt et al. |
| 5,609,574 | A | 3/1997 | Kaplan et al. |
| 5,609,606 | A | 3/1997 | O'Boyle |
| 5,611,807 | A | 3/1997 | O'Boyle |
| 5,626,564 | A | 5/1997 | Zhan et al. |
| 5,630,837 | A | 5/1997 | Crowley |
| 5,681,308 | A | 10/1997 | Edwards et al. |
| 5,715,825 | A | 2/1998 | Crowley |
| 5,718,701 | A | 2/1998 | Shai et al. |
| 5,722,403 | A | 3/1998 | McGee et al. |
| 5,735,846 | A | 4/1998 | Panescu et al. |
| 5,769,846 | A | 6/1998 | Edwards et al. |
| 5,769,880 | A | 6/1998 | Truckai et al. |
| 5,779,698 | A | 7/1998 | Clayman et al. |
| 5,795,325 | A | 8/1998 | Valley et al. |
| 5,797,837 | A | 8/1998 | Minami |
| 5,800,408 | A | 9/1998 | Strauss et al. |
| 5,827,273 | A | 10/1998 | Edwards |
| 5,830,213 | A | 11/1998 | Panescu et al. |
| 5,836,874 | A | 11/1998 | Swanson et al. |
| 5,846,196 | A | 12/1998 | Siekmeyer et al. |
| 5,846,238 | A | 12/1998 | Jackson et al. |
| 5,846,239 | A | 12/1998 | Swanson et al. |
| 5,853,411 | A | 12/1998 | Whayne et al. |
| 5,860,974 | A | 1/1999 | Abele |
| 5,871,483 | A | 2/1999 | Jackson et al. |
| 5,879,348 | A | 3/1999 | Owens et al. |
| 5,881,727 | A | 3/1999 | Edwards |
| 5,888,577 | A | 3/1999 | Griffin, III et al. |
| 5,904,651 | A | 5/1999 | Swanson et al. |
| 5,916,213 | A | 6/1999 | Haissaguerre et al. |
| 5,935,075 | A | 8/1999 | Casscells et al. |
| 5,938,660 | A | 8/1999 | Swartz et al. |
| 5,940,126 | A | 8/1999 | Kimura |
| 5,957,950 | A | 9/1999 | Mockros et al. |
| 5,961,513 | A | 10/1999 | Swanson et al. |
| 5,967,986 | A | 10/1999 | Cimochowski et al. |
| 5,984,860 | A | 11/1999 | Shan |
| 5,991,650 | A | 11/1999 | Swanson et al. |
| 5,997,571 | A | 12/1999 | Farr et al. |
| 6,004,269 | A | 12/1999 | Crowley et al. |
| 6,006,119 | A | 12/1999 | Soller et al. |
| 6,012,457 | A | 1/2000 | Lesh |
| 6,024,740 | A | 2/2000 | Lesh et al. |
| 6,052,607 | A | 4/2000 | Edwards et al. |
| 6,071,302 | A | 6/2000 | Sinofsky et al. |
| 6,102,905 | A | 8/2000 | Baxter et al. |
| 6,117,101 | A | 9/2000 | Diederich et al. |
| 6,123,718 | A | 9/2000 | Tu et al. |
| 6,124,883 | A | 9/2000 | Suzuki et al. |
| 6,134,463 | A | 10/2000 | Wittkampf et al. |
| 6,142,993 | A | 11/2000 | Whayne et al. |
| 6,159,203 | A | 12/2000 | Sinofsky |
| 6,163,726 | A | 12/2000 | Wolf |
| 6,164,283 | A | 12/2000 | Lesh |
| 6,168,591 | B1 | 1/2001 | Sinofsky |
| 6,178,346 | B1 | 1/2001 | Amundson et al. |
| 6,205,361 | B1 | 3/2001 | Kuzma et al. |
| 6,206,912 | B1 | 3/2001 | Goldsteen et al. |
| 6,215,231 | B1 | 4/2001 | Newnham et al. |
| 6,231,516 | B1 | 5/2001 | Keilman et al. |
| 6,233,491 | B1 | 5/2001 | Kordis et al. |
| 6,270,492 | B1 | 8/2001 | Sinofsky |
| 6,292,689 | B1 | 9/2001 | Wallace et al. |
| 6,315,712 | B1 | 11/2001 | Rovegno |
| 6,375,654 | B1 | 4/2002 | McIntyre |
| 6,384,915 | B1 | 5/2002 | Everett et al. |
| 6,391,024 | B1 | 5/2002 | Sun et al. |
| 6,402,746 | B1 | 6/2002 | Whayne et al. |
| 6,416,463 | B1 | 7/2002 | Tsuzuki et al. |
| 6,425,877 | B1 | 7/2002 | Edwards |
| 6,460,545 | B2 | 10/2002 | Kordis |
| 6,485,414 | B1 | 11/2002 | Neuberger |
| 6,500,174 | B1 | 12/2002 | Maguire et al. |
| 6,511,478 | B1 | 1/2003 | Burnside et al. |
| 6,514,249 | B1 | 2/2003 | Maguire et al. |
| 6,517,534 | B1 | 2/2003 | McGovern et al. |
| 6,527,769 | B2 | 3/2003 | Langberg et al. |
| 6,558,375 | B1 | 5/2003 | Sinofsky et al. |
| 6,558,378 | B2 | 5/2003 | Sherman et al. |
| 6,572,609 | B1 | 6/2003 | Farr et al. |
| 6,572,612 | B2 | 6/2003 | Stewart et al. |
| 6,579,285 | B2 | 6/2003 | Sinofsky |
| 6,595,989 | B1 | 7/2003 | Schaer |
| 6,599,288 | B2 | 7/2003 | Maguire et al. |
| 6,605,055 | B1 | 8/2003 | Sinofsky et al. |
| 6,605,084 | B2 | 8/2003 | Acker et al. |
| 6,607,502 | B1 | 8/2003 | Maguire et al. |
| 6,635,027 | B1 | 10/2003 | Cragg et al. |
| 6,635,054 | B2 | 10/2003 | Fjield et al. |
| 6,641,553 | B1 | 11/2003 | Chee et al. |
| 6,652,515 | B1 | 11/2003 | Maguire et al. |
| 6,659,940 | B2 | 12/2003 | Adler |
| 6,659,953 | B1 | 12/2003 | Smanaweera et al. |
| 6,660,002 | B1 | 12/2003 | Edwards et al. |
| 6,676,656 | B2 | 1/2004 | Sinofsky |
| 6,692,430 | B2 | 2/2004 | Adler |
| 6,692,431 | B2 | 2/2004 | Kazakevich |
| 6,692,455 | B2 | 2/2004 | Goode et al. |
| 6,692,461 | B2 | 2/2004 | Wantink |
| 6,692,462 | B2 | 2/2004 | Mackenzie et al. |
| 6,692,463 | B1 | 2/2004 | Marteau et al. |
| 6,692,464 | B2 | 2/2004 | Graf |
| 6,692,490 | B1 | 2/2004 | Edwards |
| 6,702,782 | B2 | 3/2004 | Miller et al. |
| 6,736,811 | B2 | 5/2004 | Panescu et al. |
| 6,743,226 | B2 | 6/2004 | Cosman et al. |
| 6,752,805 | B2 | 6/2004 | Maguire et al. |
| 6,771,996 | B2 | 8/2004 | Bowe et al. |
| 6,780,183 | B2 | 8/2004 | Jimenez, Jr. et al. |
| 6,808,524 | B2 | 10/2004 | Lopath et al. |
| 6,814,730 | B2 | 11/2004 | Li |
| 6,869,431 | B2 | 3/2005 | Maguire et al. |
| 6,872,183 | B2 | 3/2005 | Sampson et al. |

(56) References Cited

U.S. PATENT DOCUMENTS

| | | |
|---|---|---|
| 6,872,206 B2 | 3/2005 | Edwards et al. |
| 6,887,235 B2 | 5/2005 | O'Connor et al. |
| 6,911,027 B1 | 6/2005 | Edwards et al. |
| 6,932,809 B2 | 8/2005 | Sinofsky |
| 6,937,899 B2 | 8/2005 | Sheldon et al. |
| 6,942,657 B2 | 9/2005 | Sinofsky et al. |
| 6,949,072 B2 | 9/2005 | Furnish et al. |
| 6,955,173 B2 | 10/2005 | Lesh |
| 6,976,956 B2 | 12/2005 | Takahashi et al. |
| 6,978,174 B2 | 12/2005 | Gelfand et al. |
| 7,004,923 B2 | 2/2006 | Deniega et al. |
| 7,030,904 B2 | 4/2006 | Adair et al. |
| 7,048,733 B2 | 5/2006 | Hartley et al. |
| 7,115,122 B1 | 10/2006 | Swanson et al. |
| 7,137,395 B2 | 11/2006 | Fried et al. |
| 7,150,745 B2 | 12/2006 | Stem et al. |
| 7,162,303 B2 | 1/2007 | Levin et al. |
| 7,166,075 B2 | 1/2007 | Varghese et al. |
| 7,169,140 B1 | 1/2007 | Kume |
| 7,207,984 B2 | 4/2007 | Farr et al. |
| 7,226,448 B2 | 6/2007 | Bertolero et al. |
| 7,232,437 B2 | 6/2007 | Berman et al. |
| 7,238,179 B2 | 7/2007 | Brucker et al. |
| 7,238,180 B2 | 7/2007 | Mester et al. |
| 7,267,674 B2 | 9/2007 | Brucker et al. |
| 7,285,116 B2 | 10/2007 | de la Rama et al. |
| 7,286,866 B2 | 10/2007 | Okerlund et al. |
| 7,291,146 B2 | 11/2007 | Steinke et al. |
| 7,293,562 B2 | 11/2007 | Malecki et al. |
| 7,300,397 B2 | 11/2007 | Adler et al. |
| 7,310,150 B2 | 12/2007 | Guillermo et al. |
| 7,320,677 B2 | 1/2008 | Brouillette |
| 7,344,533 B2 | 3/2008 | Pearson et al. |
| 7,346,381 B2 | 3/2008 | Okerlund et al. |
| 7,357,796 B2 | 4/2008 | Farr et al. |
| 7,365,859 B2 | 4/2008 | Yun et al. |
| 7,366,376 B2 | 4/2008 | Shishkov et al. |
| 7,367,975 B2 | 5/2008 | Malecki et al. |
| 7,371,231 B2 | 5/2008 | Rioux et al. |
| 7,382,949 B2 | 6/2008 | Bouma et al. |
| 7,396,355 B2 | 7/2008 | Goldman et al. |
| 7,406,970 B2 | 8/2008 | Zikorus et al. |
| 7,413,568 B2 | 8/2008 | Swanson et al. |
| 7,418,169 B2 | 8/2008 | Tearney et al. |
| 7,427,265 B1 | 9/2008 | Keilman et al. |
| 7,429,260 B2 | 9/2008 | Underwood et al. |
| 7,429,261 B2 | 9/2008 | Kunis et al. |
| 7,445,618 B2 | 11/2008 | Eggers et al. |
| 7,447,408 B2 | 11/2008 | Bouma et al. |
| 7,452,358 B2 | 11/2008 | Stern et al. |
| 7,468,062 B2 | 12/2008 | Oral et al. |
| 7,473,251 B2 | 1/2009 | Knowlton et al. |
| 7,481,808 B2 | 1/2009 | Koyfman et al. |
| 7,481,809 B2 | 1/2009 | Stern et al. |
| 7,489,969 B2 | 2/2009 | Knudson et al. |
| 7,507,236 B2 | 3/2009 | Eggers et al. |
| 7,510,555 B2 | 3/2009 | Kanzius |
| 7,517,346 B2 | 4/2009 | Sloan et al. |
| 7,519,096 B2 | 4/2009 | Bouma et al. |
| 7,529,393 B2 | 5/2009 | Peszynski et al. |
| 7,534,204 B2 | 5/2009 | Starksen et al. |
| 7,538,859 B2 | 5/2009 | Tearney et al. |
| 7,585,273 B2 | 9/2009 | Adler et al. |
| 7,588,535 B2 | 9/2009 | Adler et al. |
| 7,617,005 B2 | 11/2009 | Demarais et al. |
| 7,620,451 B2 | 11/2009 | Demarais et al. |
| 7,653,438 B2 | 1/2010 | Deem et al. |
| 7,669,309 B2 | 3/2010 | Johnson et al. |
| 7,683,323 B2 | 3/2010 | Kymissis |
| 7,756,583 B2 | 7/2010 | Demarais et al. |
| 7,758,499 B2 | 7/2010 | Adler |
| 7,853,333 B2 | 12/2010 | Demarais |
| 7,879,029 B2 | 2/2011 | Jimenez |
| 7,928,113 B2 | 4/2011 | Neamati et al. |
| 7,935,108 B2 | 5/2011 | Baxter et al. |
| 7,937,143 B2 | 5/2011 | Demarais et al. |
| 8,007,440 B2 | 8/2011 | Magnin et al. |
| 8,025,661 B2 | 9/2011 | Arnold et al. |
| 8,078,266 B2 | 12/2011 | Saadat et al. |
| 8,167,805 B2 | 5/2012 | Emery et al. |
| 8,172,747 B2 | 5/2012 | Wallace et al. |
| 8,194,121 B2 | 6/2012 | Blumzvig et al. |
| 8,295,902 B2 | 10/2012 | Salahieh et al. |
| 8,323,241 B2 | 12/2012 | Salahieh et al. |
| 8,333,012 B2 | 12/2012 | Rothe et al. |
| 8,337,492 B2 | 12/2012 | Kunis et al. |
| 8,361,041 B2 | 1/2013 | Fang et al. |
| 8,369,921 B2 | 2/2013 | Tegg et al. |
| 8,417,321 B2 | 4/2013 | Saadat et al. |
| 8,419,613 B2 | 4/2013 | Saadat et al. |
| 8,465,421 B2 | 6/2013 | Finkman et al. |
| 8,479,585 B2 | 7/2013 | Shaw-Klein |
| 8,540,704 B2 | 9/2013 | Melsky et al. |
| 8,560,086 B2 | 10/2013 | Just et al. |
| 8,617,150 B2 | 12/2013 | Tsoref et al. |
| 8,702,682 B2 | 4/2014 | Atanasoska et al. |
| 8,708,953 B2 | 4/2014 | Salahieh et al. |
| 8,728,073 B2 | 5/2014 | McDaniel |
| 8,777,857 B2 | 7/2014 | Sliwa et al. |
| 8,805,466 B2 | 8/2014 | Salahieh et al. |
| 8,808,281 B2 | 8/2014 | Emmons et al. |
| 8,840,601 B2 | 9/2014 | Salahieh et al. |
| 8,894,643 B2 | 11/2014 | Watson et al. |
| 8,920,369 B2 | 12/2014 | Salahieh et al. |
| 8,939,970 B2 | 1/2015 | Stone et al. |
| 8,968,591 B2 | 3/2015 | Nishikubo et al. |
| 8,981,625 B2 | 3/2015 | Nishikubo et al. |
| 9,037,259 B2 | 5/2015 | Mathur |
| 9,174,050 B2 | 11/2015 | Mathur et al. |
| 9,445,862 B2 | 9/2016 | Brewster et al. |
| 9,717,557 B2 | 8/2017 | Salahieh et al. |
| 2002/0002384 A1 | 1/2002 | Gilson et al. |
| 2002/0068934 A1 | 6/2002 | Edwards et al. |
| 2002/0095147 A1 | 7/2002 | Shadduck |
| 2002/0111548 A1 | 8/2002 | Swanson et al. |
| 2002/0154215 A1 | 10/2002 | Schechterman et al. |
| 2002/0165535 A1 | 11/2002 | Lesh et al. |
| 2002/0183623 A1 | 12/2002 | Tang et al. |
| 2003/0050637 A1 | 3/2003 | Maguire et al. |
| 2003/0065371 A1 | 4/2003 | Satake |
| 2003/0097121 A1 | 5/2003 | Jolly et al. |
| 2003/0097129 A1 | 5/2003 | Davison et al. |
| 2003/0135101 A1 | 7/2003 | Webler |
| 2003/0233099 A1 | 12/2003 | Danaek et al. |
| 2003/0236443 A1 | 12/2003 | Cespedes et al. |
| 2004/0054363 A1 | 3/2004 | Vaska et al. |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0167503 A1 | 8/2004 | Sinofsky |
| 2004/0243118 A1 | 12/2004 | Ayers et al. |
| 2005/0004440 A1 | 1/2005 | Vanney |
| 2005/0065504 A1 | 3/2005 | Melsky et al. |
| 2005/0171527 A1 | 8/2005 | Bhola |
| 2005/0203597 A1 | 9/2005 | Yamazaki et al. |
| 2005/0222558 A1 | 10/2005 | Baxter et al. |
| 2005/0234436 A1 | 10/2005 | Baxter et al. |
| 2005/0234437 A1 | 10/2005 | Baxter et al. |
| 2005/0245892 A1 | 11/2005 | Elkins et al. |
| 2006/0041277 A1 | 2/2006 | Deem et al. |
| 2006/0089632 A1 | 4/2006 | Barthe et al. |
| 2006/0100618 A1 | 5/2006 | Chan et al. |
| 2006/0173300 A1 | 8/2006 | Oslund et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0247701 A1 | 11/2006 | Zacouto |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0032727 A1 | 2/2007 | Omata |
| 2007/0073135 A1 | 3/2007 | Lee et al. |
| 2007/0078507 A1 | 4/2007 | Zacouto |

(56) References Cited

U.S. PATENT DOCUMENTS

| | | |
|---|---|---|
| 2007/0112422 A1 | 5/2007 | Dehdashtian |
| 2007/0118094 A1 | 5/2007 | Bingham et al. |
| 2007/0129720 A1 | 6/2007 | Demarais et al. |
| 2007/0129760 A1 | 6/2007 | Demarais et al. |
| 2007/0135875 A1 | 6/2007 | Demarais et al. |
| 2007/0213616 A1 | 9/2007 | Anderson et al. |
| 2007/0213671 A1 | 9/2007 | Hiatt |
| 2007/0219451 A1 | 9/2007 | Kula et al. |
| 2007/0225634 A1 | 9/2007 | Ferren et al. |
| 2007/0233185 A1 | 10/2007 | Anderson et al. |
| 2007/0244501 A1 | 10/2007 | Horn et al. |
| 2007/0255097 A1 | 11/2007 | Jung et al. |
| 2007/0270686 A1 | 11/2007 | Ritter et al. |
| 2007/0287994 A1 | 12/2007 | Patel |
| 2008/0004652 A1 | 1/2008 | Abboud et al. |
| 2008/0058590 A1 | 3/2008 | Saadat et al. |
| 2008/0058591 A1 | 3/2008 | Saadat et al. |
| 2008/0058836 A1* | 3/2008 | Moll ............... A61B 1/00082 606/130 |
| 2008/0071173 A1 | 3/2008 | Aldrich |
| 2008/0108867 A1 | 5/2008 | Zhou |
| 2008/0125772 A1 | 5/2008 | Stone et al. |
| 2008/0188912 A1 | 8/2008 | Stone et al. |
| 2008/0205481 A1 | 8/2008 | Faries, Jr. et al. |
| 2008/0262489 A1 | 10/2008 | Steinke |
| 2008/0275300 A1 | 11/2008 | Rothe et al. |
| 2008/0275445 A1 | 11/2008 | Kelly et al. |
| 2008/0281293 A1 | 11/2008 | Peh et al. |
| 2008/0281312 A1 | 11/2008 | Werneth et al. |
| 2008/0281322 A1 | 11/2008 | Sherman et al. |
| 2008/0296152 A1 | 12/2008 | Voss |
| 2009/0024195 A1 | 1/2009 | Rezai et al. |
| 2009/0030276 A1 | 1/2009 | Saadat et al. |
| 2009/0030412 A1 | 1/2009 | Willis et al. |
| 2009/0046171 A1 | 2/2009 | Kogan et al. |
| 2009/0051763 A1 | 2/2009 | Adler et al. |
| 2009/0054786 A1 | 2/2009 | Beckermus |
| 2009/0054787 A1 | 2/2009 | Adler et al. |
| 2009/0054803 A1 | 2/2009 | Saadat et al. |
| 2009/0076498 A1 | 3/2009 | Saadat et al. |
| 2009/0125022 A1 | 5/2009 | Saadat et al. |
| 2009/0137893 A1 | 5/2009 | Seibel et al. |
| 2009/0203962 A1 | 8/2009 | Miller et al. |
| 2009/0227885 A1 | 9/2009 | Lowery et al. |
| 2009/0227999 A1 | 9/2009 | Willis et al. |
| 2009/0240249 A1 | 9/2009 | Chan et al. |
| 2009/0247933 A1 | 10/2009 | Maor et al. |
| 2009/0254142 A1 | 10/2009 | Edwards et al. |
| 2009/0275799 A1 | 11/2009 | Saadat et al. |
| 2009/0299354 A1 | 12/2009 | Melsky et al. |
| 2009/0312754 A1 | 12/2009 | Lenihan et al. |
| 2009/0318757 A1 | 12/2009 | Singh |
| 2009/0318759 A1 | 12/2009 | Jacobsen et al. |
| 2009/0326320 A1 | 12/2009 | Sinofsky et al. |
| 2009/0326321 A1 | 12/2009 | Jacobsen et al. |
| 2009/0326572 A1 | 12/2009 | Peh et al. |
| 2010/0016957 A1 | 1/2010 | Jager et al. |
| 2010/0087782 A1 | 4/2010 | Ghaffari et al. |
| 2010/0121142 A1 | 5/2010 | Ouyang et al. |
| 2010/0204561 A1 | 8/2010 | Saadat et al. |
| 2010/0238279 A1 | 9/2010 | Thoms et al. |
| 2011/0034790 A1 | 2/2011 | Mourlas et al. |
| 2011/0034912 A1 | 2/2011 | de Graff et al. |
| 2011/0040172 A1* | 2/2011 | Carpentier ........... A61B 5/0068 600/411 |
| 2011/0046600 A1 | 2/2011 | Crank |
| 2011/0077579 A1 | 3/2011 | Harrison et al. |
| 2011/0082449 A1 | 4/2011 | Melsky et al. |
| 2011/0082450 A1 | 4/2011 | Melsky et al. |
| 2011/0082451 A1 | 4/2011 | Melsky |
| 2011/0082452 A1 | 4/2011 | Melsky et al. |
| 2011/0152352 A1 | 6/2011 | Hata et al. |
| 2011/0160514 A1 | 6/2011 | Long et al. |
| 2011/0160584 A1 | 6/2011 | Paul et al. |
| 2011/0201973 A1 | 8/2011 | Stephens et al. |
| 2011/0257523 A1 | 10/2011 | Hastings et al. |
| 2011/0292258 A1 | 12/2011 | Adler et al. |
| 2011/0301418 A1 | 12/2011 | Gharib et al. |
| 2011/0319752 A1 | 12/2011 | Steinberg et al. |
| 2012/0004529 A1 | 1/2012 | Tolkowsky et al. |
| 2012/0004537 A1 | 1/2012 | Tolkowsky et al. |
| 2012/0116438 A1 | 5/2012 | Salahieh et al. |
| 2012/0130171 A1 | 5/2012 | Barak et al. |
| 2012/0165669 A1 | 6/2012 | Barley et al. |
| 2012/0302877 A1 | 11/2012 | Harks et al. |
| 2013/0079645 A1 | 3/2013 | Amirana et al. |
| 2013/0085493 A1* | 4/2013 | Bloom ............... A61B 18/1492 606/41 |
| 2013/0137920 A1 | 5/2013 | Schaeffer et al. |
| 2013/0138082 A1 | 5/2013 | Salahieh et al. |
| 2013/0172726 A9 | 7/2013 | Saadat et al. |
| 2013/0172883 A1 | 7/2013 | Lopes et al. |
| 2013/0178850 A1 | 7/2013 | Lopes et al. |
| 2013/0178851 A1 | 7/2013 | Lopes et al. |
| 2013/0204125 A1 | 8/2013 | Chang et al. |
| 2013/0204126 A1 | 8/2013 | Namati et al. |
| 2013/0231533 A1 | 9/2013 | Papademetriou et al. |
| 2013/0289350 A1 | 10/2013 | Lerner et al. |
| 2013/0304065 A1 | 11/2013 | Lopes et al. |
| 2013/0317497 A1 | 11/2013 | Edwards et al. |
| 2014/0031810 A1 | 1/2014 | Mahvi et al. |
| 2014/0058197 A1 | 2/2014 | Salahieh et al. |
| 2014/0107623 A1 | 4/2014 | Salahieh et al. |
| 2014/0121470 A1 | 5/2014 | Scharf et al. |
| 2014/0180273 A1 | 6/2014 | Nair |
| 2014/0213850 A1 | 7/2014 | Levy et al. |
| 2014/0243680 A1 | 8/2014 | Raleigh |
| 2014/0296643 A1 | 10/2014 | Levy et al. |
| 2014/0296866 A1 | 10/2014 | Salman et al. |
| 2014/0309495 A1 | 10/2014 | Kirma et al. |
| 2014/0316198 A1 | 10/2014 | Krivopisk et al. |
| 2014/0320617 A1 | 10/2014 | Parks et al. |
| 2014/0333743 A1 | 11/2014 | Gilreath et al. |
| 2014/0357956 A1* | 12/2014 | Salahieh ............... A61B 1/05 600/160 |
| 2014/0358140 A1 | 12/2014 | Emmons et al. |
| 2014/0364691 A1 | 12/2014 | Krivopisk et al. |
| 2014/0364692 A1 | 12/2014 | Salman et al. |
| 2014/0364694 A1 | 12/2014 | Avron et al. |
| 2014/0370072 A1 | 12/2014 | Hossainy et al. |
| 2015/0073341 A1 | 3/2015 | Salahieh et al. |
| 2015/0094656 A1 | 4/2015 | Salahieh et al. |
| 2015/0327753 A1 | 11/2015 | Amirana et al. |
| 2016/0000500 A1* | 1/2016 | Salahieh ............ A61B 18/1492 600/104 |
| 2016/0157954 A1 | 6/2016 | Sagan et al. |
| 2017/0042614 A1 | 2/2017 | Salahieh et al. |
| 2017/0042615 A1 | 2/2017 | Salahieh et al. |
| 2017/0143201 A1* | 5/2017 | Claude ................ A61B 1/3137 |

FOREIGN PATENT DOCUMENTS

| | | |
|---|---|---|
| CN | 101511292 A | 8/2009 |
| CN | 101888813 A | 11/2010 |
| DE | 4104092 A1 | 8/1991 |
| EP | 0322852 A1 | 7/1989 |
| EP | 0802768 A | 10/1997 |
| EP | 0637943 B1 | 4/1998 |
| EP | 623360 B1 | 3/1999 |
| EP | 0723467 B1 | 4/2002 |
| EP | 0693955 B1 | 1/2003 |
| EP | 1382366 A1 | 1/2004 |
| EP | 1463441 A2 | 10/2004 |
| EP | 1604613 A1 | 12/2005 |
| EP | 1991301 A2 | 11/2008 |
| EP | 2335757 A2 | 6/2011 |
| JP | H08-504333 A | 5/1996 |
| JP | 2000-504242 A | 4/2000 |
| JP | 2003510126 A | 3/2003 |
| JP | 2004237077 A | 8/2004 |
| JP | 2008142346 | 6/2006 |
| JP | 2007516010 | 6/2007 |
| JP | 2009507617 | 2/2009 |
| JP | 2009539575 | 11/2009 |

(56) References Cited

FOREIGN PATENT DOCUMENTS

| | | | |
|---|---|---|---|
| JP | 2010507404 A | 3/2010 | |
| JP | 2012525898 A | 10/2012 | |
| WO | WO87/05748 A1 | 9/1987 | |
| WO | WO95/05775 A1 | 3/1995 | |
| WO | WO98/31271 A2 | 7/1998 | |
| WO | WO 99/00060 A1 | 1/1999 | |
| WO | WO99/02096 A1 | 1/1999 | |
| WO | WO99/26530 A1 | 6/1999 | |
| WO | WO99/42176 A1 | 8/1999 | |
| WO | WO99/44519 A2 | 9/1999 | |
| WO | WO99/45855 A1 | 9/1999 | |
| WO | WO00/38580 A1 | 7/2000 | |
| WO | WO00/56237 A2 | 9/2000 | |
| WO | WO 00/66014 A1 | 11/2000 | |
| WO | WO00/67648 A1 | 11/2000 | |
| WO | WO00/67656 A1 | 11/2000 | |
| WO | WO01/08575 A2 | 2/2001 | |
| WO | WO01/08576 A2 | 2/2001 | |
| WO | WO01/13812 A1 | 3/2001 | |
| WO | WO01/68178 A1 | 9/2001 | |
| WO | WO01/72373 A2 | 10/2001 | |
| WO | WO01/87169 A1 | 11/2001 | |
| WO | WO01/87174 A1 | 11/2001 | |
| WO | WO01/95820 A1 | 12/2001 | |
| WO | WO02/40089 A2 | 5/2002 | |
| WO | WO03/013624 A2 | 2/2003 | |
| WO | WO05/32370 | 4/2005 | |
| WO | WO2005/065563 A1 | 7/2005 | |
| WO | WO2006/077573 A1 | 7/2006 | |
| WO | WO2007/001981 A2 | 1/2007 | |
| WO | WO2007/047993 A2 | 4/2007 | |
| WO | WO2007/059195 A1 | 5/2007 | |
| WO | WO2008/061152 A2 | 5/2008 | |
| WO | WO 2009/067695 A1 | 5/2009 | |
| WO | WO 2009/088678 A1 | 7/2009 | |
| WO | WO 2009/132137 A1 | 10/2009 | |
| WO | WO2009/151600 A2 | 12/2009 | |
| WO | WO 2009/155441 A2 | 12/2009 | |
| WO | 2011143468 A3 | 11/2011 | |
| WO | WO2011/153434 A2 | 12/2011 | |
| WO | WO2012/033837 A2 | 3/2012 | |
| WO | WO 2013/049601 A2 | 4/2013 | |
| WO | WO2013/098732 A1 | 7/2013 | |
| WO | WO2014/100259 A1 | 6/2014 | |

OTHER PUBLICATIONS

Hu et al.; In-vivo pan/tilt endoscope with integrated light source; Intelligent Robots and Systems; IROS 2007. IEEE/RSJ International Conference on; pp. 1284-1289; San Diego, CA, USA: Oct. 29-Nov. 2, 2007.

Tymecki et al; Strip thick-film silver ion-selective electrodes; Sensors and Actuators B; 96(3); pp. 482-488; Dec. 1, 2003.

Wippermann et al.; Low cost video endoscopes with simplified integration; In SPIE Photonics Europe; International Society for Optics and Phtonics; vol. 7716; pp. 77160M-1-77160M-9; Apr. 30, 2010.

Salahieh et al.; U.S. Appl. No. 14/850,820 entitled "Visualization inside an expandable medical device," filed Sep. 10, 2015.

Salahieh et al.; U.S. Appl. No. 15/375,027 entitled "Steerable medical devices, systems, and methods of use," filed Dec. 9, 2016.

Salahieh et al.; U.S. Appl. No. 15/452,413 entitled "Steerable delivery sheaths," filed Mar. 7, 2017.

Salahieh et al.; U.S. Appl. No. 13/830,624 entitled "Local Sympathectomy for PVD," filed Mar. 14, 2013.

Salahieh et al.; U.S. Appl. No. 61/622,495 entitled "Energy Delivery Device with Rapid Exchange Features," filed Apr. 10, 2012.

Salahieh et al.; U.S. Appl. No. 61/624,206 entitled "Energy delivery device and methods of use," filed Apr. 13, 2012.

Denham et al.; Ultrasonic resonant modes of piezoelectric balloons under internal pressure; J. Acoust. Soc. Am.; 132(3); pp. 1368-1377; Sep. 2012.

Drafts, Bill; Acoustic wave technology sensors; Sensors Weekly (Questex Media Group); 10 pgs.; Oct. 1, 2000 (http://www.sensorsmag.com/sensors/acoustic-ultrasound/acoustic-wave-technology-sensors-936).

Foley et al.; Computer Graphics Principles and Practice; 2nd Edition; Addison Wesley (publisher); pp. 835-843; Jun. 1990.

Gibson; Visualization of lesion transmurality and depth of necrosis using an ablation catheter that incorporates ultrasound imaging: a small step or a major leap forward on the road to a more durable catheter ablation procedure for treatment of atrial fibrillation; Heart Rhythm; 8(2); pp. 313-314; Feb. 2011.

Wright et al.; Real-time lesion assessment using a novel combined ultrasound and radiofrequency ablation catheter; Heart Rhythm; 8(2); pp. 304-312; Feb. 2011.

Wu et al.; Transmural ultrasound imaging of thermal lesion and action potential changes in perfused canine cardiac wedge preparations by high intensity focused ultrasound ablation; Plos One; 8(12); pp. 1-13; Dec. 2013.

Salahieh et al.; U.S. Appl. No. 15/082,923 entitled "Steerable medical devices, systems, and methods of use," filed Mar. 28, 2016.

Salahieh et al.; U.S. Appl. No. 15/092,442 entitled "Intravascular tissue disruption," filed Apr. 6, 2016.

Salahieh et al.; U.S. Appl. No. 15/138,050 entitled "Steerable medical devices, systems, and methods of use," filed Apr. 25, 2016.

Salahieh et al.; U.S. Appl. No. 15/167,509 entitled "Intravascular tissue disruption," filed May 27, 2016.

Claude et al.; U.S. Appl. No. 15/194,444 entitled "Tissue mapping and visualization systems," filed Jun. 27, 2016.

Extended European Search Report issued in EP App;lication 15811644.2, dated Dec. 12, 2017, 8 pages.

Extended European Search Report issued in EP Application 14782484.1, dated Oct. 31, 2016, 9 pages.

International Preliminary Report on Patentability issued in PCT/US2014/033393, dated Oct. 13, 2015, 11 pages.

International Search Report issued in PCT/US2014033393, dated Aug. 19, 2014, 5 pages.

Salahieh et al., U.S. Appl. No. 15/339,724 entitled "Ablation Catheters," filed Oct. 31, 2016.

Salahieh et al., U.S. Appl. No. 15/339,745 entitled "Ablation catheters," filed Oct. 31, 2016.

Salahieh et al., U.S. Appl. No. 15/640,306, entitled "Ablation catheters," filed Jun. 30, 2017.

* cited by examiner

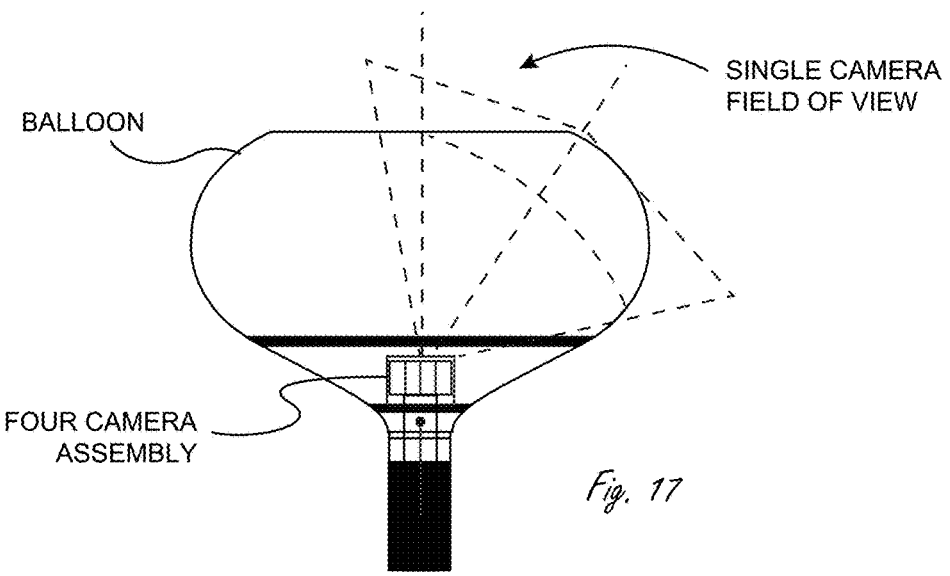
Fig. 17
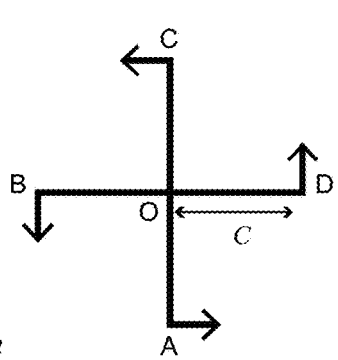
Fig. 18A
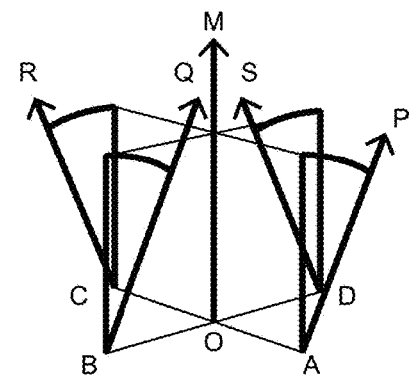
Fig. 18B
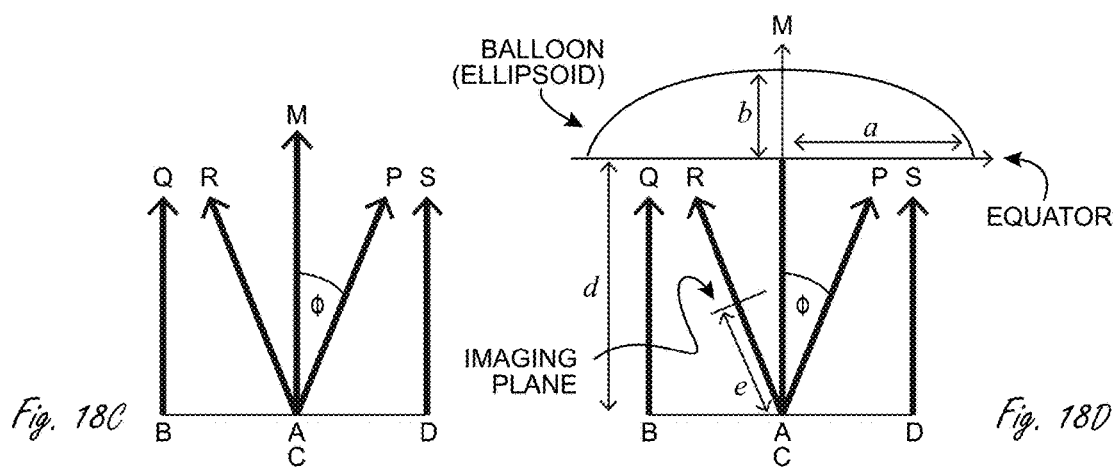
Fig. 18C
Fig. 18D

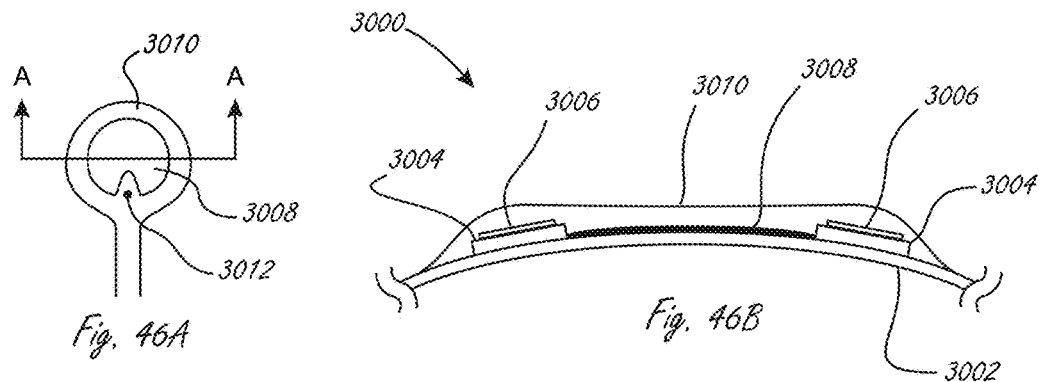
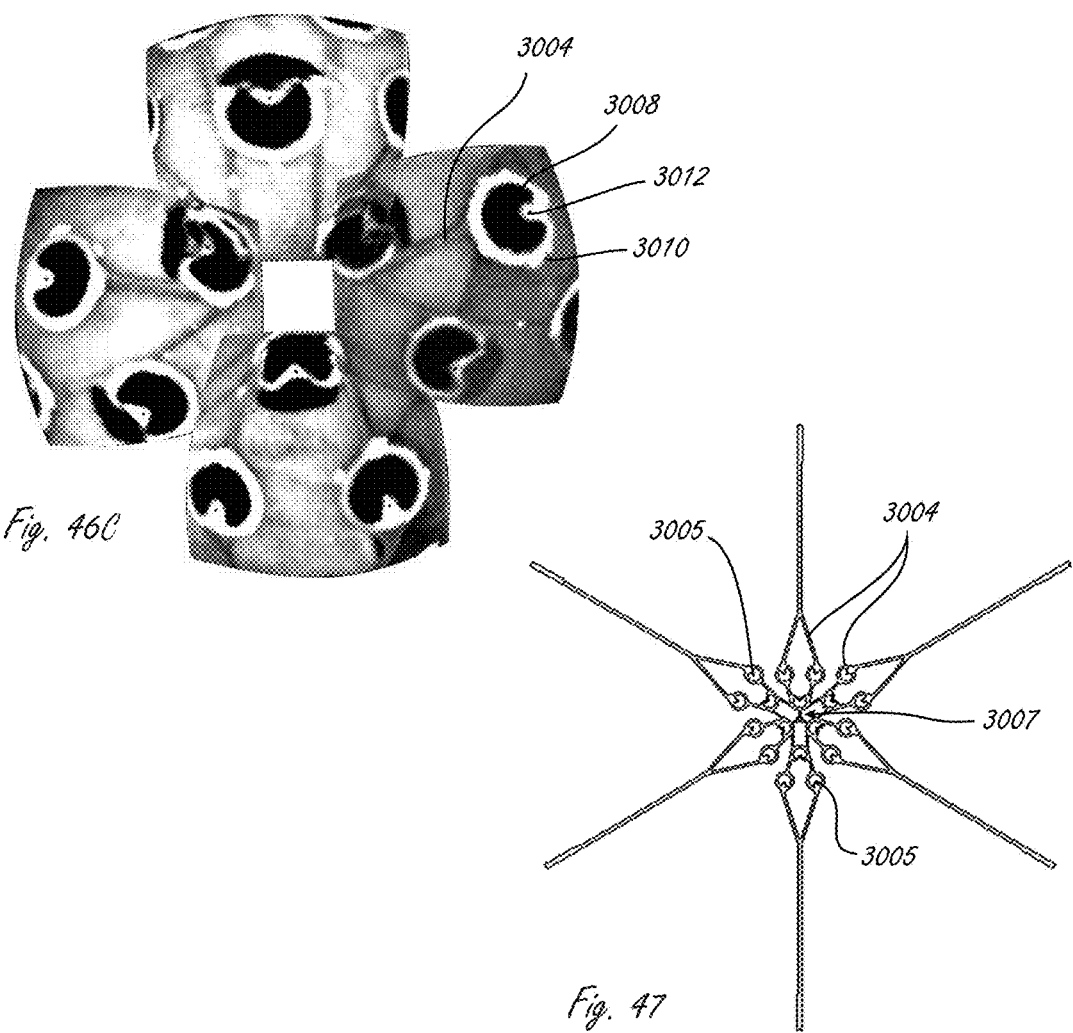
Fig. 46A
Fig. 46B
Fig. 46C
Fig. 47

TISSUE ABLATION AND MONITORING THEREOF

CROSS REFERENCE TO RELATED APPLICATIONS

This application is a continuation-in-part of U.S. application Ser. No. 14/248,288, filed Apr. 8, 2014, now U.S. Pat. No. 9,717,557, which claims priority to the following fourteen U.S. Provisional Applications: App. No. 61/809,629, filed Apr. 8, 2013; App. No. 61/809,646, filed Apr. 8, 2013; App. No. 61/895,880, filed Oct. 25, 2013; App. No. 61/809,636, filed Apr. 8, 2013; App. No. 61/864,335, filed Aug. 9, 2013; App. No. 61/829,985, filed May 31, 2013; App. No. 61/820,992, filed May 8, 2013; App. No. 61/821,001, filed May 8, 2013; App. No. 61/821,014, filed May 8, 2013; App. No. 61/934,640, filed Jan. 31, 2014, App. No. 61/939,185, filed Feb. 12, 2014; App. No. 61/934,647, filed Jan. 31, 2014; App. No. 61/945,005, filed Feb. 26, 2014, and App. No. 61/947,950, filed Mar. 4, 2014. All of the above-mentioned disclosures are incorporated by reference herein.

This application also claims priority to the following U.S. Provisional Applications: App. No. 62/043,357, filed Aug. 28, 2014; App. No. 62/025,378, filed Jul. 16, 2014; App. No. 62/127,651, filed Mar. 3, 2015; App. No. 62/142,398, filed Apr. 2, 2015; App. No. 62/150,207, filed Apr. 20, 2015; App. No. 62/016,585, filed Jun. 24, 2014; App. No. 62/149,438, filed Apr. 17, 2015; and App. No. 62/154,978, filed Apr. 30, 2015, each of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Tissue ablation devices and methods have been attempted, such as for cardiac tissue ablation. Additional devices and methods of monitoring one or more aspects of the tissue ablation are needed.

SUMMARY OF THE DISCLOSURE

The disclosure includes ablation catheters comprising an elongate shaft; an inflatable balloon carried by a distal region of the shaft; a flexible circuit, including a conductor in electrical communication with an ablation electrode, disposed outside of and carried by an outer surface of the inflatable balloon; and an ultrasound monitoring member, configured for use in monitoring at least one aspect of tissue ablation with the ablation electrode.

This disclosure also includes ablation catheters, comprising an elongate shaft; and an inflatable ablation member, carried by a distal region of the shaft, including a flexible circuit, including a conductor in electrical communication with an ablation electrode, disposed outside of and carried by an outer surface of an inflatable balloon, and an ultrasound monitoring member, configured for use in monitoring at least one aspect of tissue ablation with the ablation electrode.

The ultrasound monitoring member is optionally carried by the outer surface of the inflatable balloon, and optionally is disposed within the periphery of the ablation electrode. The ultrasound monitoring member is optionally disposed under the ablation electrode. The ultrasound monitoring member is optionally not disposed under the ablation electrode. The ultrasound monitoring member is optionally disposed under a non-conductive elastomeric material. The ultrasound monitoring member is optionally disposed outside of the periphery of an ablation electrode.

The ablation electrode is optionally a first ablation electrode, and wherein the ultrasound monitoring member is optionally disposed between the first ablation electrode and a second ablation electrode disposed outside of and secured to the outer surface of the inflatable balloon.

The ultrasound monitoring member is optionally a first ultrasound monitoring member, the ablation catheter further comprising a second ultrasound monitoring member, configured for use in monitoring at least one aspect of tissue ablation, and secured to the outer surface of the balloon. The first ultrasound monitoring member is optionally disposed within or not within a periphery of the ablation electrode. The second ultrasound monitoring member is optionally disposed within or not disposed within the periphery of the ablation electrode. The second ultrasound monitoring member is optionally disposed within or not within the periphery of a second ablation electrode. One or both of the first or second ultrasound monitoring members are optionally disposed between the ablation electrode and a second ablation electrode.

The first and second ultrasound monitoring members are optionally each selected from a group consisting of an ultrasound emitter, an ultrasound receiver, and an ultrasound transceiver.

The ablation electrode is optionally an elastomeric electrode, and wherein the elastomeric electrode is in electrical communication with, and configured for use in the operation of, the ultrasound monitoring member. The ablation catheter optionally further comprises an ultrasound conductor different than the elastomeric electrode in electrical communication with the ultrasound monitoring member. The flexible circuit optionally comprises the ultrasound conductor.

The ultrasound monitoring member is optionally an ultrasound receiver. The catheter further optionally comprises an ultrasound emitter that is a different structural element than the ultrasound receiver, and can be disposed within the balloon, or secured to the outer surface of the balloon. The ultrasound monitoring member can optionally also be an ultrasound emitter. The ultrasound monitoring member can optionally be carried by the outer surface of the balloon and disposed within or not within the periphery of the ablation electrode. The flexible circuit can optionally comprise the ultrasound receiver.

The flexible circuit optionally comprises the ultrasound monitoring member. The flexible circuit optionally comprises a substrate, and wherein the substrate comprises the ultrasound monitoring member. A substrate can optionally comprise a piezoelectric material, and optionally a portion of the substrate can be poled and another portion is not poled. A substrate optionally comprises polyvinylidene fluoride ("PVDF") or a co-polymer of PVDF. A substrate optionally comprises a flexible piezoelectric material. The ultrasound monitoring member is optionally an ultrasound receiver.

The ultrasound monitoring member optionally comprises a plurality of ultrasound monitoring members in a phased array configuration.

The ablation catheter optionally further comprises an ultrasound electrical conductor in electrical communication with the ultrasound monitoring member, wherein the flexible circuit includes the ultrasound electrical conductor.

The inflatable ablation member optionally comprises at least one irrigation port therein, and optionally the ablation electrode includes the irrigation port therethrough.

Optionally, the inflatable balloon comprises the ultrasound monitoring member. Optionally the inflatable balloon is made of a piezoelectric material, such as polyvinylidene fluoride ("PVDF") or a co-polymer of PVDF. Optionally the inflatable balloon includes at least one poled section and at least one non-poled section.

The disclosure includes a method of monitoring tissue ablation, optionally comprising: advancing an inflatable ablation member into contact with tissue, the inflatable ablation member comprising an ultrasound monitoring member and an inflatable balloon carrying a flexible circuit in conductive communication with at least one ablation electrode; and activating the ablation electrode and monitoring at least one aspect of tissue ablation with the ultrasound monitoring member. The ultrasound monitoring member is optionally positioned between first and second ablation electrodes carried by the inflatable balloon, wherein monitoring optionally comprises monitoring the tissue with the ultrasound monitoring member to determine when an ablation zone from the first and second ablation electrodes join.

The disclosure includes ablation catheters, optionally comprising: an inflatable balloon carried by a distal region of an elongate shaft; and a flexible circuit carried by an outer surface of the balloon, the flexible circuit comprising a substrate and a conductor, the substrate including a discontinuity, and at least one ablation electrode, in electrical communication with the conductor, carried by the outer surface of the balloon and disposed over the discontinuity. The discontinuity is optionally a hole in the substrate. The discontinuity is optionally at least partially filled with a reflection adjuster, such as a black paint, or a conductive black paint.

The disclosure includes ablation catheters, optionally comprising: an inflatable balloon secured to a distal region of an elongate shaft; and a flexible circuit carried by an outer surface of the balloon, the flexible circuit including an electrical conductor in electrical communication with an ablation electrode and an electrophoretic ink disposed radially within the ablation electrode, the electrophoretic ink being adapted to change absorbance upon activation. The electrical conductor is optionally a transparent conductor. The electronic ink is optionally radially between the conductor and the ablation electrode. The ablation electrode is optionally a conductor adapted for use in activating the electrophoretic ink. Activation optionally comprises supplying a charge across the electrophoretic ink. The electrophoretic ink is optionally also disposed in a discontinuity in a substrate layer of the flexible circuit. The electrophoretic ink is optionally a light absorber.

BRIEF DESCRIPTION OF THE DRAWINGS

FIG. 17 is a side view of a distal portion of an exemplary visualization catheter.

FIGS. 18A-18D show the orientations of the axes of four cameras in relationship to the longitudinal axis of a catheter shaft.

FIGS. 46A-46C illustrate an exemplary expandable member that includes a discontinuity in at least one flexible circuit layer.

FIG. 47 illustrates an exemplary substrate for a flexible circuit.

DETAILED DESCRIPTION

The disclosure describes methods of, and systems and devices configured for, diagnosing, preventing, and/or treating cardiac arrhythmias. The disclosure includes methods of, and devices configured for, ablating cardiac tissue and monitoring one or more aspects of the tissue ablation. The disclosure is related to and incorporates by reference the devices and methods described in U.S. Pat. No. 8,295,902, issued Oct. 23, 2012, and U.S. Pub. No. 2012/0071870, published Mar. 22, 2012, the disclosures of which are incorporated by reference herein. Devices herein can incorporate suitable structural features in embodiments in the aforementioned applications even if the disclosure fails to expressly include them. Additionally, the methods of use herein can include suitable method steps in embodiments in the aforementioned applications even if the disclosure fails to expressly include them.

Figure 1A:
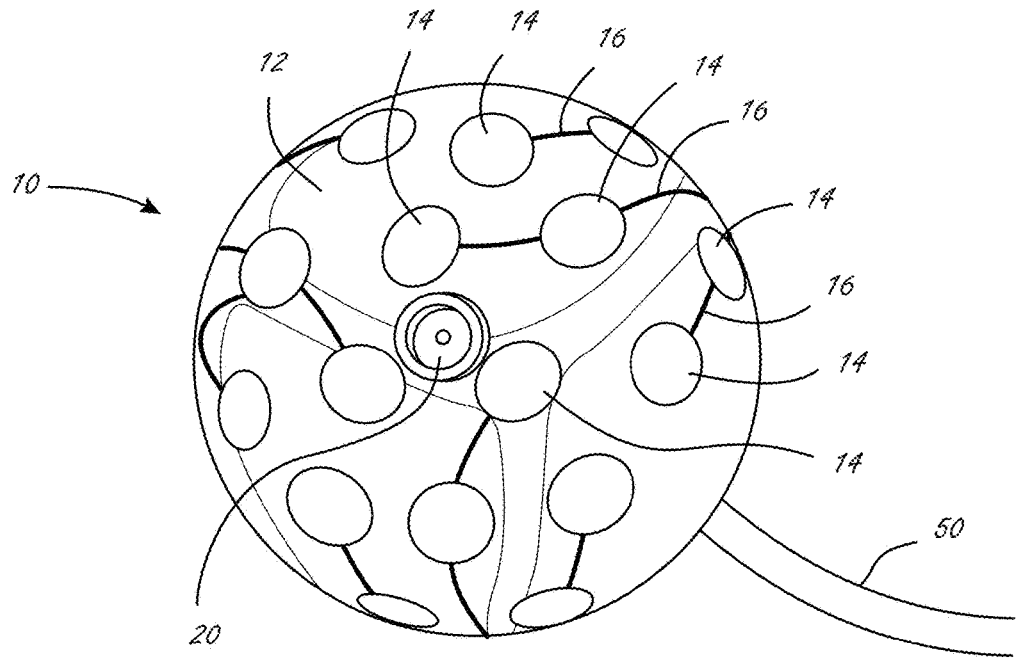
FIGS. 1A-1C illustrate an exemplary ablation device in expanded configurations.
Figure 1B:
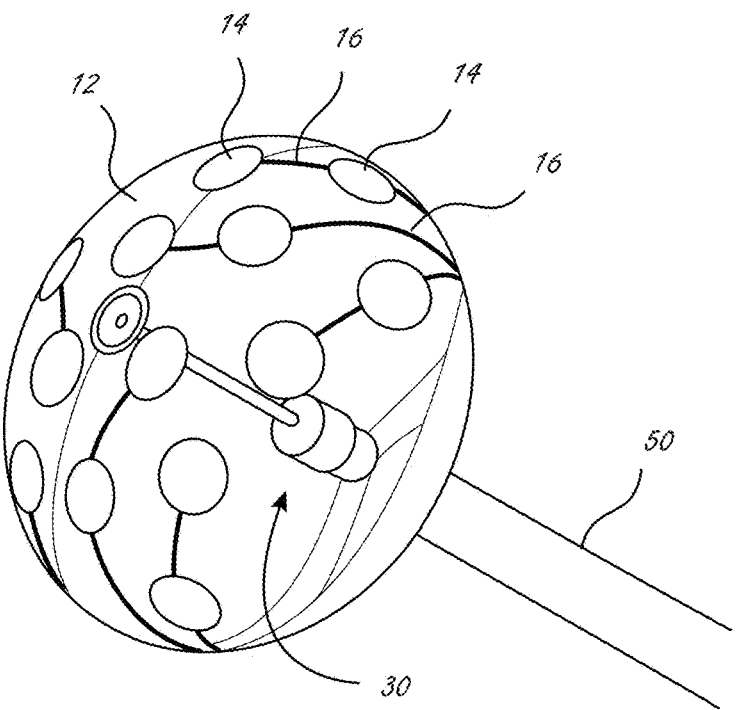
Figure 1C:
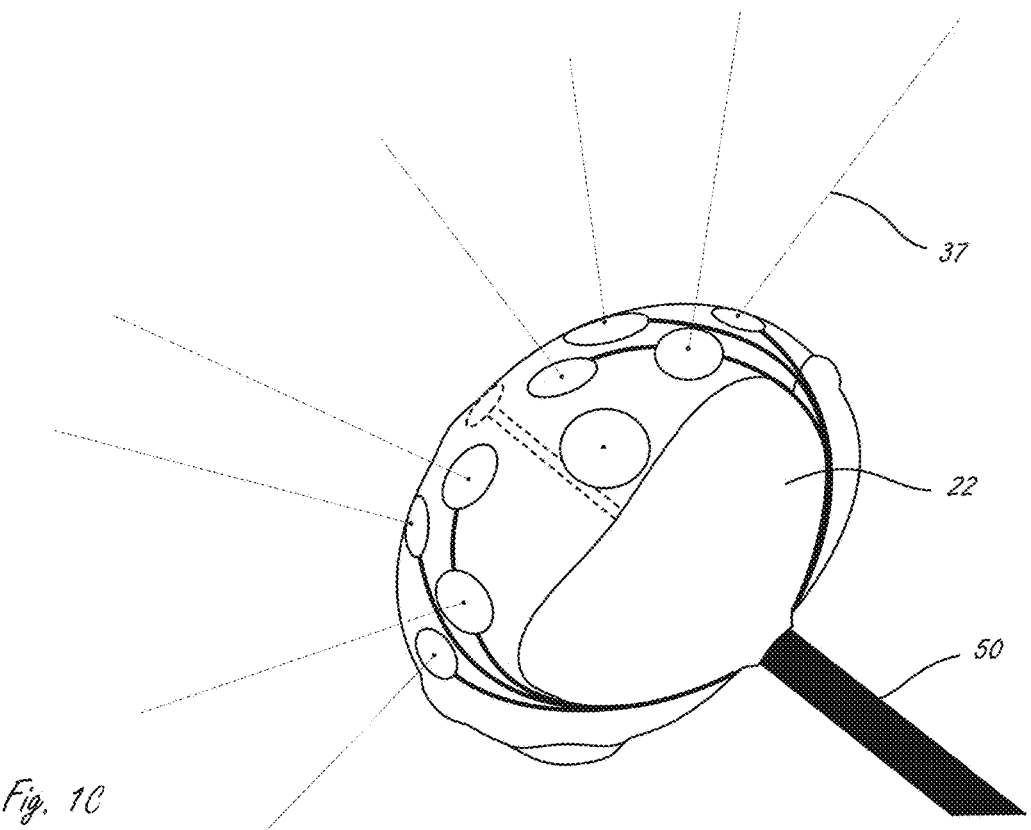

FIGS. 1A-1C illustrate a distal portion of an exemplary cardiac ablation catheter. FIGS. 1A-1C shows expandable member 10 in an expanded configuration. FIG. 1A is a distal view, FIG. 1B is a perspective view, and FIG. 1C is a side view. Examples of the expandable members are the "inflatable ablation members" described below.

The cardiac ablation catheter is configured to deliver ablative energy to tissue such as cardiac tissue and to ablate the tissue. Expandable member 10 includes membrane, or balloon, 12 and a plurality of energy delivery elements 14 secured to the exterior of membrane 12. In this embodiment energy delivery elements 14 are electrodes configured and positioned to deliver ablative RF energy to tissue when expandable member 10 is inflated and to ablate the tissue, and are in electrical communication with an RF generator (not shown) configured to generate RF energy.

Figure 1D:
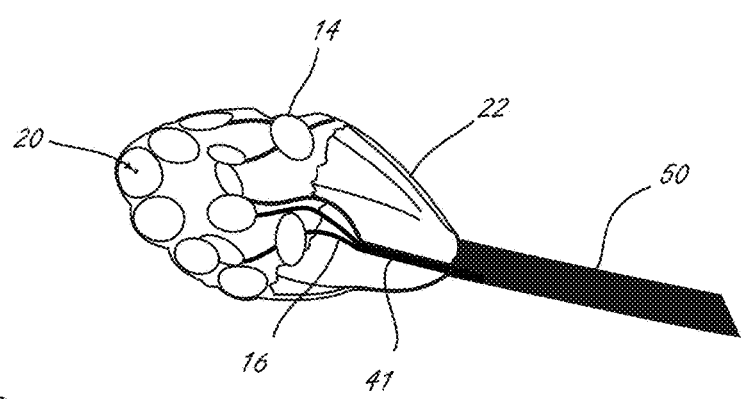
FIG. 1D illustrates an exemplary ablation device in a collapsed configuration.

FIG. 1D illustrates expandable member 10 in a collapsed, or deflated, configuration prior to full inflation.

Figure 2A:
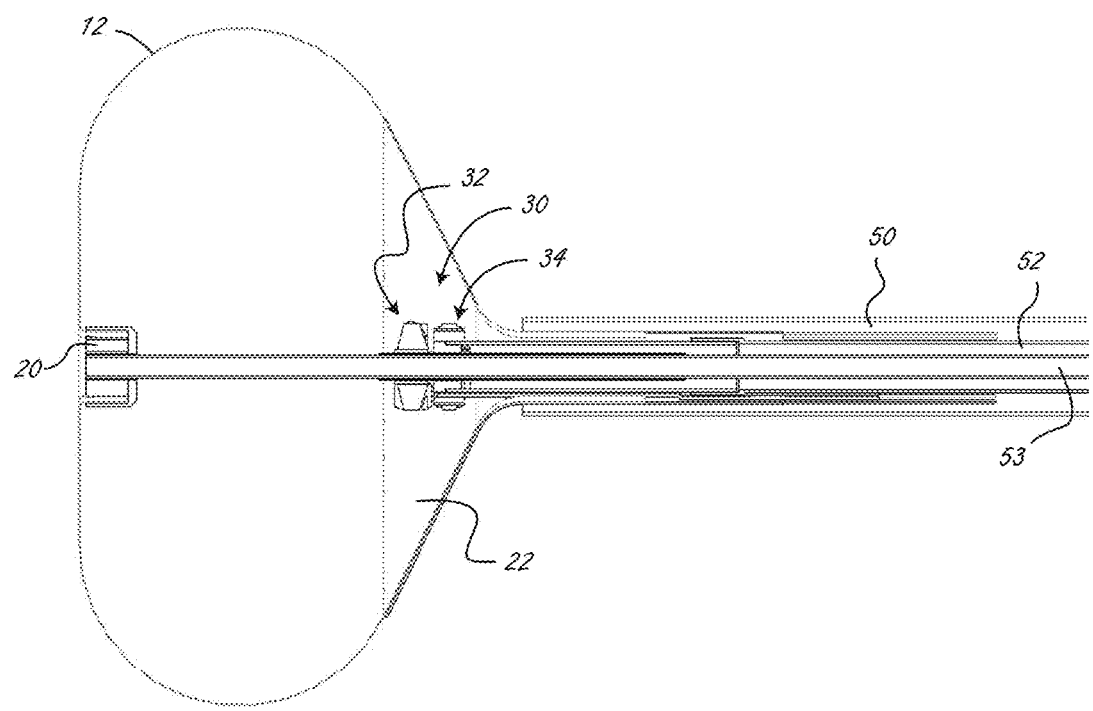
FIG. 2A is a side view of an exemplary distal end of an ablation catheter.
Figure 2B:
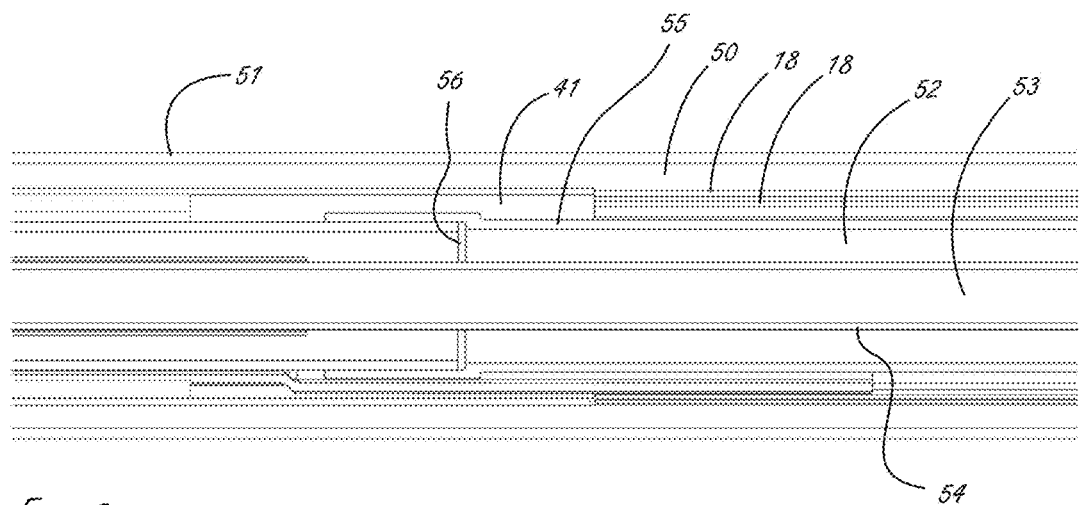
FIG. 2B is a close up side view of the inside of the catheter from FIG. 2A.

FIG. 2A is a side sectional view of the distal portion of the ablation catheter shown in FIGS. 1A-1C. FIG. 2B is a highlighted side sectional view of components within outer shaft 51. FIG. 2A shows membrane 12 expanded at the distal end of outer lumen 50, which is the annular space between outer shaft 51 and irrigation shaft 55. The distal end of membrane 12 is secured, such as by press-fit and/or adhesive, to distal hub assembly 20, between an inner member and an outer member of assembly 20 as shown. The proximal end of membrane 12 is secured to the outer surface of irrigation shaft 55. Hub 20 is secured to guide wire shaft 54, which in this embodiment defines guidewire lumen 53 so that the ablation catheter can be advanced over a guidewire (not shown). Guidewire shaft 54 and irrigation shaft 55 are adapted to be axially movable relative to one another, which allows the distal end of membrane 12 to be moved relative to the proximal end of membrane 12. Relative movement between the two components can allow for the shape of the balloon to be changed. The movement also assists in transitioning expandable member 10 to a collapsed configuration, as shown in FIG. 1D.

Visualization system 30 includes a camera assembly 32 and illumination sources 35 disposed on the guide wire shaft 54. The cameras are configured to enable real-time imaging of the procedure from within the expandable member 10 to visualize the membrane and electrodes, cardiac tissue when the membrane/electrodes and cardiac tissue interface, as well as lesion formation during the ablation procedure, as is described in more detail below.

FIG. 2B shows radially outer shaft 51, irrigation shaft 55 that defines irrigation lumen 52, and guide wire shaft 54 that defines guidewire lumen 53.

The materials of the membranes 12 described herein can vary. Generally, the membrane material is thin, readily foldable into a low profile and refoldable after expansion. The materials can be elastic, inelastic, stretchy, non-stretchy, compliant, semi-compliant, or non-compliant. In an embodiment, membrane 12 has an expandable structure and can be constructed of materials such as those materials used in the construction of balloon catheters known in the art, including, but not limited to polyvinyl chloride (PVC), polyethylene (PE), cross-linked polyethylene, polyolefins, polyolefin copolymer (POC), polyethylene terephthalate (PET), nylon, polymer blends, polyester, polyimide, polyamides, polyurethane, silicone, polydimethylsiloxane (PDMS) and the like. Membrane 12 can be constructed of relatively inelastic polymers such as PE, POC, PET, polyimide or a nylon material. Membrane 12 can be constructed of relatively compliant, elastomeric materials including, but not limited to, a silicone, latex, urethanes, or Mylar elastomers. Membrane 12 can be embedded with other materials such as for example, metal, Kevlar or nylon fibers. Membrane 12 can be constructed of a thin, non-extensible polymer film such as polyester or other flexible thermoplastic or thermosetting polymer film. In one embodiment flexible membrane 12 can be about 0.001" to about 0.002" in thickness to provide sufficient burst strength and allow for foldability. In some embodiments it is preferable to have the electrode mechanical properties as close to the membrane mechanical properties as possible. One way of providing this is to use an inelastic membrane that will not stretch as it is expanded. This helps secure the branches to the membrane. Membrane 12 has a front, or distal, face that is generally flat but can have other shapes as well.

Expandable member 10 includes what is generally referred to in U.S. Pat. No. 8,295,902, issued Oct. 23, 2012, and U.S. Pub. No. 2012/0071870, published Mar. 22, 2012, as flex, or flexible, circuits. A flex circuit as used herein generally refers to a conductive layer, an insulation layer, and optionally a substrate layer. A flex circuit is in electrical communication with at least one electrode.

Figure 8:
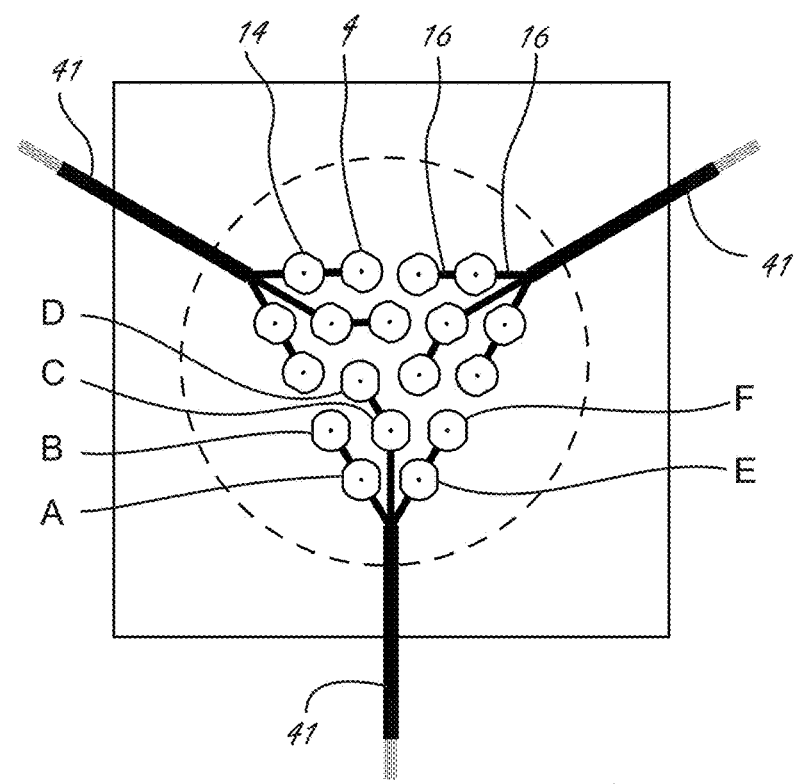
FIG. 8 is a flat view showing three individual flex circuits that are secured to the exterior of membrane and to electrodes.

FIG. 8 is a flat view showing three individual flex circuits that are secured to the exterior of membrane 12. Each of the three flex circuits includes six energy delivery elements 14, and a tail terminating in termination 41 for the six conductive traces, one for each of the six electrodes. The terminations may be in the form of a connector or solder pads or other such suitable interface. The terminations 41 extend proximally from energy delivery elements on the expandable member, one of which can be seen in FIG. 1D. Each of the tails branch off into three branches 16, each one of which includes two energy delivery elements. Each of the two side branches 16 extend away from the longitudinal axis of the connector at substantially the same angle and each of two electrodes on a side branch is disposed at the same axial position (in the distal/proximal direction) as the other corresponding electrode on the other side branch. The central branch, however, initially extends along the same general direction as the longitudinal axis of a tail, and the first electrode on the central branch is axially disposed at the same general location as the second electrodes on the right and left branch. The central branch then extends away from the longitudinal axis of the tail, and the second (distal) electrode on the central branch is disposed further distally than the other five electrodes on the flex circuit, and is disposed radially (relative the longitudinal axis of tail) at the same general position as the first (proximal) electrode on one of the other side branches. In FIG. 8, the six electrodes on one of the flex circuits are labeled A-F. The two side branches of the flex circuit include electrodes A-B and E-F respectively. The central branch includes electrodes C and D. In the flat view, electrode C (the distal electrode of the central branch) is axially disposed at the same general position as electrodes B and F. Electrode D is disposed further distally than the other five electrodes, and is positioned radially in the same general position as electrode A. Electrodes A and E are disposed in the same general axial position, as are electrodes B, C, and F. Each of the three flex circuits is positioned on the expandable member, and the arrangement and size of electrodes provides for eighteen electrodes secured to the expandable member. As can be seen in FIGS. 1A and 1B, there are three electrodes closely surrounding hub 20.

Figure 9A:
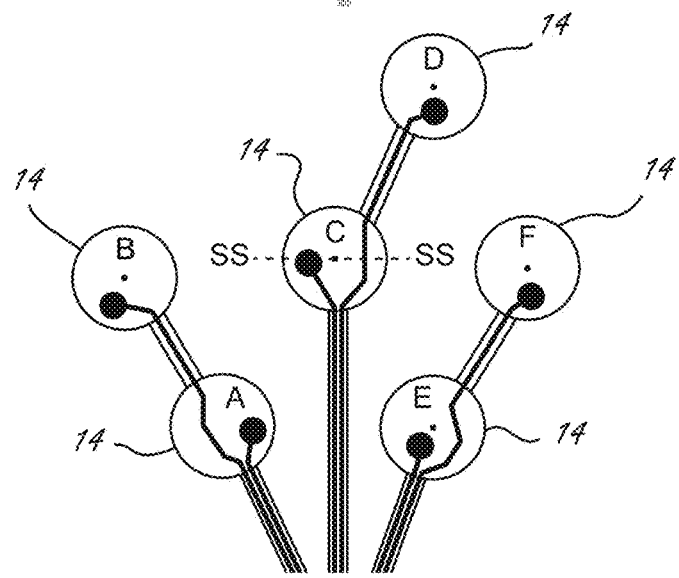
FIG. 9A illustrates a portion of one of the flex circuits and electrodes in FIG. 8.
Figure 9B:
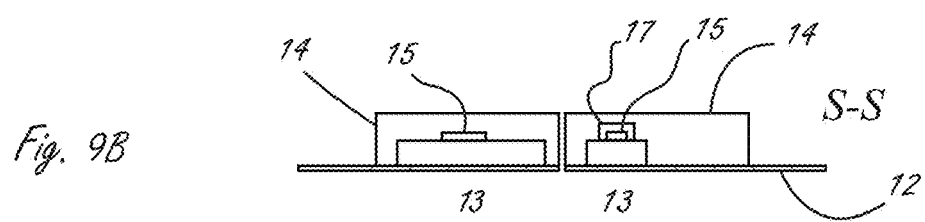
FIG. 9B illustrates the exemplary different layers of the flex circuit from section S-S from FIG. 9A.

FIG. 9A illustrates a portion of one of the flex circuits in FIG. 8 (the flex circuit in which termination 41 is at the "6 o'clock" position), including six energy delivery elements 14. FIG. 9A shows as alternative embodiment in which the distal electrode on the central branch 16 extends to the right on the page rather than the left, as is shown in FIG. 8. This arrangement provides the same general arrangement of the eighteen electrodes on the balloon. In the embodiment in FIGS. 1A-1C, there are three of the flex circuits from FIG. 9A disposed on membrane 12, and thus eighteen energy delivery elements secured to membrane 12. FIG. 9B illustrates the exemplary different layers of the flex circuit from section S-S from FIG. 9A. Electrically non-conductive substrate layer 13 is deposited on membrane 12, upon which conductive layers, or traces, 15 are deposited. Insulation layer 17 is deposited on top of conductive layers 15 except where the electrodes 14 are located. For example, to the left in FIG. 9B, an electrode 14 is disposed on electrically conductive element 15, thus electrically coupling electrode 14 and conductive layer 15, which is electrically coupled to an RF generator. On the right side of FIG. 9B, insulation layer 17 prevents conductor 15 on the right side from being electrically coupled to electrode 14. Instead, the conductor 15 on the right side will be electrically coupled to the distal electrode on that branch. Each individual conductor 15 is therefore electrically coupled to only one electrode 14. In the figure shown in 9A, there are six individual conductive traces 15, each of which is individually coupled to one electrode. As is described in detail in U.S. Pat. No. 8,295,902, issued Oct. 23, 2012; U.S. Pub. No. 2012/0071870, published Mar. 22, 2012, the electrodes are sized and configured to extend over a portion of the flex circuit and a portion of membrane not covered by the flex circuit. In this manner a large surface area electrode can be deposited onto and secured to the membrane. Each electrode is shown with an irrigation aperture in the middle thereof, as is described herein to irrigate tissue adjacent the electrodes and to prevent the irrigation fluid inside the membrane from becoming too hot and interfering with the tissue ablation.

The conductor or conductive layer 15 can be a material such as, but not limited to, a metal or metal foil of copper, gold, silver, tin, nickel, steel, cupronickel (copper-nickel alloy), KOVAR (nickel-cobalt ferrous alloy) or other material. In an embodiment, more than one conductive material can be used in the conductive layer 15. In an embodiment, a conductive layer 15 of copper can be plated with a thin layer of an additional conductive material at the conductive pad beneath electrode 14. In an embodiment, the thin layer of additional conductive material can be gold. The flex circuit and its components can be manufactured using techniques as known in the art.

The materials used to create the electrodes 14 can vary. The electrodes 14 can be a thin film of an electro-conductive or optical ink. The ink can be polymer-based for better adhesion to the membrane. The electrode material can be a biocompatible, low resistance metal such as silver, silver flake, gold, and platinum which are additionally radiopaque. Inks may additionally comprise materials such as carbon and/or graphite in combination with the more conductive materials already described. The addition of carbon and/or graphite can increase the conductivity of the polymer matrix. When incorporated as fibers the carbon and/or graphite add additional structural integrity to the ink electrode. Other fiber materials may be substituted to attain the same end. When the electrode material is not particularly radiopaque, additives such as tantalum and tungsten may be blended with the electrode material to enhance radiopacity. An example of an electro-conductive ink is provided by Engineered Conductive Materials, LLC (ECM) which is a polyurethane-based silver loaded ink. Another example is Creative Materials Inc., which manufactures conductive inks, films, as well as radiopaque inks. As mentioned above, the electrodes 14 can be applied to the membrane 12 and flex circuit using an adhesive. Alternatively, the electrode material can have adhesive properties or be an adhesive-loaded with conductive particles such as silver flakes such that electrodes 14 can adhere the components of the flex circuit to the membrane 12. If an additional adhesive layer is used to adhere the electrode 14 to the membrane 12 and flex circuit, the adhesive layer can include a conductive or non-conductive material. The electrodes formed with electro-conductive or optical ink or thin metal film can be visualized under fluoroscopy to provide a general sense of the shape of the membrane and location of the electrode. To enhance visualization under fluoroscopy, radiopaque additives can be included in the electrode material or radiopaque markers laid out next to, on top or below the electrodes as will be discussed in more detail below. Additionally, the bonding layer or substrate will be optimally comprised of a minimally reflective material.

Figure 34:
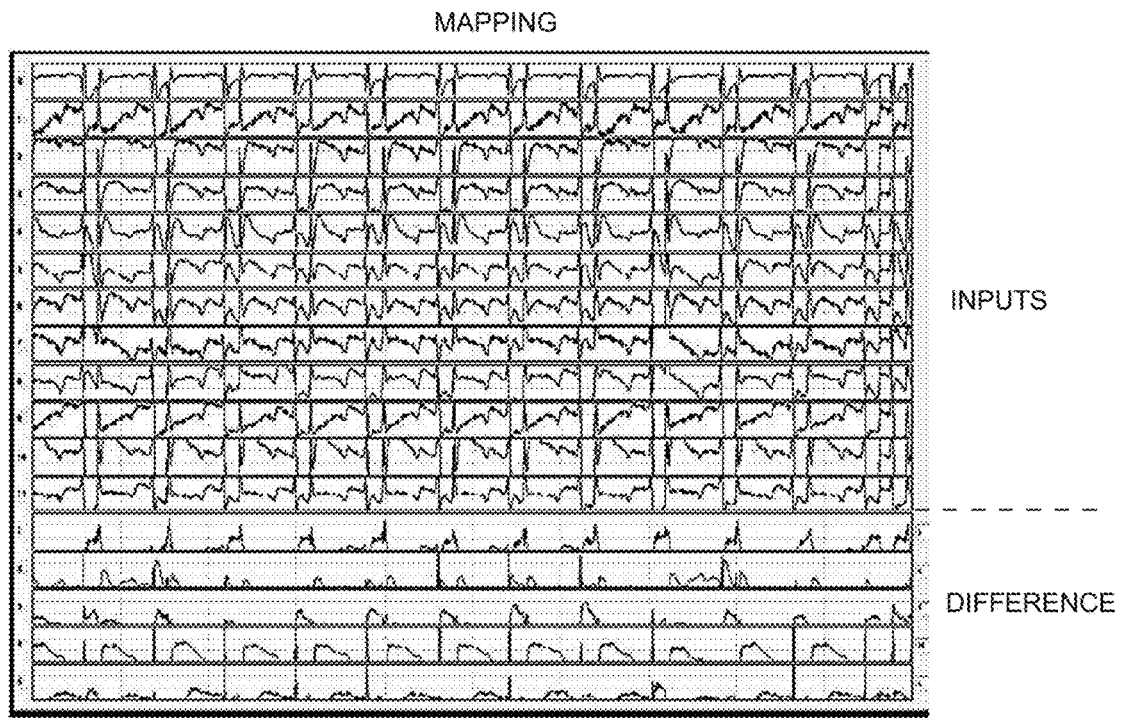
FIG. 34 illustrates mapping signals from a plurality of channels.

Each of the electrodes is individually addressable, or can be used with any other electrode. The electrodes can operate in monopolar mode or bipolar mode, as is indicated in the exemplary schematic shown in FIG. 34. Electrodes sets can be chosen such that the lesion is, for example without limitation, linear, a spot, or a hollow circle.

Figure 3:
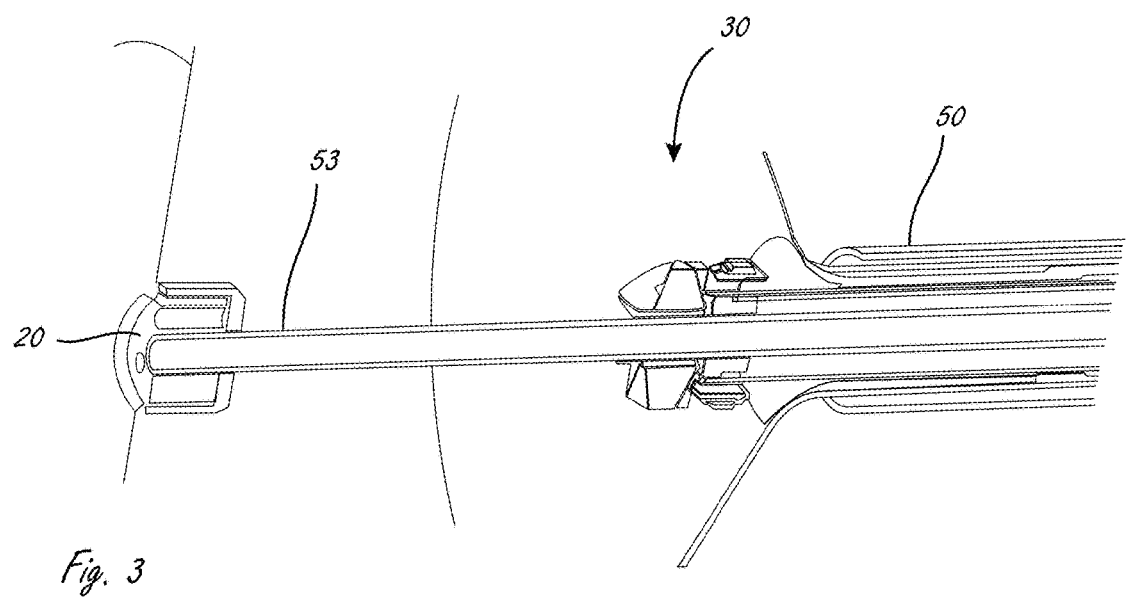
FIG. 3 is a perspective view showing inside the expandable membrane.

FIG. 3 illustrates the coupling of the distal end of membrane 12 and hub 20, which can be press fit, adhesive coupling or a combination of both.

To prevent or reduce the likelihood of charring of tissue that is in contact with the energy delivery elements and coagulation of blood adjacent the electrodes, each of the flex circuits at the locations of the electrodes includes an irrigation aperture therethrough, and as shown are in the center of the electrodes. The irrigation apertures also prevent the inflation/irrigation fluid inside the membrane from becoming too hot, which would interfere with the ablation. Irrigation fluid, which is also the fluid that inflates membrane 12 causing it to be reconfigured toward its expanded configuration, is pumped from a fluid source through irrigation lumen 52, into membrane 12, through the irrigation apertures (not labeled), and towards the tissue that is in contact with the electrodes to cool the target tissue. One of the drawbacks of previous attempts at cardiac ablation is that the ablation procedures cause blood to coagulate or tissue to char due to lack of a cooling feature. Additionally, since each electrode is individually addressable, and the visualization system allows the operator to identify whether an individual electrode is in contact with tissue, only electrodes in contact with tissue may be turned on. Thus energy is more efficiently coupled to just the sites where ablation is desired and little to no energy is dissipated into the blood.

One of the significant advantages of some of the ablation catheters herein is that, when in use, the ablation procedures can be visualized with an imaging, or visualization, member with a perspective from within the inflatable membrane. In the embodiment in FIGS. 1A-1D, imaging member 30 includes camera assembly 32 that includes a plurality of cameras 33 and a plurality of illumination, or light, sources, 35 (e.g., LEDs). Expandable member 10 also includes diffuse reflector 22 that is secured to the external surface of membrane 12. Reflector 22 is a diffuse reflector adapted to create diffuse reflection of light incident upon it from the illumination sources. Reflector 22 is adapted to reflect light in a diffuse manner, as opposed to specular reflection, to better illuminate as much of the camera field of view as possible. If the reflector were adapted for specular reflection rather than diffuse reflection, light from the illumination sources that is reflected from the reflector would appear in the camera's field of view as a localized spot and would not illuminate as much of the field of view as possible.

Illumination sources 35 are configured and positioned to provide illumination generally radially outward towards reflector 22. Diffuse reflector 22 thus diffusely reflects light forward toward the camera's fields of view. The illumination sources thus provide lighting for the cameras to visualize the procedure, including the tissue, and the lesion formation.

In some embodiments the diffuse reflector is printed on the exterior of the balloon. The diffuse reflector can be comprised of silicone or urethane resins filled with nonconductive white pigment such as TiO, BaO, BaSo4, styrene or other polymer beads, or of metal particles. Optimal materials will be minimally reflective such as a black adhesive.

In this embodiment the diffuse reflector is secured to the membrane such that it does not completely overlap any of the electrodes, and is positioned so that the illumination sources, when activated, emit light towards the reflector. In this embodiment the diffuse reflector, or reflectors, is secured to the membrane at a location that does not extend all the way to the distal end of the membrane. In this embodiment the reflector is secured to the membrane such that it does not extend further distally than the proximal-most electrode. In alternative embodiments, however, the reflector can extend distally to the proximal-most electrode in some locations around the membrane. For example, the distal edge of the reflector can be curved rather than straight, and depending on the electrode layout on the membrane, some portions of the reflector may extend distally relative to the proximal-most electrode. If the membrane in its inflated configuration can be divided in half between the distal most location and proximal most location defining a distal portion and proximal portion, the reflector is disposed at least on the proximal portion. In the embodiment shown in FIGS. 1A-1C, the reflector is disposed only on the proximal portion.

One aspect of the disclosure is an expandable member that includes a diffuse reflector but does not include any ablation element. For example, medical devices that include an inflatable member and at least one camera and at least one light source therein can benefit from a diffuse reflector even if the device is not used for ablation procedures.

While the reflector herein is described as being a diffuse reflector, there may be some uses in which a reflector that reflects light in a specular manner may be beneficial. Alternatively, a reflector can have portions that reflect light in a diffuse manner and portions that reflect light in a specular manner.

Figure 4:
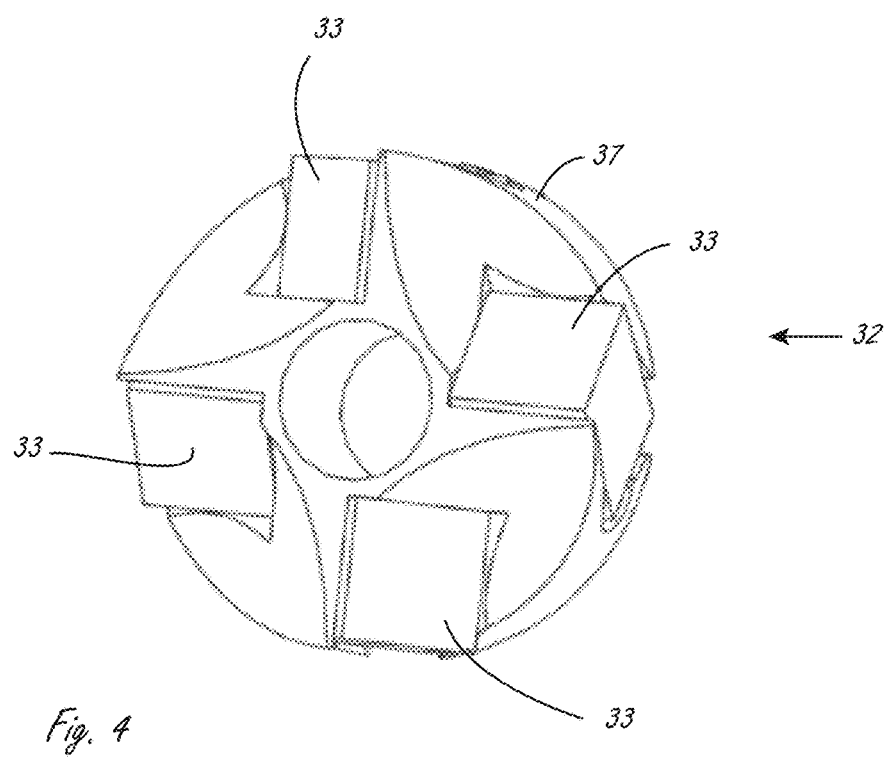
FIG. 4 illustrates a camera assembly.

FIG. 4 shows an exemplary camera assembly 32 that includes four cameras 33, which are disposed within camera hub 37 at an angle relative to the longitudinal axis of the catheter. Camera hub 37 is secured to guide wire shaft 54, and includes lumen 39 configured to receive guide wire shaft 54 therein.

Figure 5:
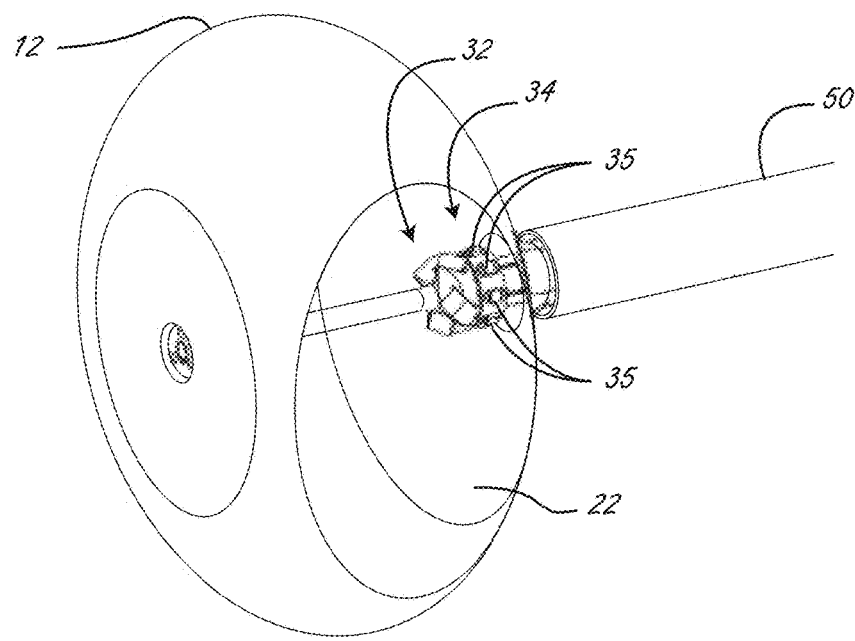
FIG. 5 is a perspective view of a distal end of an ablation catheter, with a cutaway of an expandable member.
Figure 6:
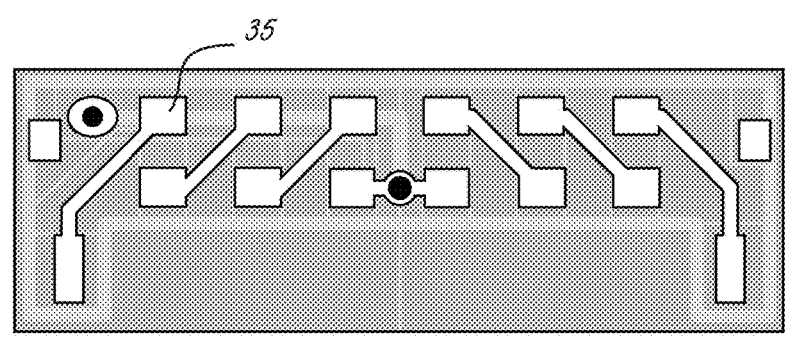
FIG. 6 is an exemplary flat view of the LED flex circuit.

FIG. 5 is another perspective view of expandable member 10 with a cutaway of the membrane. FIG. 6 is an exemplary flat view of the LED flex circuit, including the LEDs, that is wrapped around the illumination hub proximal to the cameras.

As set forth above, light is reflected from the diffuse reflector to provide illumination in the field of the view of the at least one camera. The field of view of the camera can include the view of an electrode secured to the membrane. As set forth herein, the electrodes can be highly reflective, such as if they are comprised of silver. Reflective electrodes causes light incident upon the electrodes to reflect into the camera field of view, which can cause the electrodes to appear as bright spots on the display, possibly interfering with viewing the procedure. It can thus be beneficial to include in the catheter an optional reflection adjuster that is adapted to reduce specular reflection of light from at least one of the plurality of ablation electrodes into the field of view of an imaging member.

In some embodiments the reflection adjuster is a light absorber. The light absorber can be positioned between the bottom of the electrodes and the membrane. In some embodiments the light absorber is a black adhesive that adheres portions of the electrode to the membrane, as well as acts as a light absorber.

In some embodiments the reflection adjuster is an anti-reflective coating. Exemplary anti-reflective coatings include, for example without limitation, a deposited thin layer of $TiO_2$, MgF2, and "moth eye" structures comprised of nanoparticles approximately 200 nm in diameter spaced 300 nm range, random microstructure secured to or created on the interior surface of the membrane that is adapted to reduce reflection. The anti-reflective coating can be adhered to only a portion of the membrane, such as the portion where the electrodes are disposed. For example, an anti-reflective coating could be applied to only the distal portion of the inner membrane.

A reflection adjuster will reduce the amount of reflection from the bottom of the electrodes, creating a clearer image of the membrane and electrodes from within the membrane.

When the images or video provided by the optional at least one camera are displayed on the display, it can be helpful to be able to visually identify the electrodes on the display. For example, a user interface can be used to control delivery parameters for any of the electrodes, and enabling the physician to easily determine and confirm that a given electrode on the video is a particular electrode on the user interface simplifies the procedures and ensures that the correct electrodes are being activated and used as intended.

In some embodiments the catheter includes an electrode identifier associated with at least one of the plurality of electrodes, and is some embodiments the catheter includes an electrode identifier with each of the plurality of electrodes. The electrode identifier need not be unique to each of the electrode, but in some embodiments it is unique to each electrode. The electrode identifier is visually identifiable and allows an individual to visually associate the identifier with an electrode.

In some embodiments the electrode identifier is an alphanumeric characters disposed on or near each of the electrodes. An example of this type of identifier is described and shown below. For example, an alphanumeric character can be printed on the back of an electrode, or the back of a portion of the flex circuit that is associated with an electrode. An alphanumeric character can also be printed on the membrane near the electrode so that the identifier can be easily associated with a particular electrode.

In some embodiments the electrode identifiers are colors associated with one or more of the electrodes. For example, the electrodes can be color-coded so that a user can visually identify each of the electrodes. In some embodiments a group of electrodes can have a particular color, such as all of the electrodes connected to the same flex circuit are all one color. An additional example of an electrode identifier is the shape of the electrode so that the electrode or group of electrodes can be visually identified based on their shape. For example, groups of electrodes can be circular, oval, hexagonal, rectangular, square, etc. Each electrode could have a unique shape to it as well.

An example of electrode identifiers is described below in the context of overlaying field of view images from a plurality of cameras.

Figure 10:
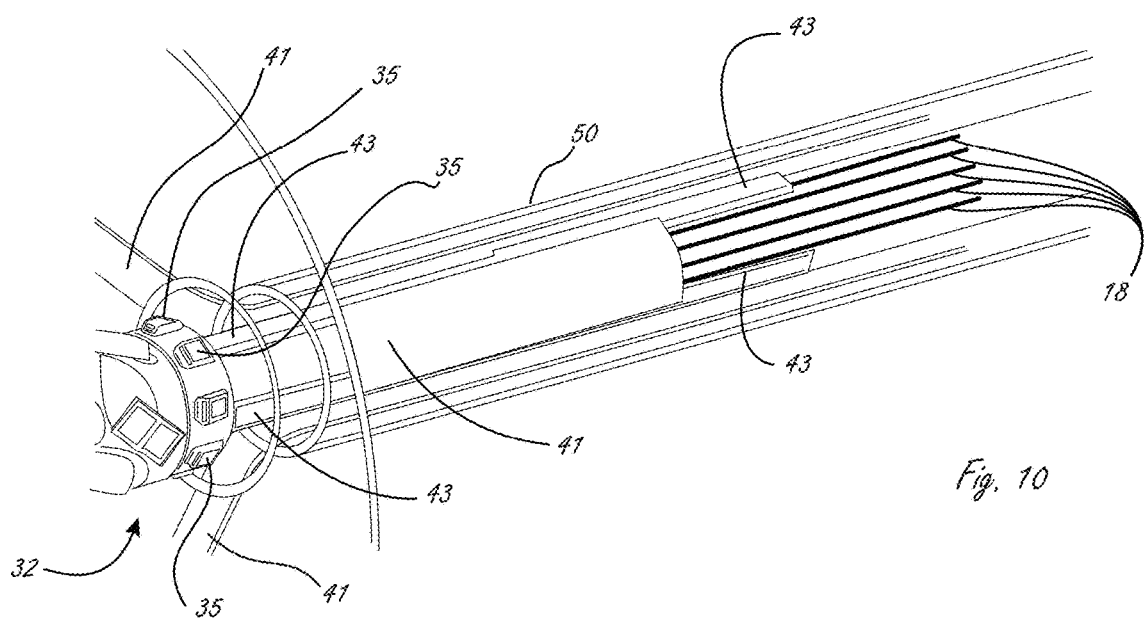
FIG. 10 illustrates each of the three flex circuit tails terminating in terminations extending proximally from the distal end of the balloon and extending proximally within an outer shaft and secured to the outer surface of the proximal end of the balloon and irrigation shaft.

FIG. 10 illustrates each of the three flex circuit tails terminating in terminations 41 (one for each flex circuit) extending proximally from the distal end of the balloon and extending proximally within outer shaft 51 and secured to the outer surface of the proximal end of the balloon and irrigation shaft 55. The proximal aspect of the configuration can also be seen in FIG. 2B. In FIG. 10, six conductive wires 18 can be seen extending proximally from one of the terminations 41, each one of which is in electrical communication with one of the six electrodes in that particular flex circuit. The six wires 18 extend the length of the catheter and are in communication with the RF generator. In an alternate embodiment, not shown, the six conductive traces 15 extend the length of the catheter and are in communication with the RF generator. Camera flex circuit 43 for the visualization system is also shown in FIG. 10, extending proximally from the visualization system in the catheter.

Exemplary materials for the membrane and flex circuit materials can be found in U.S. Pat. No. 8,295,902, issued Oct. 23, 2012; U.S. Pub. No. 2012/0071870, published Mar. 22, 2012. Additional examples of membrane material include PET, Polyurethane, etc. Exemplary materials for the reflector include metalized paints, silicone or urethane resin filled with nonconductive white pigment such as TiO or BaO or BaSo4, preferably non-conductive. Exemplary materials for the electrodes include silver filled silicone or urethane. Exemplary materials for the conductive traces are conductive metals including copper or other such conductive materials. The insulation layers can be known dielectric materials. Exemplary materials for the substrate include Kapton.

As described herein ablation catheters can include ablation and mapping electrodes secured to the exterior of the membrane. In such embodiments the area of tissue mapped is limited to the area of contact defined by the inflatable structure. The rotors being mapped can, however, be larger than the contact area of the inflatable structure, making it more difficult and time consuming to properly map the atrial chamber for rotors. In some embodiments the ablation catheter includes an inflatable membrane, and is also adapted to increase the area that can be mapped to an area that is greater than that defined by the expandable membrane contact surface.

In some of these embodiments mapping arms when appropriately stiff may provide a way to limit the accidental entry of the ablation elements into the pulmonary arteries thereby minimizing the risk of accidental ablation of the artery wall and consequent risk of subsequent stenosis.

In some embodiments a mapping structure on which at least one mapping electrode is disposed is carried outside of the balloon and collapsed between the wall of the delivery catheter and the outside of the ablation catheter. The mapping structure can be secured to the exterior of the ablation catheter. In some embodiments the one or more mapping structures can be deformable splines, the use of which has been described in the cardiac ablation space. For example, the mapping structures can be made of nitinol and are adapted to deform. The mapping structure can thus expand on release from the delivery catheter and can be collapsed to a collapsed delivery configuration when the delivery catheter is advanced distally relative the ablation catheter In other embodiments a mapping electrode structure is adapted to be delivered through the guide wire lumen of the ablation catheters herein.

Figures 11A, 11B:
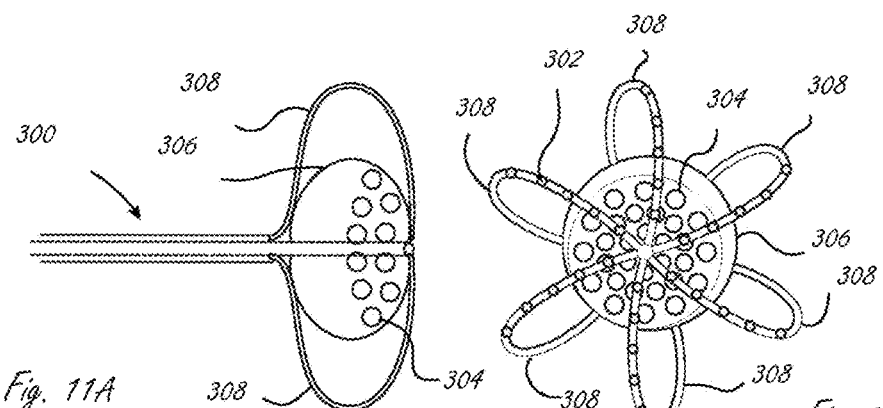
FIGS. 11A and 11B illustrate an exemplary ablation catheter adapted with mapping structures or adapted to be used with mapping structures.
Figures 12A, 12B:
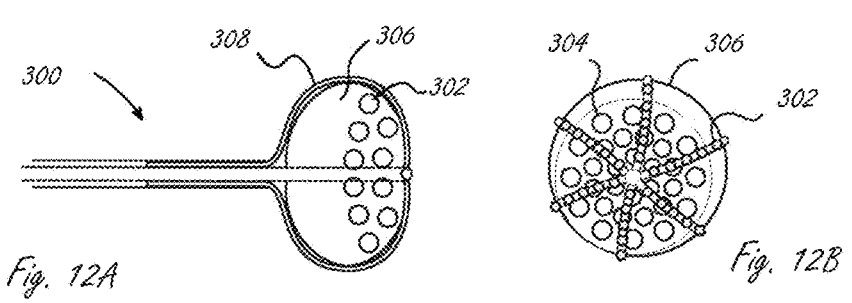
FIGS. 12A and 12B illustrate an exemplary ablation catheter adapted with mapping structures or adapted to be used with mapping structures.

FIGS. 11A and 11B depict an exemplary ablation catheter 300 that includes an array of mapping electrodes 302 (only one is labeled for clarity) carried on the surface of a plurality of reconfigurable mapping arms 308. FIG. 11A is a side view and FIG. 11B is a distal view. Arms 308 together have a "basket" configuration and are disposed outside of the inflated membrane 306. In FIGS. 11A and 11B arms 308 are in their expanded configurations, after being released from within the delivery catheter. Arms 308 are collapsed into the space between the delivery catheter and the ablation catheter 300 during delivery and retrieval, and are adapted to self-expand on release by retraction of the delivery catheter or delivery past the distal end of the delivery catheter. Six arms 408 are shown, each with a plurality of electrodes 302, but more or fewer arms of the basket can be included. The arms can all be secured to the same mapping basket hub (or made from a single piece of material), or they can be secured independently to the ablation catheter. FIGS. 11A and 11B show catheter 300 with arms 308 in retracted positions in with proximal ends of arms 308 are retracted and positioned between the delivery catheter and the ablation catheter. Arms 308 are closer to the surface of expanded membrane 306 than in the expanded configurations shown in FIGS. 11A and 11B.

Figure 13:
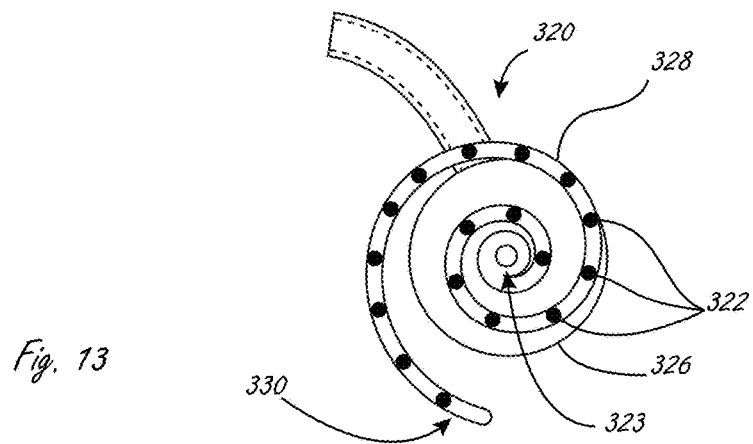
FIG. 13 illustrates an exemplary ablation catheter adapted with mapping structures or adapted to be used with mapping structures.

FIG. 13 is a distal view of a distal end of an exemplary ablation catheter 320. In this embodiment the ablation catheter includes an alternative spiral structure 328 that carries a plurality of mapping electrodes 322 (only three are labeled). The spiral mapping structure can be adapted to be delivered through the guidewire lumen 323, or it can be adapted to be expanded from between the delivery catheter and ablation catheter shaft, similar to the embodiment in FIGS. 11A and 11B. In the embodiment in FIG. 13 in which the spiral structure is adapted to be delivered via a guidewire lumen, the spiral, in a side view, can be in a single plane, or the spiral can have a conical configuration that is adapted to be deformed into a single plane when the spiral is pushed distally into contact with tissue. Ablation electrodes are not labeled on the ablation balloon for clarity on FIGS. 13-17.

Figure 14A:
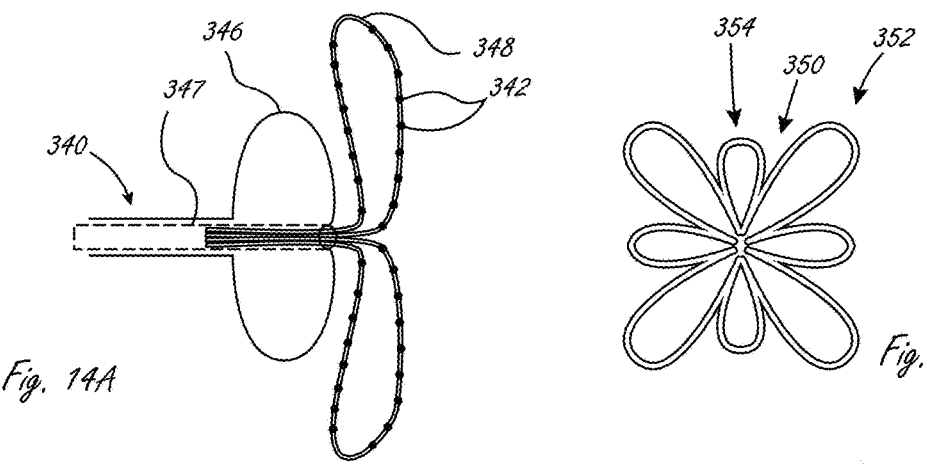
FIGS. 14A and 14B illustrate an exemplary ablation catheter adapted with mapping structures or adapted to be used with mapping structures.
Figure 14B:
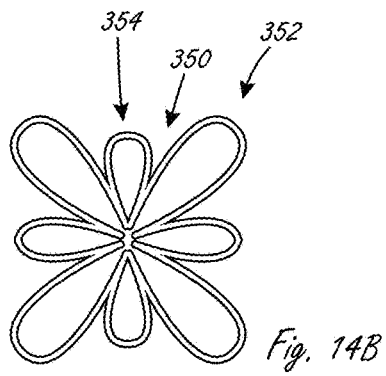

FIG. 14A is a simplified side view illustrating an alternative ablation catheter 340 with a dedicated mapping structure 348 with a plurality of mapping electrodes 342 (only two are labeled) thereon. In this embodiment the two mapping arms 348 have expanded loop configurations as shown and are adapted to be delivered through guidewire lumen 347 as shown. There may be more or fewer than two arms. FIG. 14B is a distal view of an alternative embodiment in which the mapping structure 350 includes a plurality of loops in their expanded configurations. In this embodiment at least one loop 352 has an expanded "height" (a distance measured from the longitudinal axis of the catheter along a line perpendicular to the axis) greater than a height of a second loop 354. In particular, there are four arms 352 with a first height greater than a height of four other arms 354. There can any number of loops of varying height dimension.

Figure 15:
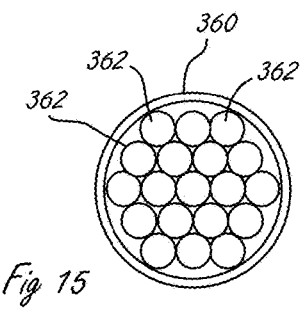
FIG. 15 illustrates an exemplary configuration of mapping arms and electrodes in collapsed configurations within a guidewire lumen.

FIG. 15 illustrates an exemplary configuration of mapping arms and electrodes 362 in collapsed configurations within guidewire lumen 360, and is merely illustrative to show how a plurality of arms can be disposed within a guidewire lumen. More or fewer arms can be disposed therein.

Figure 16:
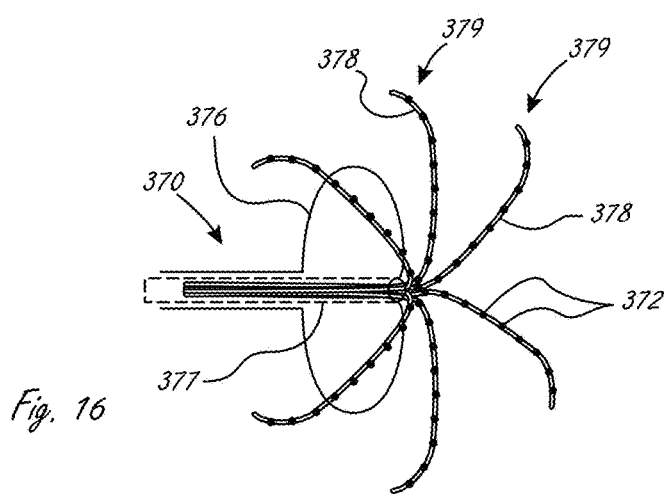
FIG. 16 shows a simplified side view of an exemplary ablation catheter in which the mapping arms terminate at their respective distal ends.

FIG. 16 shows a simplified side view of an exemplary ablation catheter 370 in which the mapping arms 378 terminate at their respective distal ends 379. That is, each arm has a free end. Catheter 370 includes balloon 376, guidewire lumen 377, mapping electrodes 372 on arms 378, similar to other embodiments herein. Any of the described mapping arms may comprise a stiffening member such as NiTi wire such that on release the mapping member takes on a predetermined shape.

Any of the mapping arms that are delivered through the guidewire lumen can alternatively be configured for delivery in the space between the ablation catheter and the delivery catheter, and vice versa.

In yet other embodiments the mapping arms may be woven into a conical braid or braid structure which increases in diameter as it extends distally.

Figure 29:
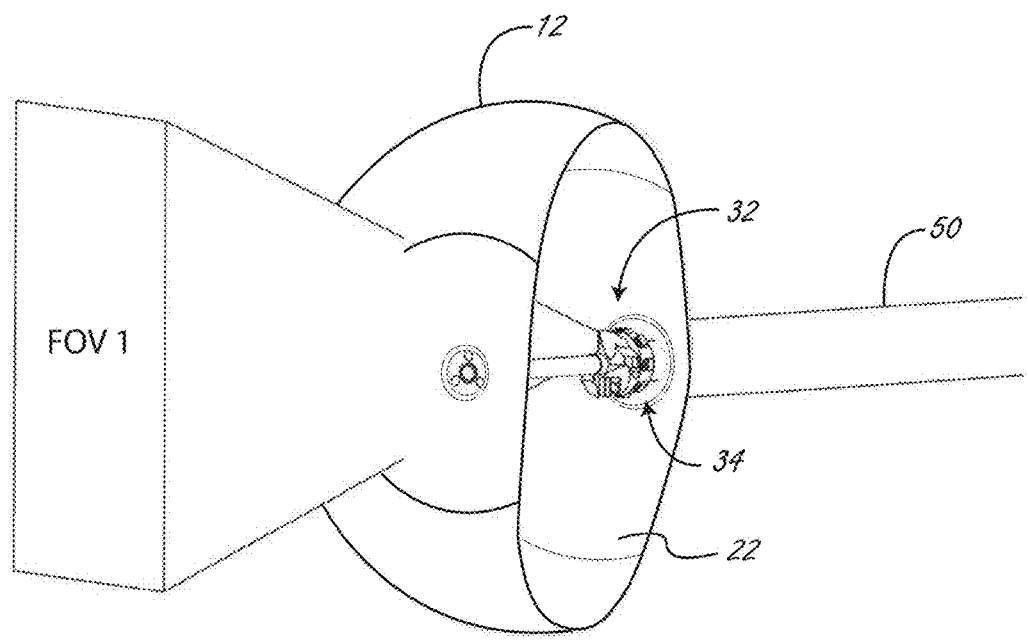
FIG. 29 illustrates only one of the four fields of view for one of the four cameras in the camera assembly.
Figure 30:
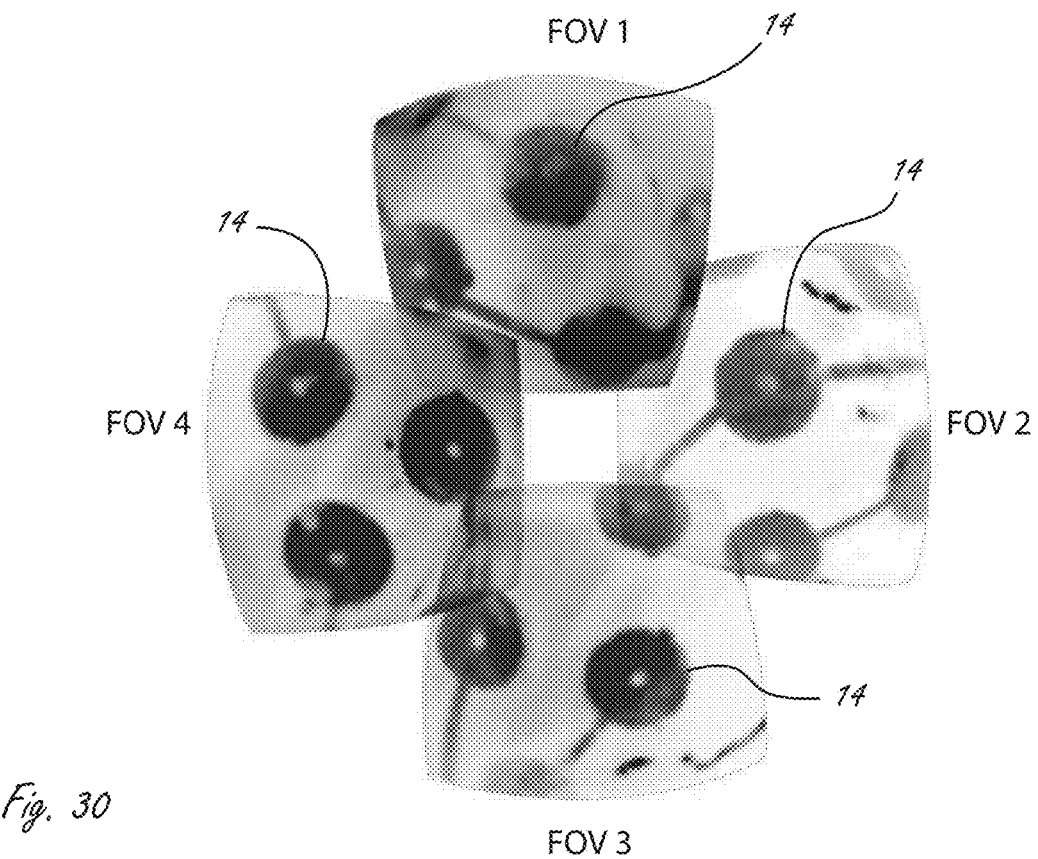
FIG. 30 illustrates the four fields of view from the four cameras, each overlaid with at least one other field of view, to give the physician a 360 degree view.

In use, the optional visualization system allows for real-time visualization of the procedure with a view by one or more cameras disposed within the balloon. The visualization allows for the entire procedure to be visualized, allowing physicians to assess the degree of tissue contact, and see the electrodes, tissue, and lesion formation as it occurs. For clarity, FIG. 29 illustrates only one of the four field of views for one of the four cameras in the camera assembly. FIG. 30 illustrates the four field of views from the four cameras, each overlaid with at least one other field of view, to give the physician a 360 degree view (with the longitudinal axis of the catheter as the reference) of the treatment area. While there is a blind spot shown in the center of the four images, different lensing systems than those used in the current embodiments can allow for elimination of that spot. Since there are electrodes disposed around the entire catheter, the 360 degree view allows the physician to visualize an entire lesion that utilizes electrodes disposed around the catheter. The visualization of the entire procedure including lesion formation at any of the electrode locations is immensely helpful to the physician.

The description herein of overlaying camera field of views is related to the disclosure in U.S. Pub. No. 2012/0071870, in particular FIGS. 38H-38R, and the textual descriptions thereof. One aspect of this disclosure is an exemplary method of generating a panoramic image display using images from a plurality of cameras attached to an endoscopic catheter. In some embodiments a plurality of images captured from a plurality of cameras are overlayed with at least one other image to create the panoramic image around the longitudinal axis of the ablation catheter. Two or more cameras can image various sections of the expandable member (from within the expandable member) and the anatomy, and the geometric relationships between the cameras are either known a priori (by design or measurement), or can be estimated from the images themselves using common anatomical features of the balloon as landmarks.

In general, for each camera, a mapping function that maps a pixel into a virtual unwrapped display screen, e.g. a dome-shaped screen, surrounding the cameras is computed. The images are then projected back to this virtual display screen using inverse projection, i.e., using cameras as projectors. Data in overlapping regions are combined using compositing including blending or some other means.

FIG. 17 is a side view of a distal portion of an exemplary visualization catheter. FIG. 17 shows the geometry of the distal portion, which includes four cameras attached to the distal end of the central shaft of the catheter, surrounded by a membrane filled with saline. Each camera is imaging a section of the closed membrane from within the membrane. The conical shape shown in FIG. 17 represents the field of view of one of the plurality of cameras. In this embodiment, while not shown in FIG. 17, a plurality of radio frequency electrodes are secured to the exterior of the membrane. When the distal portion is positioned inside a cardiac chamber such as the left atrium, the cameras are able to visualize blood or tissue outside the balloon as well as the inner surface of the balloon. This provides a way to verify that the electrodes are in contact with tissue prior to starting the ablation and the balloon is located properly relative to anatomical landmarks such as a pulmonary vein.

FIGS. 18A-18D show the orientations of the axes of the four cameras in relationship to the longitudinal axis of the catheter shaft. Arrows AP, BQ, CR and DS shown in FIG. 18C represent the axes of the respective cameras. OM is the longitudinal axis of the catheter shaft. The parameter "c" is the shortest distance between the axis of the catheter shaft OM and an axis of a camera (see FIG. 18A). The camera axis is also at an angle $\phi$ relative to the axis of the catheter shaft OM (see FIG. 18B). The distal surface of the membrane can be modeled as an elliptical solid of revolution, as shown in the side geometrical view of FIG. 18D. Parameters a and b define the ellipsoid. The equator of the ellipsoid, as labeled in FIG. 18D, is at a distance "d" from the point "O" shown in FIG. 18D. The imaging plane of the camera with the axis CR is at a distance e from C, as shown in FIG. 18D.

Figure 19:
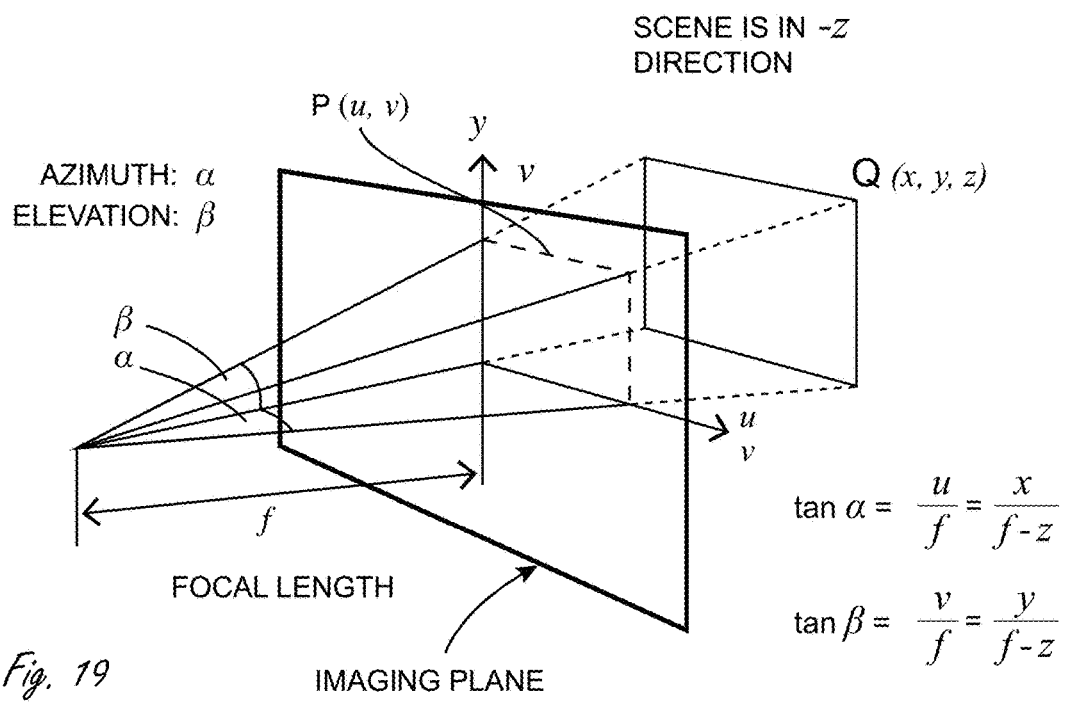
FIG. 19 shows the geometry of one of the four cameras, and all four have the same geometry.

FIG. 19 shows the geometry of one of the four cameras field of view, and all four have the same geometry. A pixel in the imaging plane, P(u, v), is related to a point Q(x, y, z) in space by equations (1) and (2), where f is the focal length of the camera.

$$\frac{u}{f} = \frac{x}{f-z} \tag{1}$$

and $$\frac{v}{f} = \frac{y}{f-z} \tag{2}$$

Figure 20:
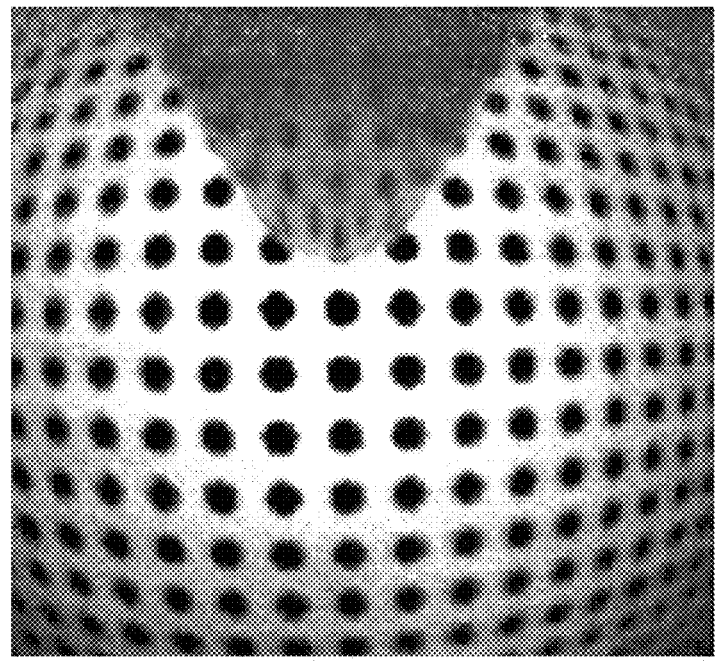
FIG. 20 shows a picture of a regular grid pattern target taken by a representative camera.

Furthermore, the image captured by the camera can have lens barrel aberration. FIG. 20 shows a picture of a regular grid pattern target taken by a representative camera. As can be seen, barrel aberration causes the grid points farther away from center 390 to appear smaller and compressed to each other.

The mapping function that maps the original pixel coordinates, P(u, v), to a distorted pixel coordinate system due to barrel aberration, $\tilde{P}(\tilde{u}, \tilde{v})$, can be determined by using the grid target:

$$\begin{bmatrix} \tilde{u} \\ \tilde{v} \end{bmatrix} = \begin{bmatrix} F(u) \\ G(v) \end{bmatrix} \tag{3}$$

Figure 21A:
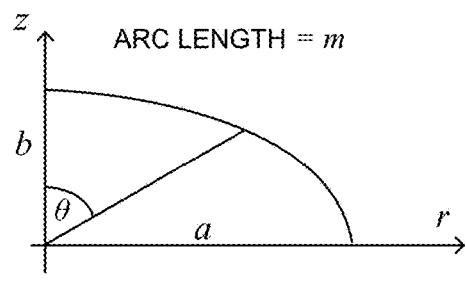
FIGS. 21A-21C show parameterization that can be used to unwrap the 3D surface of the ellipsoidal balloon into a 2D plane.
Figure 21B:
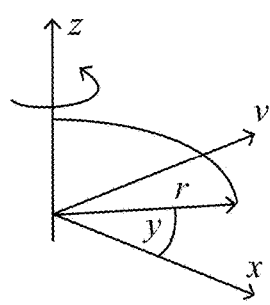
Figure 21C:
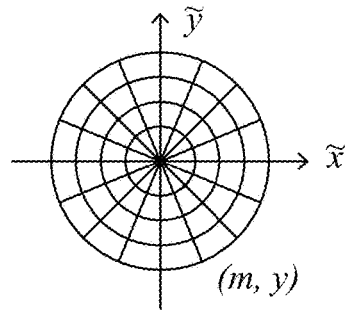

The 3D surface of the ellipsoidal balloon can be unwrapped into a 2D plane using the parameterization shown in FIGS. 21A-21C. In FIG. 21A, the parameters of a and b describe the balloon as an elliptical solid of revolution. The parameter m corresponds to the arc length along the balloon surface, starting from the zenith. In FIG. 21B the rotation angle γ describes the azimuthal angle of the solid of revolution. In FIG. 21C, the unwrapped balloon surface is defined by the parameters (m, γ) in polar coordinates or ($\tilde{x}$, $\tilde{y}$) in rectilinear coordinates.

A point on the balloon surface can be: (x, y, z). A planar unwrapped image can be constructed from the ellipsoidal balloon geometry by unwrapping the balloon surface as follows:

$$\begin{bmatrix} x \\ y \\ z \end{bmatrix} = \begin{bmatrix} a\sin\theta\cos\gamma \\ a\sin\theta\sin\gamma \\ b\cos\gamma \end{bmatrix} \tag{4}$$

Where:

$$\theta = g(m) \tag{5}$$

and g(m) is the well-known "Complete Elliptic Integral of the Second Kind." The unwrapped 2D surface is defined by the polar coordinates: (m, γ) or in rectilinear coordinates, ($\tilde{x}$, $\tilde{y}$), where:

$$\begin{bmatrix} \tilde{x} \\ \tilde{y} \end{bmatrix} = \begin{bmatrix} m\cos\gamma \\ m\sin\gamma \end{bmatrix} \tag{6}$$

In summary, the parameters in Table 1 (below) describe the camera geometry of this multi-camera system.

TABLE 1

| | Parameter | Description |
| --- | --- | --- |
| 1 | a | Ellipsoidal balloon geometry |
| 2 | b | |
| 3 | c | Distance offsets |

TABLE 1-continued

| | Parameter | Description |
|---|---|---|
| 4 | d | |
| 5 | e | |
| 6 | f | Focal length |
| 7 | φ | Camera angulation |
| 8 | F | Barrel aberration mapping function |
| | G | |

Using the parameters of Table 1, the $(\tilde{x}, \tilde{y})$ coordinates of the point on the unwrapped balloon corresponding to each pixel in an image produced by a given camera can be computed. Then the intensity of that pixel can be painted on the unwrapped balloon surface. If more than one camera projects data on to the same location on the unwrapped balloon surface, the data can be combined using any number of exemplary ways, such as blending, maximum value, adaptive blending, alpha blending, weighted averaging, etc. These techniques fall into the general category of "Compositing" as described in Foley et al., "Computer Graphics Principles and Practice", 1990, Addison Wesley, $2^{nd}$ Edition. ISBN 0-201-12110-7. In the overlapping areas of images from two or more cameras, the underlying anatomical structure may be slightly misaligned even after following the above steps to grossly align the image due to inaccuracies in the geometric model. In this case, a given tissue structure may appear twice in the overlapping area, similar to double vision. To address this problem, images can be locally warped by using feature tracking. See U.S. Pat. No. 6,659,953, issued Dec. 9, 2003 to Sumanaweera et al., titled "morphing diagnostic ultrasound images for perfusion assessment," for a description of an exemplary local warping technique.

Figure 22:
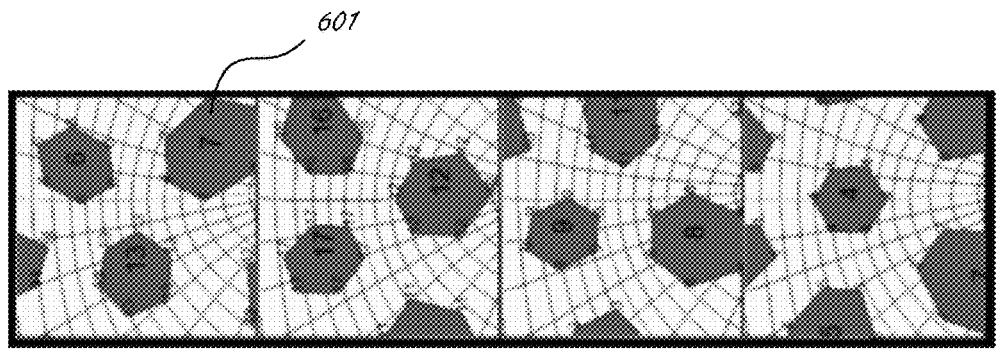
FIG. 22 shows a set of four camera images simulated using a known pattern, in this case, ablation electrodes painted on the membrane.

FIG. 22 shows a set of four camera images simulated using a known pattern, in this case, ablation electrodes 601 painted on the membrane. Electrodes 601 can be in the pattern of the eighteen electrodes shown in FIGS. 1A-1D. Electrodes 601 also have an identifier associated with them, in this case a unique alphanumeric character.

Figure 23:
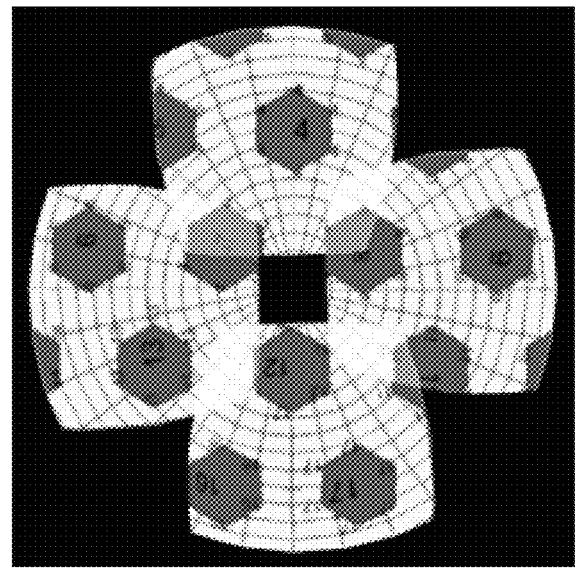
FIG. 23 shows the panoramic image generated by projecting the images from FIG. 22 back onto the unwrapped balloon surface using the methods described above.
Figure 25:
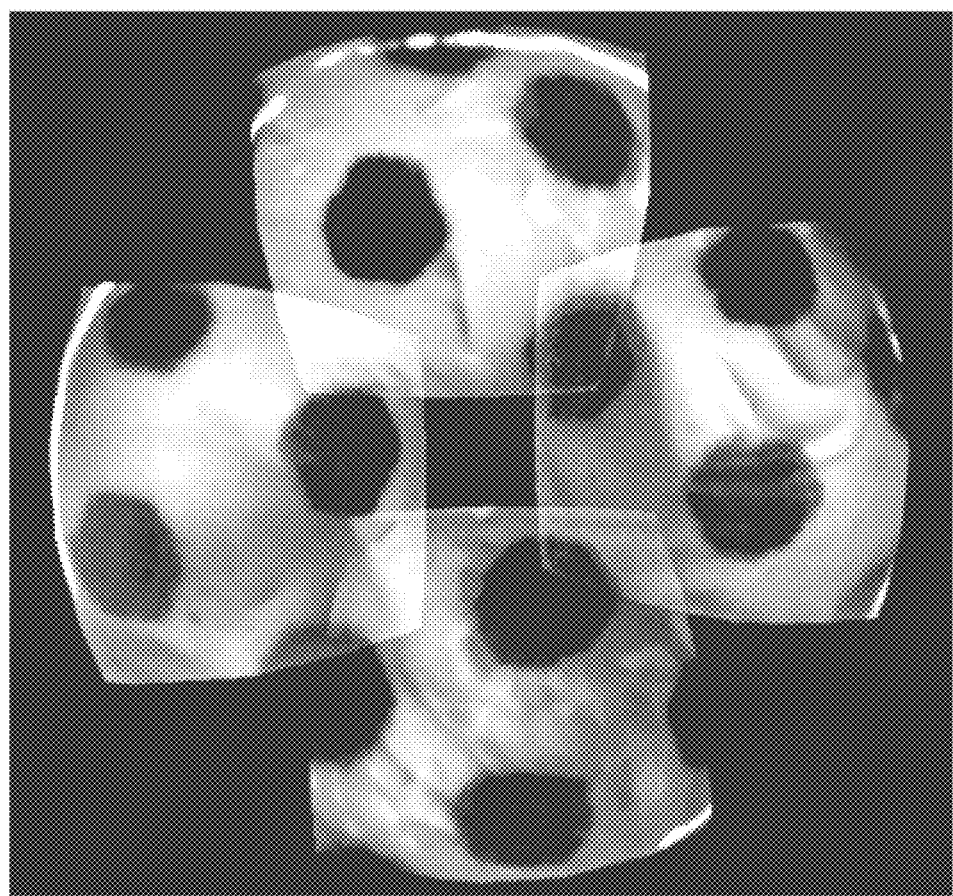
FIG. 25 shows tissue images acquired by four cameras using the methods described herein.

FIG. 23 shows the panoramic image generated by projecting the images from FIG. 22 back onto the unwrapped balloon surface using the methods described above. FIG. 25 also illustrates exemplary electrode identifiers in the form of numbers printed on each electrode to enable visual identification of each of the electrodes. FIG. 25 also illustrates how the collected images comprise common regions to images that are positioned adjacent to them, and that the common regions are overlapped to create the panoramic image.

Figure 24:
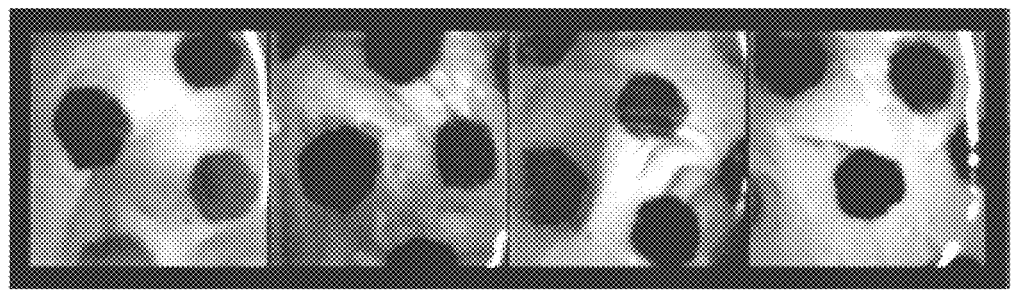
In FIG. 24 the panoramic image is generated by projecting the component images back onto the unwrapped balloon surface.

In FIG. 24 the panoramic image is generated by projecting the component images back onto the unwrapped balloon surface, but the electrodes 370 do not have electrode identifiers associated with them. FIG. 25 shows tissue images acquired by four cameras using the methods described above. FIG. 25 shows the panoramic image generated by projecting these images back onto the unwrapped balloon using the present invention.

The exemplary method above acquires an image from each of a plurality of cameras, and combines the images to produce a panoramic image. As set forth above, the images from each camera can be deformed using a geometric transformation. The deforming can comprise information associated with the known geometric relationship between the cameras. The deforming procedure can comprise geometric transformations generated using compositing in the overlapping areas of the images. The procedure can comprise the use of weighted averaging. The procedure comprises alpha blending. The deforming procedure can comprise geometric transformations generated using feature tracking in the overlapping areas of the images. The characterization of the geometric relationship between the cameras can comprise the use of experimentally determined optical targets. The geometric relationship can be determined analytically by geometrically modeling the cameras, the fixture containing the cameras and the balloon. The geometric transformation can include geometric transformations that map the balloon onto a planar surface while maintaining the distance between any arbitrary set of points on the 3D surface.

One aspect of this disclosure is an electromechanical device providing for the continuous or semi-continuous adjustment of the transfer of AC power from a source to a load by means of linearly displaceable core. The electromechanical device can be used with any of the ablation catheters herein. An understanding of the operation of a linear variable differential transformer ("LVDT") assists in the discussion of this aspect of the disclosure. An LVDT is comprised of a primary center coil winding connected to an AC signal source and one or two "secondary" coil windings connected in series to a load. A ferromagnetic core couples the magnetic field at the primary coil to the secondary coil(s) thereby creating a voltage differential across the coils which changes in magnitude with core displacement.

This aspect of the disclosure is a derivative of the LVDT sensor having only a single primary and single secondary coil with a displaceable core. This derivative, called a linear displacement power transformer ("LDPT"), provides a means to transfer power from a primary coil to a secondary coil by means of core position. When the core exists across both coils, maximum (power) coupling occurs between primary ("P") and secondary ("S") coils. As the core is displaced out of the "P" or alternatively out of "S," the coupling is reduced along with the power transfer.

Figure 26A:
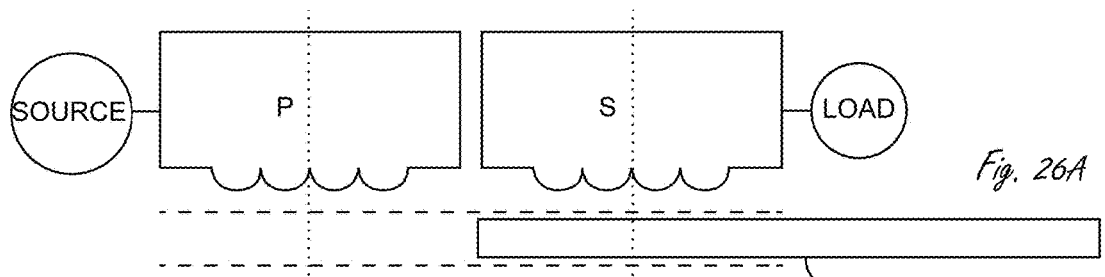
FIGS. 26A-26C illustrate an electromechanical device providing for the continuous or semi-continuous adjustment of the transfer of AC power from a source to a load by means of linearly displaceable core.
Figure 26B:
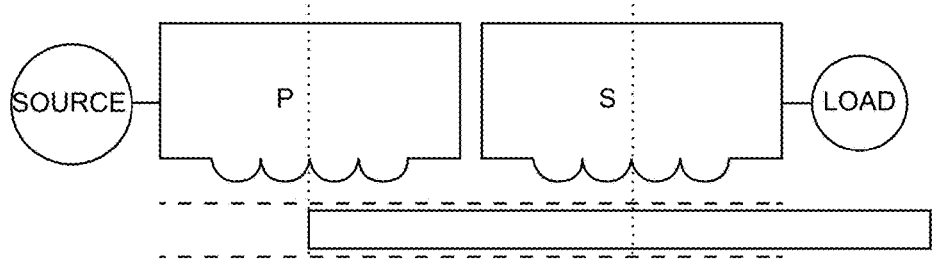
Figure 26C:
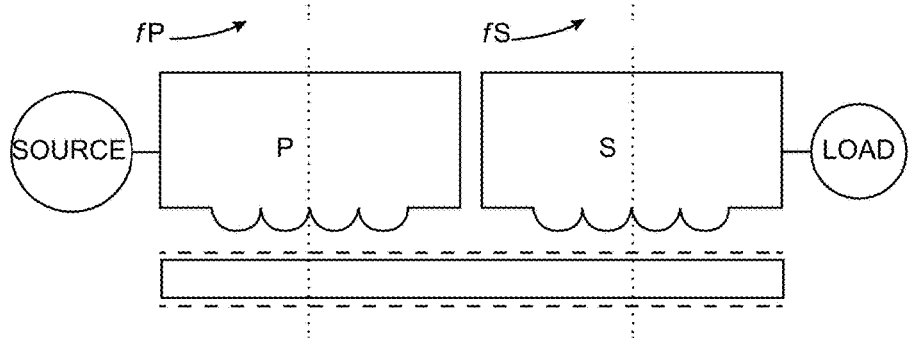
Figure 27:
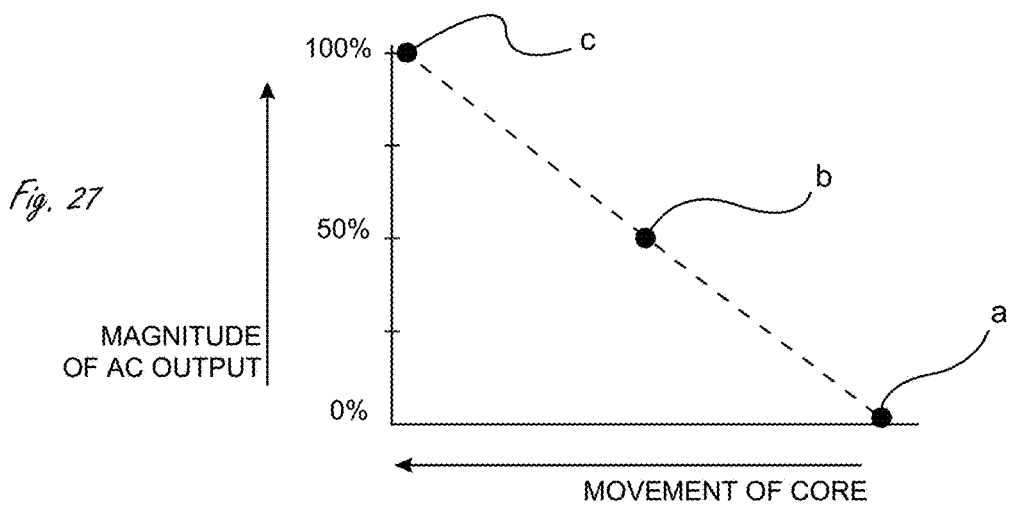
FIG. 27 shows a graph illustrating movement of the core versus magnitude of AC output.

FIGS. 26A-26C provide an illustrated schematic of this aspect. In FIG. 26A ferromagnetic rod core 101 is aligned with a secondary coil "S" but not a primary coil "P," a decoupled state resulting in minimal current output as charted on the graph of FIG. 27. FIG. 26B shows the rod core displaced to partially align with coil "P" at a theoretical halfway point somewhat coupling fields fP and fS to produce a theoretical current output of 50% percent maximum. FIG. 26C shows the rod core displaced into alignment with coils "P" and "S" fully coupling fields fP and fS providing maximum current output to the load.

Figure 28A:
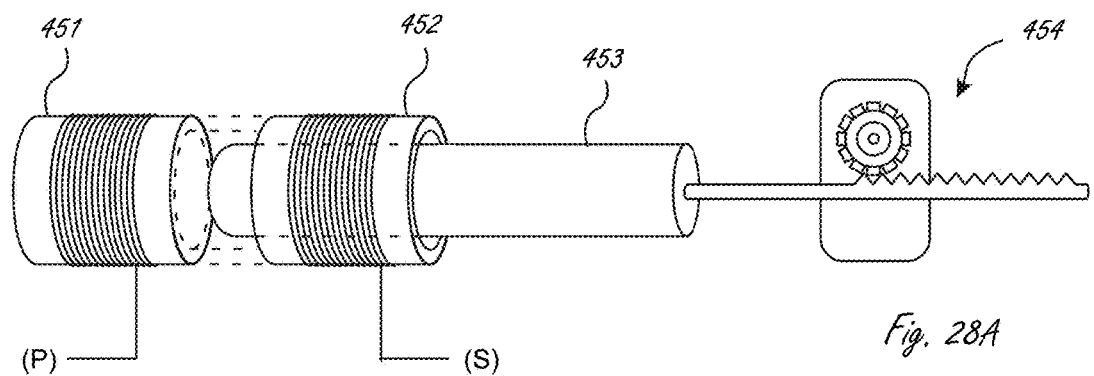
FIGS. 28A and 28B represent one embodiment of where a core is displaced by a micro-stepper motor and screw mechanism.
Figure 28B:
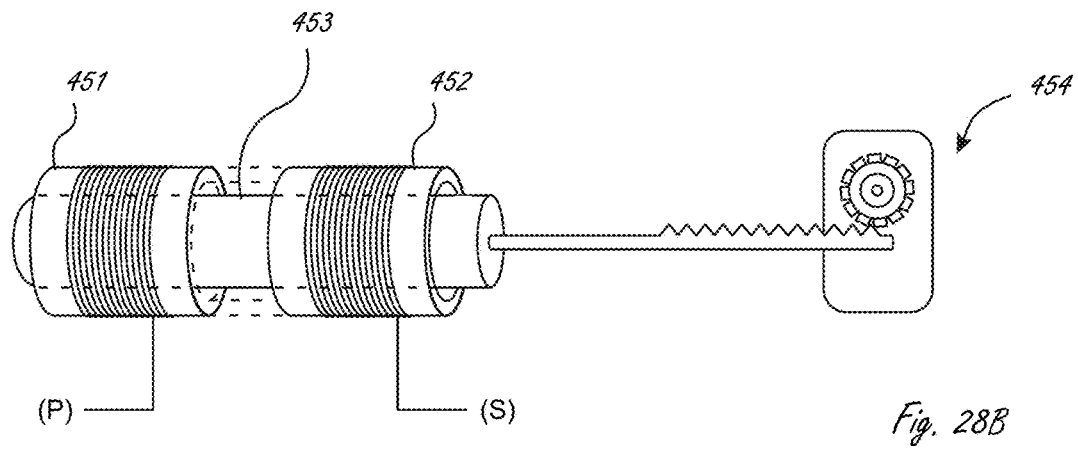

FIGS. 28A and 28B represent one embodiment of this aspect where core 453 is displaced by a micro-stepper motor and screw mechanism 454. Primary winding 451 and secondary winding 452 are wound radially along a common axis through which core 453 may be displaced. FIG. 28A shows the LDPT in a minimal output position and FIG. 28B shows the LDPT in a maximal output position. The power transfer is electrically noiseless and the use of a ferrite rod core minimizes eddy current loss.

Such a variable transformer is of particular use in a treatment system requiring a multichannel, low noise, linear RF power distribution system. In such linear RF power distribution systems, an LDPT can be comprised in each output channel, a selection of output channels, or alternatively as the power source to all of the channels.

Such treatment systems are of particular use in providing percutaneous ablation treatments such as for the treatment of atrial fibrillation as set forth herein.

One aspect of the disclosure is an assembly that includes a primary winding, secondary winding, a ferromagnetic core, a way to linearly move the ferromagnetic core, where the windings are positioned coaxially, a ferromagnetic rod movable along the coaxial axis, wherein the ferromagnetic rod is adapted such that it can be positioned adjacent to both windings simultaneously, and wherein the ferromagnetic rod is adapted to be positioned adjacent to only one winding. The ferromagnetic core can be displaced by a stepper motor and screw mechanism.

One aspect of the disclosure Is a method of adjusting output power to an RF electrode by moving a ferromagnetic core within a transformer comprised of two windings. One aspect of the disclosure is a method of adjusting power to an RF electrode by moving a ferromagnetic core within a transformer. In either method the RF ablation electrode is percutaneously delivered to a treatment site within a living being.

In an exemplary method of use, the catheter is used to ablate cardiac tissue in the treatment of a cardiac arrhythmia. The catheter is advanced into the left atrium using known access procedures including guide wire and guide catheter techniques. Inflation/irrigation fluid is then pumped from a fluid source down inflation/irrigation lumen 52 to inflate the balloon to the configuration shown in FIGS. 1A-1C within the left atrium. The camera can be activated at any time during the procedure, but generally before inflation so the physician can see if there are any problems with the inflation. At this point the balloon is surrounded by blood, which can be seen. The catheter is advanced distally towards the atrial wall, and as the balloon contacts tissue the blood will be displaced, providing a clear view of the tissue. The physician can then determine if the balloon needs to be moved depending on the desired treatment tissue or desired area to map. An advantage of the visualization system in the devices herein is that the physician can easily see, simply by viewing a display showing the camera field of views, when the balloon is properly positioned. This also simplifies the system in that an analysis of reflected energy need not be performed, as in the case in some previous attempts at cardiac ablation.

Figure 33:
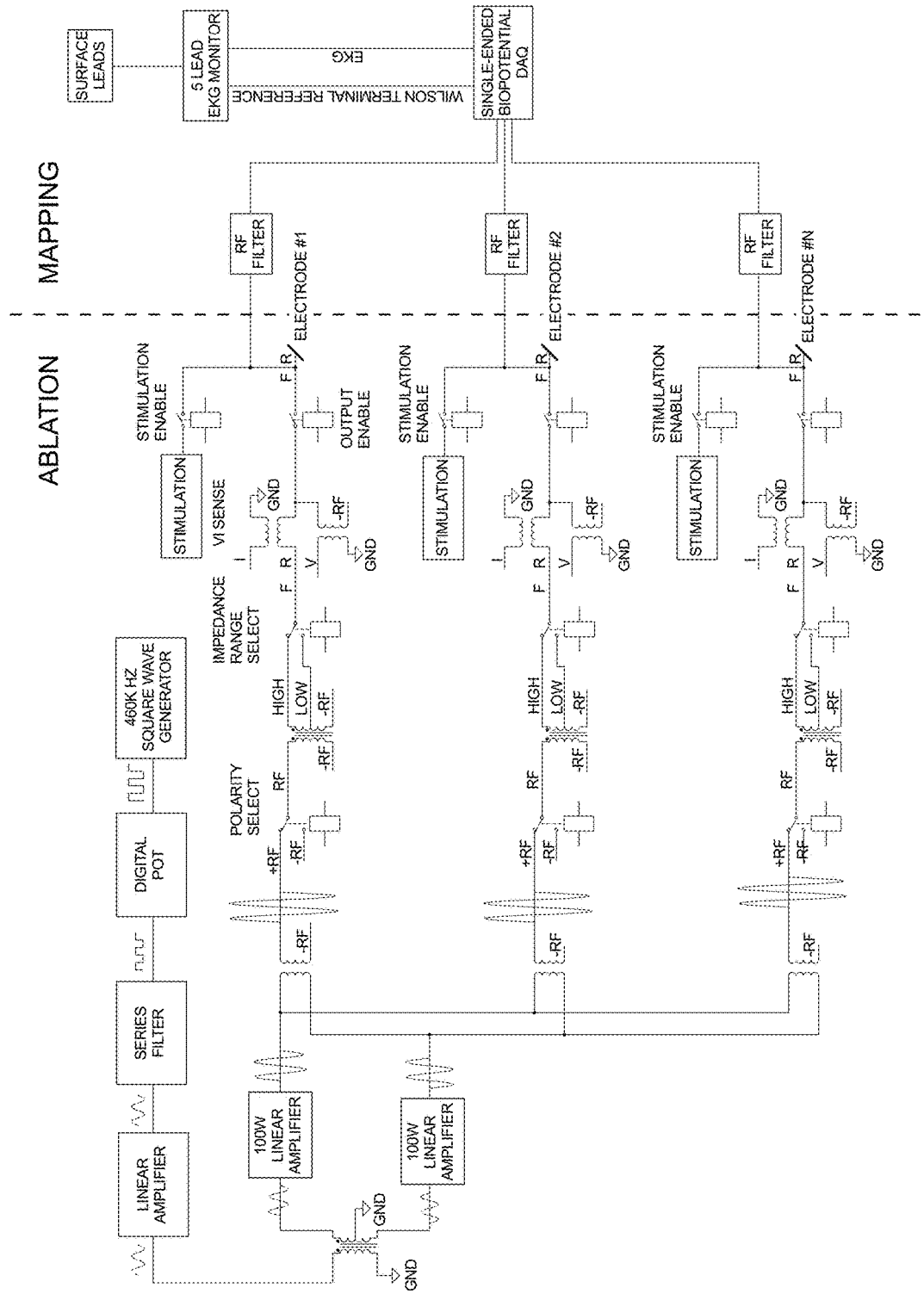
FIG. 33 is an exemplary schematic of the electrical aspect of an exemplary embodiment.
Figure 35:
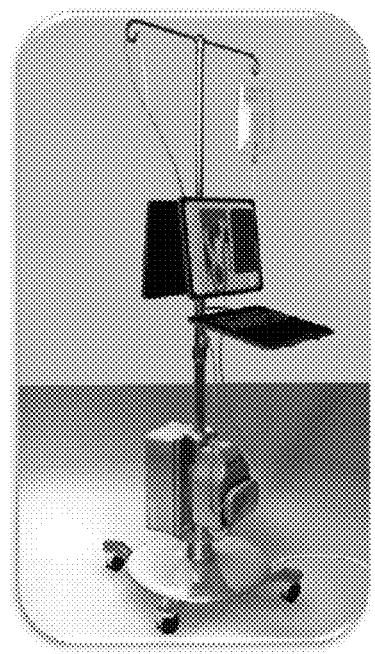
FIGS. 35 and 36 illustrate aspects of an external console.
Figure 36:
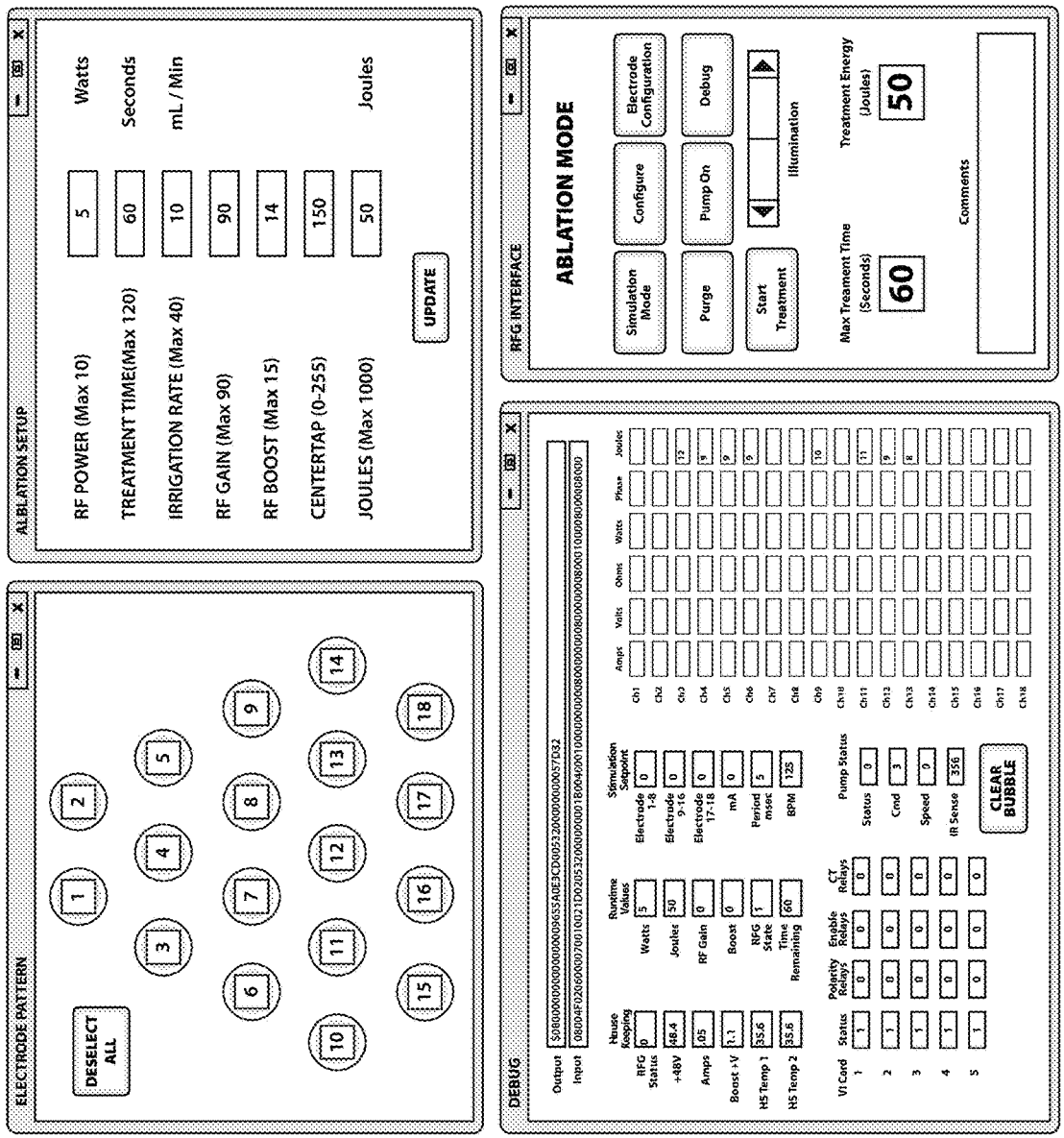

Once it has been determined, depending on the visualization information such as proper placement around a pulmonary vein or mapping electrical information, that the balloon has been properly positioned at the treatment site, an external console, generally shown in FIGS. 35 and 36, is used to activate certain electrodes and control the energy delivery parameters of the procedure. An RF generator generates the RF energy and it is delivered to the electrodes. An exemplary schematic of the electrical aspect of the embodiment shown herein is shown in FIG. 33. It is understood that eighteen channels are included while only three are shown. Alternate embodiments, not shown, may comprise more or less channels. As shown in FIG. 33, the mapping capabilities of the system are shown to the right of the electrode. Each electrode can be used in monopolar or bipolar mode, and impedance and voltage can be measured with each electrode.

The generator is configured such that electrodes can be used to map tissue, ablate tissue, and stimulate tissue, as desired. Ablation of cardiac tissue to treat aberrant signals is described generally herein and known. The generator is also configured, however, to generate and deliver electrical tissue stimulation signals to the electrodes so that the electrodes stimulate the cardiac tissue. The schematic in FIG. 33 illustrates that each electrode can be selected for either ablation or stimulation, while mapping from each electrode occurs continuously. The mapping portion includes filters configured to filter out ablation bandwidths, and other non-essential bandwidths that may be delivered or otherwise present so that mapping can occur continuously. The disclosure herein thus includes a generator configured such that each electrode can be used to both map and ablate tissue at the same time, or stimulate and ablate tissue at the same time. The system is also configured such that ablation, stimulation, and mapping can all be occurring at the same time, although the stimulation and ablation would not be occurring at any given time from the same electrode. These processes in addition can be performed sequentially.

Stimulation of the cardiac tissue can be done for a number of reasons. In an exemplary embodiment stimulation of tissue can be performed during a diagnostics procedure to make sure the electrodes are working. For example, RF energy can be delivered to a first electrode and sensed with another electrode, thereby transferring energy between pairs of electrodes to make sure the pair of electrodes is working. In this exemplary use, the stimulating energy could be delivered before the balloon makes contact with tissue or after it makes contact with tissue, as blood generally has low enough impedance so as not to prevent the diagnostic test. In an alternative embodiment cardiac tissue can be stimulated while tissue is being ablated with other electrodes. For example without limitation, three electrodes could be used to deliver ablation energy to create a lesion between the three electrodes (e.g., a linear ablation), while an electrode on one side of the lesion could be used to deliver stimulating energy to an electrode on another side of the lesion to determine if the tissue is effectively ablated. Exemplary tissue stimulation delivery signal capabilities include currents of 0 to 20 ma, pulse widths of 0 to 100 ms, repetition rates of up to 300 bpm. More preferably 0 to 10 ma, 0 to 10 ms, and up to 180 bpm. Stimulating cardiac tissue in these ways is different than mapping in that mapping measures impedance, while stimulation delivers energy configured to stimulate the cardiac tissue. The disclosure herein therefore includes methods of stimulating cardiac tissue during an ablation procedure, including before the actual ablation, while ablating, or after the ablation has occurred.

Figure 31A:
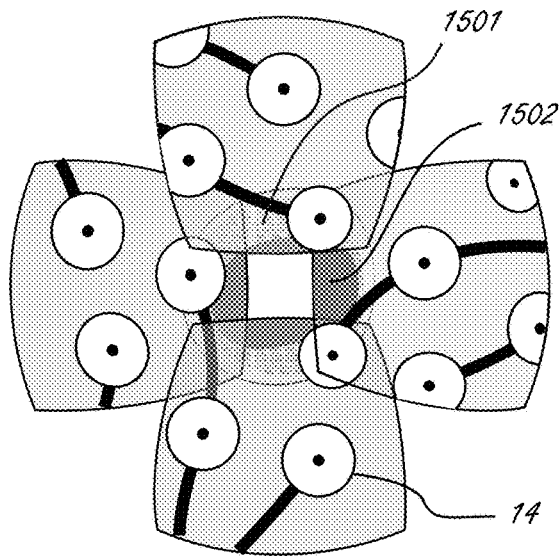
FIGS. 31A-31C illustrate an exemplary method of ablating cardiac tissue.
Figure 31B:
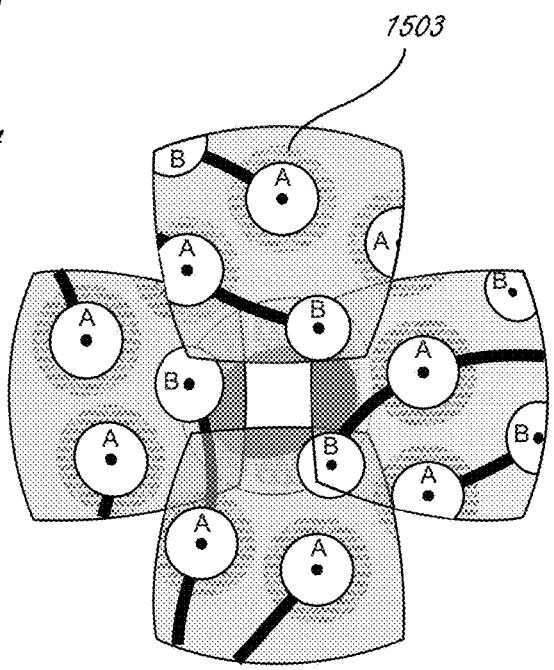
Figure 31C:
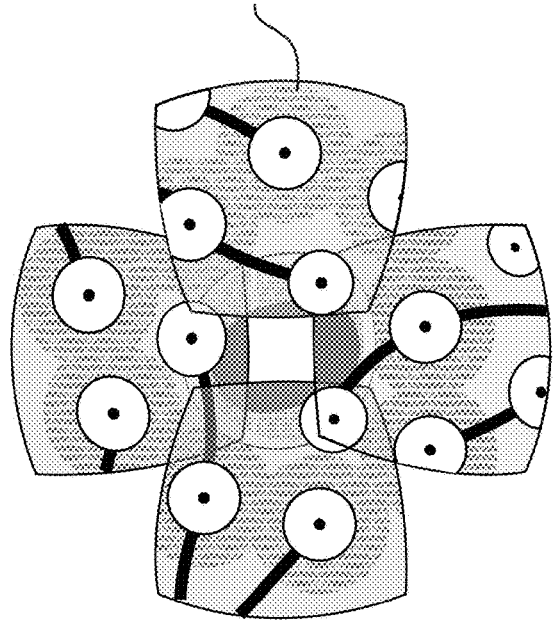

FIGS. 31A-31C illustrate an exemplary method of ablating atrial tissue around a pulmonary vein ostia to isolate the pulmonary vein, and show it from the view generated by the four field of views from the camera. FIGS. 31A-31C are meant to be the view the physician would see when using the system. Again, the blind spot in the middle can be removed depending on the camera assembly and arrangement of cameras therein. In FIG. 31A, the balloon has been advanced into contact with atrial tissue surrounding ostia 1501 of the pulmonary vein lumen 1502. None of the electrodes have been activated in FIG. 31A, although mapping procedures could also take place at this stage to assess the conduction of the cardiac tissue. FIG. 31B show certain electrodes "A" being activated and lesion regions 1503 starting to form in the tissue after the electrodes are making contact and power is applied. Electrodes designated "B" are not being activated in this example. FIG. 31C shows continued ablation of tissue and formation of lesion region 1504 that generally extends around the pulmonary vein ostia.

Figure 32A:
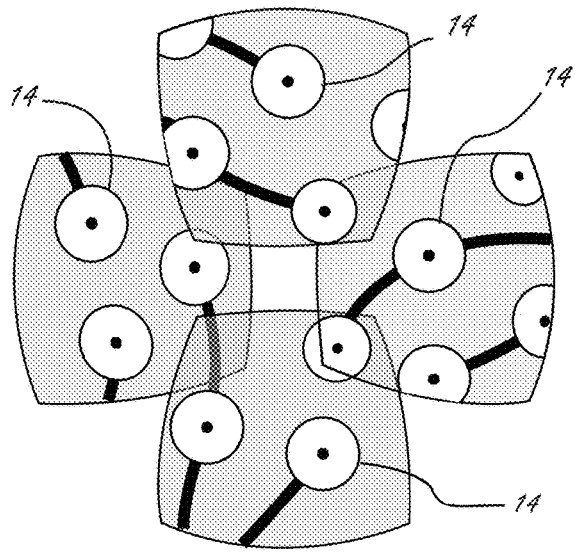
FIGS. 32A-32C illustrate an exemplary method of ablating cardiac tissue.
Figure 32B:
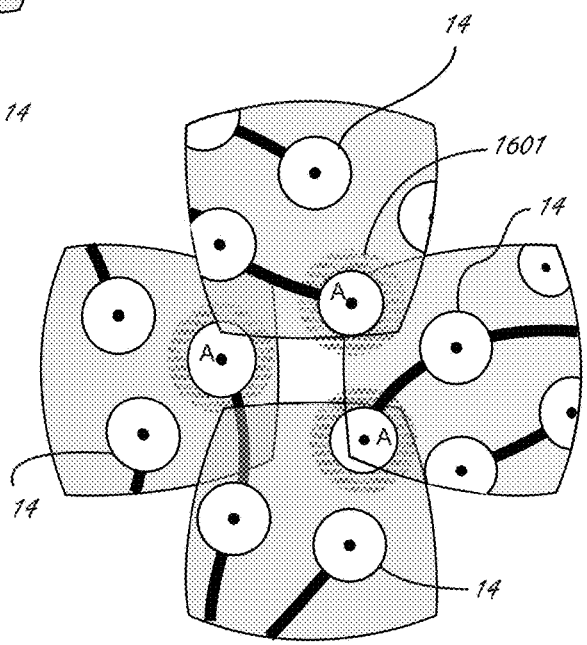
Figure 32C:
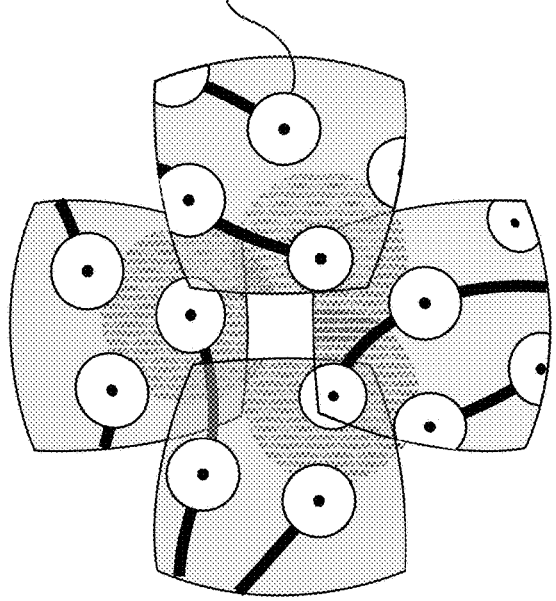

FIGS. 32A-32C illustrate an exemplary method of using the system herein to create lesion for treatment of a rotor. FIG. 32A shows the balloon advanced against cardiac tissue other than an ostia region, where none of the electrodes have been activated. FIG. 32B shows only electrodes "A" being activated, and ablation lesions 1601 starting to form where the electrodes are in contact with tissue and activated. In this embodiment, electrodes A are the distal most electrodes from each of the three flex circuits. FIG. 32C shows continued ablation and the formation of lesion region 1604 targeted at a rotor. The blind spot in the middle hides that the lesion extends over tissue that can't be seen. In alternative embodiments of use, more than three electrodes can be used to perform a rotor ablation, such as four or electrodes.

One aspect of the disclosure is a method of superimposing an image or images provided by the camera with information or an image that is an indication of at least one of a characteristic of the cardiac tissue and a characteristic of the ablation catheter. The superimposed images (or superimposed information and image) are presented to the physician in a visual display, such as a monitor, and can be part of a remote user interface. The aspect includes methods and systems adapted to superimpose images. The methods and devices herein are also adapted to obtain the information and superimpose the images.

The information that is being superimposed can be any suitable visual indicator of a characteristic of the cardiac tissue or a characteristic of the ablation catheter.

In some embodiments the information that is superimposed onto the image from the cameras is the electrical activity on the cardiac tissue contacting the expandable member.

In some embodiments the information that is superimposed onto the image from the cameras is the localized impedance of the ablation circuit.

In some embodiments the information that is superimposed onto the image from the cameras is the temperature of the cardiac tissue opposed to the balloon.

In some embodiments the camera comprising CMOS cameras are adapted to be responsive to light in the infrared range. The response can be used to estimate the temperature of the tissue before, during and or after ablation. The response can be interpreted by an algorithm and displayed superimposed to the visual light image from the cameras.

In some embodiments an accelerometer is placed at a location in, on or near the ablation balloon. The accelerometer can be used to detect the orientation of the balloon in relation to gravity. The accelerometer can produce acceleration data that is used to determine the accelerometer position in relation to an initial position. The position can be used to construct a database of locations visited by the balloon and/or information collected by the electrodes on the balloon and/or RF power applied to the balloon electrodes. The collection of information can be used to reconstruct a model to provide guidance to the physician in relation to the locations that are treated and locations that need to be treated.

Figure 38:
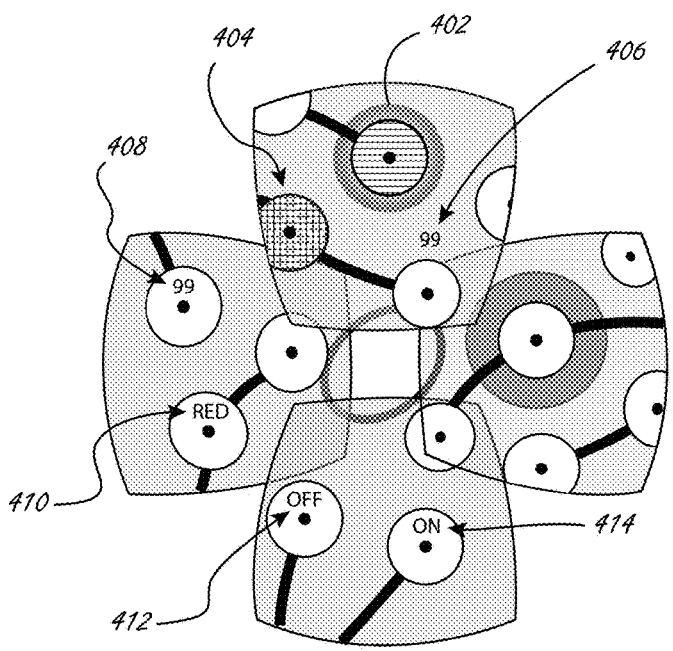
FIG. 38 illustrates exemplary information and indicators that can be superimposed on the images from the cameras.

FIG. 38 illustrates exemplary information and indicators that can be superimposed on the images from the cameras. Indicators 402 and 404 are examples of way to convey temperature of the tissue adjacent an electrode. For example, indicator 402 is a series of lines indicating qualitatively the temperature, such as "medium." Indicator 404 is a series of intersection lines and can indicate "high" temperature. Any type of visual indicators can thus be used to indicate the qualitative temperature of one or more tissue regions adjacent any of the electrodes.

Superimposed information 406 provides a qualitative indication of tissue temperature, in this example, 99 degrees. Information 406 is next to the image of the electrode, whereas information 408 is information that is on the electrode image. Indicator 410 is a red color superimposed on top of the electrode, providing a qualitative indication of "hot." Information 414 and 416 are superimposed to indicate that the respective electrodes are "on" and "off."

In some embodiments the superimposed information is all the same type of information. For example, each electrode can, at the same time, be superimposed with information indicating the temperature of tissue. In other embodiments, the type of superimposed information can be different for any of the electrodes.

Additional examples of the type of information that can be superimposed include electrical impedance, which can be visualized quantitatively or qualitatively using any of the indicators herein (e.g., color, numbers). Additionally, mapping signals can be superimposed on the camera images as well.

Figure 39:
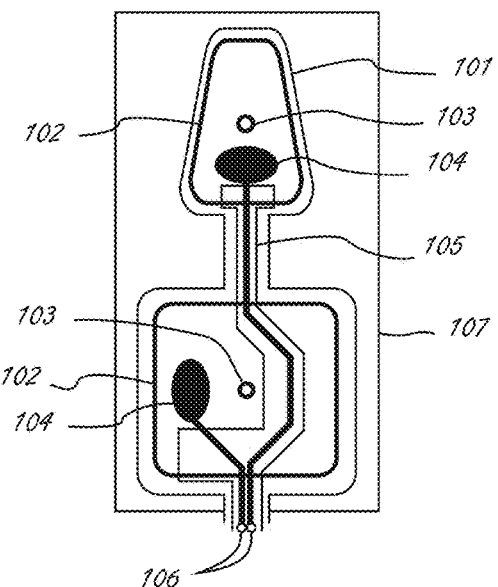
FIG. 39 represents an exemplary flexible circuit for application to the outer surface of a balloon.

FIG. 39 represents an exemplary flexible circuit for application to the outer surface of a balloon, with a thin polyimide substrate 101 approximately 0.002-0.003" thick and a total structural thickness between 0.004-0.006".

The outline is that of the final ablation pads 102 (only the large square and the triangle). Apertures 103 are for saline flow. Circuit traces 104 terminate in exposed areas on the ablation pads. Conductive silver paint is used to create the ablation pad geometry and the exposed trace provides conductivity.

Alternately, a black adhesive may be used to darken the areas under silver painted ablation pads 102 to prevent reflections inside the balloon, as is described herein. One method of employing polyimide substrate 101 can eliminate the black adhesive providing a thinner and more compliant mounting surface.

A dielectric area 105 is provided to prevent cross talk and conductivity to the blood or other medium. The proximal side of the flex circuit has two small solder pads 106 where the wires are attached.

Figure 40:
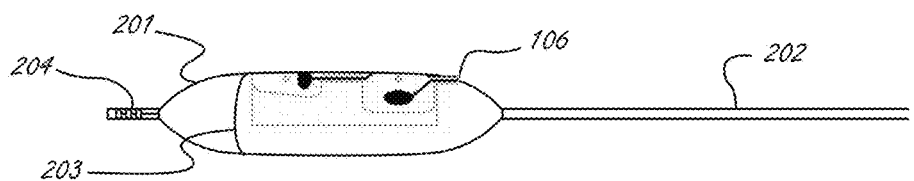
FIG. 40 shows an assembled flexible circuit affixed to a balloon.

An assembled flexible circuit as represented in FIG. 39 can be affixed to balloon 201 as shown in FIG. 40, such balloon being located around a central stem 202, and such stem having a system to capture the image of the internal surface of the balloon (not shown) and transmit such image to a display outside the patient. An optional long protrusion 203 distal to the triangle pad which wraps around the front of the balloon to create a physical anchor for the circuit.

Additionally an accelerometer 204 is placed at a location in, on or near the ablation balloon, such accelerometer can be used to detect the orientation of the balloon in relation to gravity and to construct treatment relevant data sets as described herein.

When the physician moves the catheters as described herein, more specifically, when the physician rotates the system around the longitudinal axis of the catheter, the image display will show the internal surface of the balloon fixed and everything outside the balloon (e.g., cardiac tissue) moving. This is due to the fact that the cameras, in the embodiments herein, are fixed in relation to the catheter and balloon system.

Figure 41A:
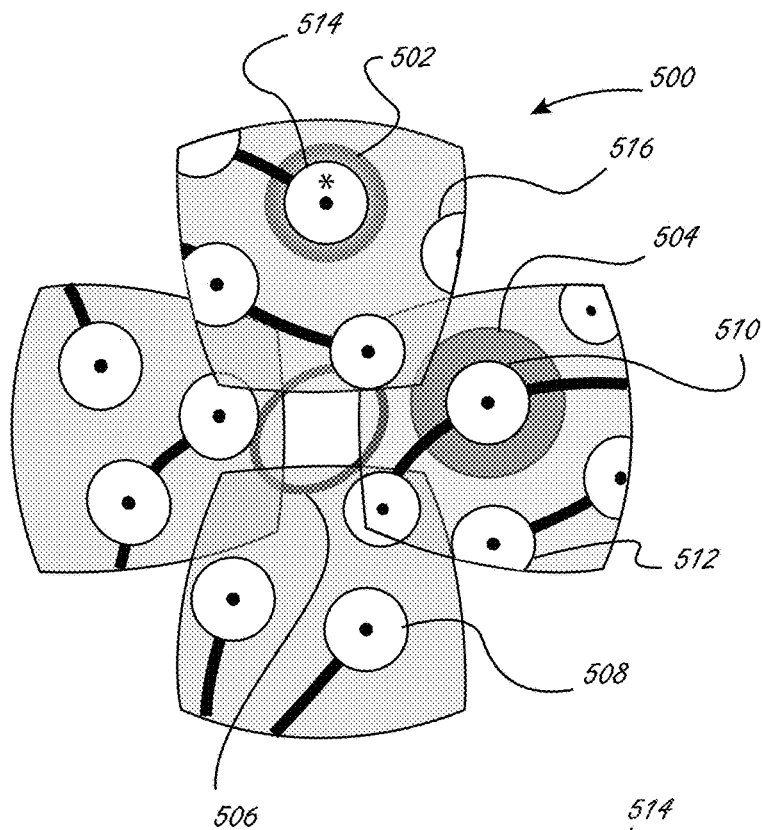
FIGS. 41A and 41B illustrate a composite view as described herein from a four camera array as presented to the user on a display.
Figure 41B:
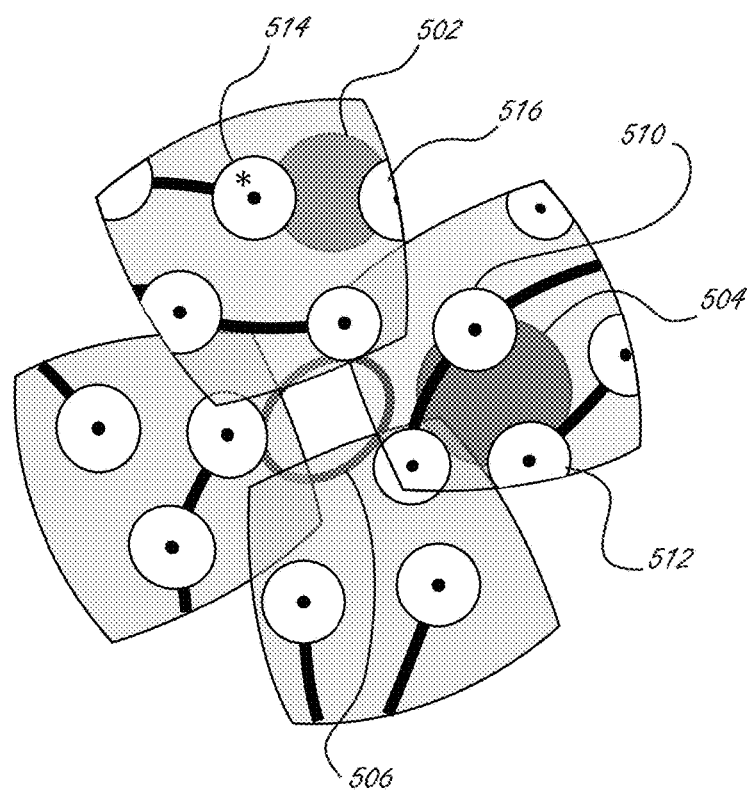

FIGS. 41A and 41B illustrate a composite view as described herein from a four camera array as presented to the user on a display. The images are mapped to a composite image representing the arrangement and orientation of cameras carried by the balloon on the shaft within the balloon. The mapping registration relies on mapping common features within each camera field of view over each other where there are common features within two or more images. As illustrated, one electrode, the orientation registration electrode, is identifiable by a marking in the shape of an asterisk (as shown) which has been printed on the balloon prior to the electrode and is visible to the camera. In other embodiments each electrode may be marked with its own unique identifier or some or all electrodes may have different shapes which help to identify them. The common fixed features (relative to the cameras) include traces, electrodes and other fixed markings. FIG. 41A illustrates an initial image taken just after burns 502 and 504 created by electrodes 514 and 510 respectively. The balloon is centered around a pulmonary vein 506. FIG. 41B illustrates a second image captured by the camera array after the balloon is rotated. Each composite image has been processed such that the fixed features (relative to the cameras) are mapped to the user display in a fashion such that the registration mark (and hence the entire image) is rotated an amount equal and opposite to the rotation measured for the center of mass of one or more of the anatomical features around the center of the composite image such as burns 502 or 504. By so doing the image of the fixed features will rotate while the portion of the image behind the fixed features will remain fixed as the balloon is manipulated.

Disclosed here therefore is a system to, through image processing, show the internal surface of the balloon rotating while maintaining still, or fixed, the image of everything outside the balloon (e.g., tissue). In this manner, the image of everything that is not part of the catheter will remain fixed, and everything that is part of the catheter will be shown in the video to rotate. In this alternate embodiment, the image that the user views shows the fixed features (e.g., electrodes) being rotated while anatomical features remain still. The anatomical features are the non-fixed features or non-balloon related features in the tissue such as, represented in this view, the pulmonary vein, and the images of burns created by ablation. This is accomplished even though the fixed features move as the camera moves. Keeping the tissue fixed for the user, and having the device components move allows the physician to better control the movement of the device relative to the tissue. To facilitate this procedure the mean rotation of the center of mass of one or more of the key anatomical feature are calculated relative to the location of the fixed features. The mean or other suitable representation of the rotation(s) is then used to rotate the composite image as presented on the user display.

Figure 37:
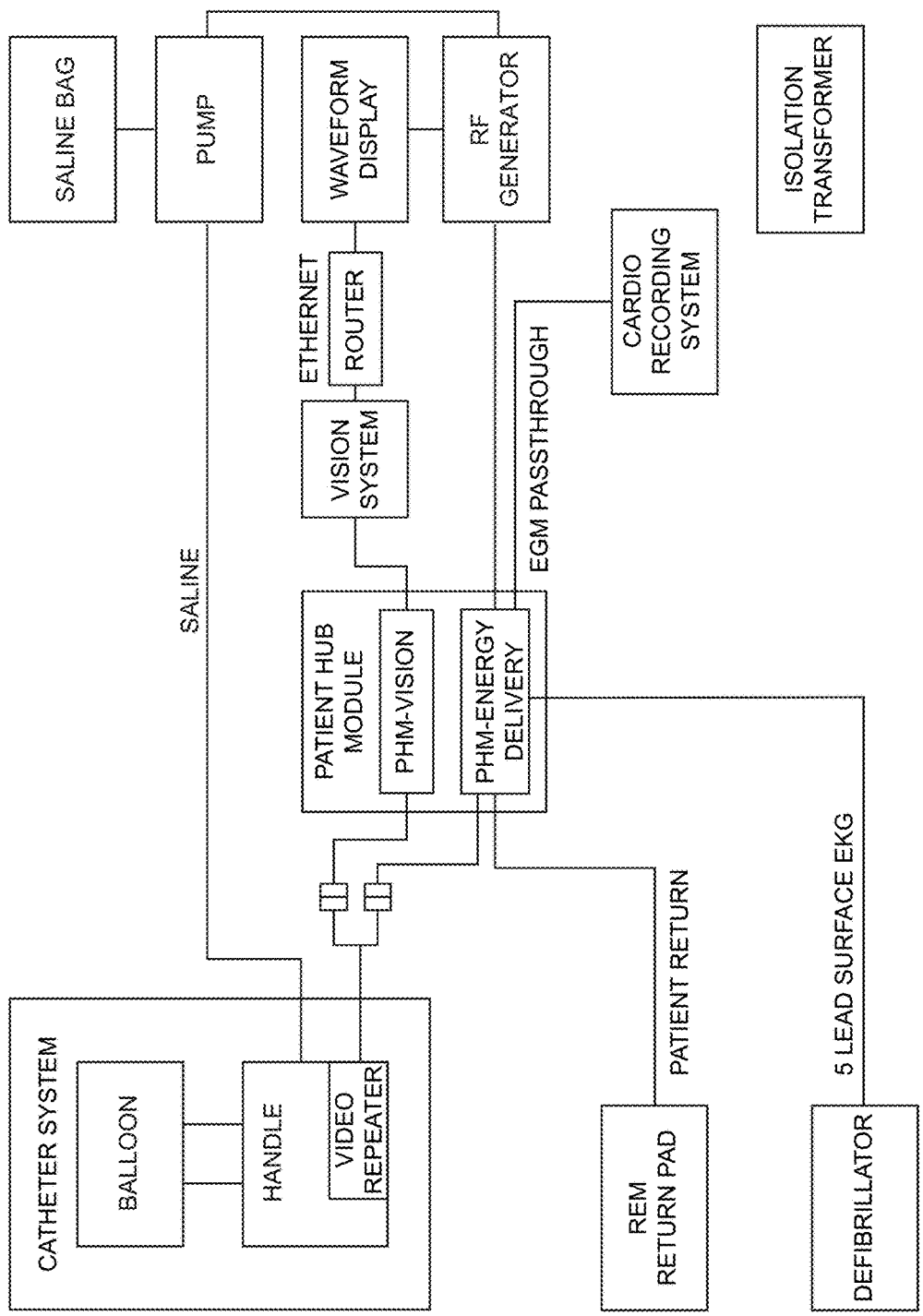
FIG. 37 illustrates an exemplary block diagram of a cardiac ablation system.

FIG. 37 illustrates an exemplary block diagram of a cardiac ablation system, details of which are described herein. Any of the system components in FIG. 38 can be incorporated and used with any of the individual components described herein.

The number and arrangement of the electrodes disposed on the expandable member, each of which is individually addressable and can be used to deliver energy in either monopolar or bipolar mode, provides for a wide variety of lesion formations without having to remove and insert a separate RF catheter. The exemplary methods shown in FIGS. 31 and 32 are merely exemplary. Linear lesions and arc lesions are additional examples of lesion shapes that can be created depending on the desired ablation procedure. In the specific example provided herein, there are eighteen individually addressable electrodes disposed on substantially the distal portion of expandable member 10. Any of them can be energized while others are not, allowing for many different lesion formations to be made in cardiac or other tissue for treating cardiac arrhythmias. Any of the electrodes can be used in bipolar mode with any other electrode as well. Depth and width of lesions may be controlled by choosing and/or varying what combination of electrodes are being used in bipolar and monopolar configurations. Monopolar configuration creates deeper, narrower lesions, and bipolar configuration creates shallower, wider lesions.

One of the advantages of the devices herein is that the number and arrangement of electrodes allow for a wide variety of lesion formations without removing and inserting a new catheter. And the visualization system allows for the entire procedure to be visualized.

Figure 7:
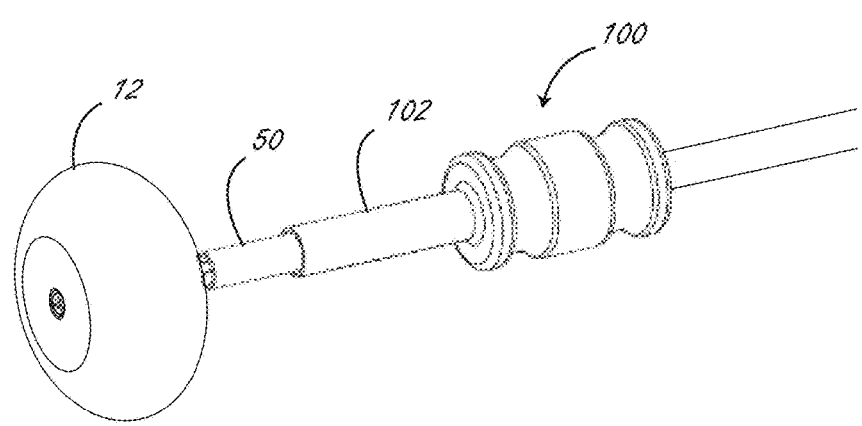
FIG. 7 illustrates the distal end of a device incorporating a slidable sheathing tool comprising a sheathing tube.

FIG. 7 illustrates the distal end of the device incorporating a slidable sheathing tool 100 comprising sheathing tube 102. In use, balloon 12 is collapsed as previously described and then the sheathing tool is slid over the collapsed balloon. The sheathing tube 102 is then fit into the delivery catheter, not shown. The sheathing fixture is then removed, leaving the collapsed balloon within the deliver catheter ready for advancement to the delivery site.

One aspect of the disclosure is a delivery catheter comprising concentric sheaths as a steering mechanism with a mapping system built into the distal tip, where a mapping basket resides during delivery in the space between the two concentric shafts and on delivery is pushed forward out into the heart chamber. Examples of deployable mapping baskets are described above. An ablation catheter may then be delivered through the delivery catheter with the mapping basket in place. Target locations for ablation can then be identified using the electrodes on the mapping basket and target locations are then ablated with the ablation catheter. The location of the ablation catheter may in addition be identified and verified by the mapping basket.

One aspect of the disclosure is an ablation catheter that includes an electrode structure that is about 1 cm to about 5 cm in diameter and resides on the end of an inflatable or expandable structure and may comprise any of the following: an ablation catheter with a balloon carrying multiple electrodes. In some embodiments the multiple electrodes are used alternatively as a single ablation electrode then as a set of individual impedance sensing electrodes capable of monitoring the inter electrode impedance. Such measurements are useful in characterizing the efficacy of the burn resulting from the ablation and/or mapping the ablated area before or after the burn. In some embodiments contact pressure sensitive electrodes may be incorporated as a means of verifying appropriate contact of the electrode to the cardiac tissue. In many embodiments irrigation is provided as described elsewhere herein, wherein the irrigation system incorporates a pressure sensor. In such embodiments contact pressure may be inferred from changes in pressure within the irrigation system associated with increasing the outflow resistance at the irrigation outflow ports press against tissue. In other embodiments a balloon within a balloon configuration is used such that irrigation pressure may be isolated from inflation pressure. The change in pressure within the inflation system then is directly correlated to the contact pressure. In another alternative cooling may be provided by recirculation within the balloon as opposed to irrigation.

In some embodiments the contact pressure of an electrode is measured by impedance matching. An alternate means of characterizing the quality of lesions is to measure changes in acoustic impedance in the ultrasonic pass band. The acoustic impedance will be changed from that of normal tissue both as a function of temperature and denaturation. In such an embodiment a forward looking US transponder can be incorporated in the balloon or on the surface of the balloon. Such a sensor may be embodied as an array of one or more transponders, an array of one or more transmitters and an array of one or more receivers, or a single transponder.

In an alternate embodiment temperature of the lesion may be monitored by microwave radiometry.

Figure 42:
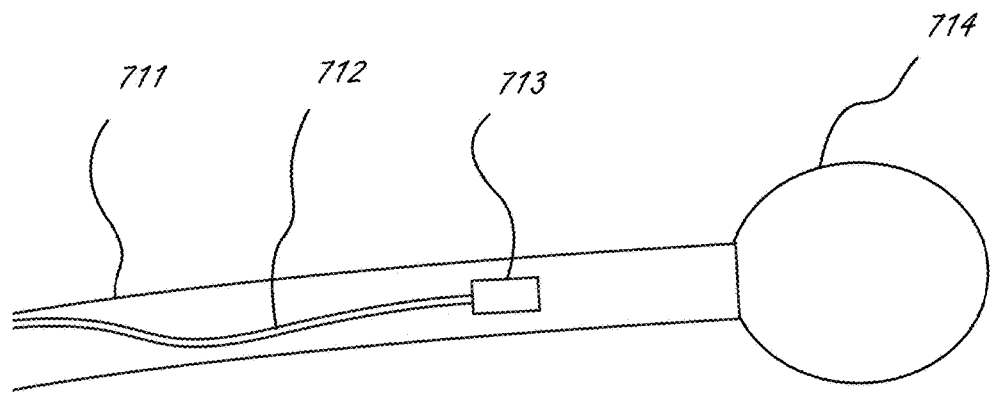
FIGS. 42 and 43 illustrate an exemplary embodiment of an ablation catheter wherein the balloon is configured for contact (physical) measurements.
Figure 43:
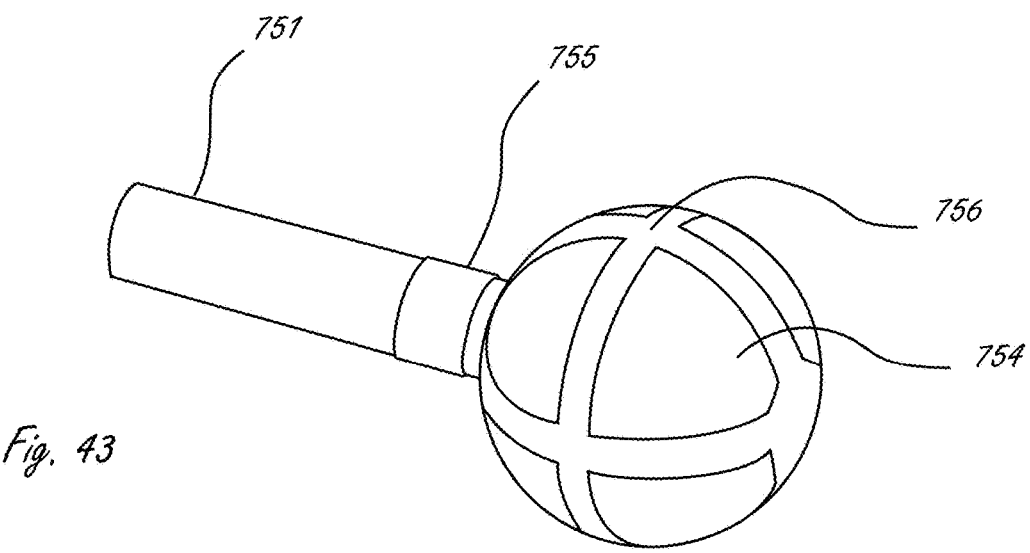

FIGS. 42 and 43 illustrate an exemplary embodiment of an ablation catheter wherein the balloon is configured for contact (physical) measurements. Contact pressure of the balloon and therefore electrodes as characterized by variations in the internal balloon pressure resulting from irrigation holes in the balloon which pass through electrodes being occluded as the electrode is pressed against the tissue. Pressure will increase transiently as the balloon is pressed against the tissue and then reach a new equilibrium associated with any decrease in outflow resistance associated with the occlusion or partial occlusion of irrigation ports. This contact pressure can be mapped by previous experiments to an electrode contact surface area.

A visual contact monitor comprised of a camera within the expandable structure can monitor contact as a change in the visual appearance of transparent windows in the balloon. The changes in visual appearance result from differences in the appearance of blood and tissue.

Contact monitoring may be used to control power delivery. Measurements of electrode contact obtained by any of the means described herein can be used to mediate the amount of power delivered to an electrode. One control algorithm can limit power to an electrode such that the power per area of contact surface is maintained at a constant level.

FIG. 42 illustrates a prototype balloon configured for contact measurement. Balloon 714 is affixed to the end of shaft 711. Strain gage 713 is affixed to shaft 711 and leads 712 which are interfaced with a strain gage amplifier not shown. There are two additional strain gages affixed to the shaft at plus and minus 120 degrees. FIG. 43 is a representation of a similar device in which all three strain gages are configured in strain gage assemble 755 on shaft 751 which comprises the leads to the strain gage assembly. Balloon 754 comprises electrodes 756. In alternate embodiments the pressure of enclosed volumes of fluids or gels arranged in cells near the proximal attachment of the balloon may be monitored via one or more pressure sensors. In yet other embodiments the strain gages may be replaced with displacement sensors. As indicated above measurements from such sensing systems can be mapped to an estimate of electrode contact surface. The balloon of FIG. 42 is 2 cm in diameter and that of FIG. 43 may be 1 to 3 cm in diameter. The configuration of electrodes on the device of FIG. 43 comprises eight electrodes. Such a small profile allows small delivery size and precise maneuverability. Such a system is compatible with a single RF generator and may comprise an irrigation system, not shown, to minimize unwanted injury.

The use of RF ablation in the treatment of atrial fibrillation as described herein poses the risk of thermal damage to the esophagus. This disclosure includes systems and methods to measure temperature of the esophageal wall during RF ablation. In some embodiments a balloon is placed in the esophagus and inflated to make contact with the esophageal wall. A pattern of temperature sensitive material deposited on the balloon measures the temperature change induced by RF ablation. An electronic circuit senses the temperature change to alert the operator.

A thermistor is a type of resistor whose resistance changes with temperature. A negative temperature thermistor (NTC) resistance decreases with temperature due to increased mobility of electrons and subsequent increased ability to conduct current. Commercial NTC thermistors are fabricated from common metal oxides of manganese, nickel, cobalt, iron, copper and titanium using basic ceramics technology. In the basic process, a mixture of a metal oxide powder and suitable binder are sintered in a suitable atmosphere and configuration to achieve the desired temperature coefficient characteristics.

Initial NTC thermistors were fabricated using silver sulfide ($Ag_2S$) powder. More recently, miniaturized, planar silver ion-specific electrodes based on silver sulfide have been fabricated entirely by screen-printing using low-temperature curing polymer pastes and polyester substrates in the form of flexible foils (Sensors and Actuators B 96, 2003, 482-488). Ostensibly, in addition to sensing silver ions, such constructions may also be sensitive to temperature.

A pattern of temperature-sensitive material is deposited on a flexible balloon which is sized to occlude the esophagus. The pattern includes two flexible thermistors (flextors). The two flextors are used in a battery-powered Wheatstone bridge electrical circuit to measure the differential temperature of the two flextors. When placed in the esophagus, the differential temperature induced by RF heating is sensed. If a temperature differential exceeds a limit, the circuit alerts the operator to modify the RF ablation treatment.

Figure 44:
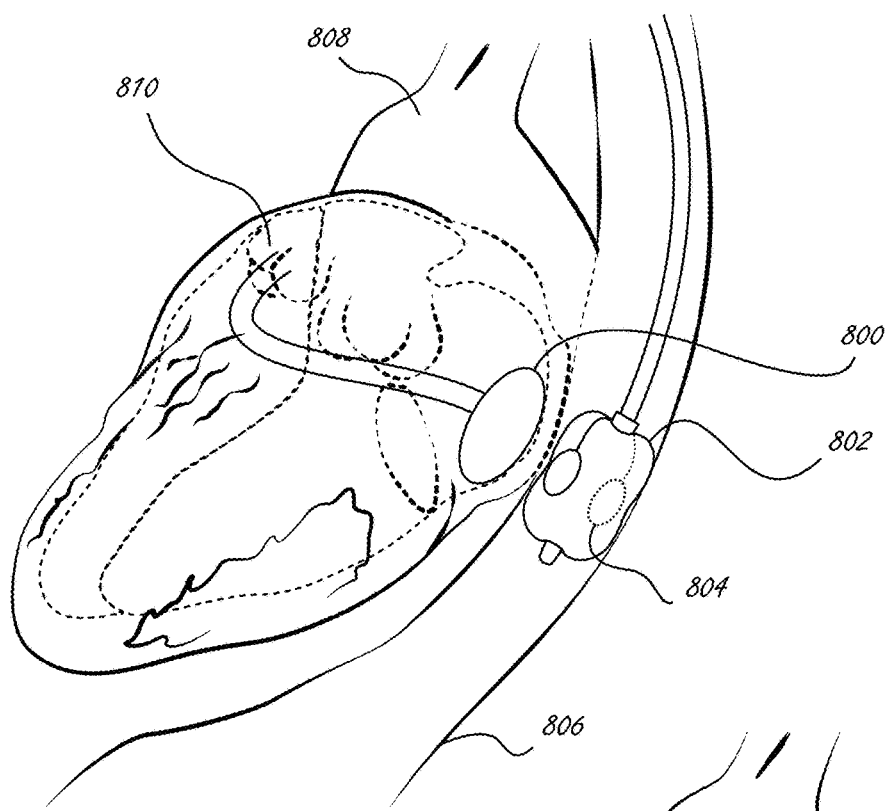
FIG. 44 illustrates an ablation balloon in the left atrium and esophageal temperature balloon positioned and inflated in the esophagus.

An additional way to improve temperature measurement sensitivity may be possible by the design of the flextor pattern. If the pattern is a loop and the loops are diametrically screened on the balloon, then it may be possible to sense the near field component of the RF field generated by the ablation electrode(s). An electronic circuit is connected to one of the flextors to measure the RF energy picked up by it. At the beginning of RF ablation, the operator rotates the balloon shaft such that the RF signal received by the flextor is maximized. This implies that the flextor is closest to the RF source (ablation electrodes) and subsequently to the tissue being heated. In this alignment, differential sensing is enhanced as one flextor will be in the heating field with the other being on the other side of the balloon and not being heated. FIG. 44 illustrates ablation balloon 500 in the left atrium, esophageal temperature balloon 502 positioned and inflated in the esophagus 506, temperature sensor 506 that has a loop configuration. Aortic arch 508 and tricuspid valve 510 are also shown for reference.

Figure 45:
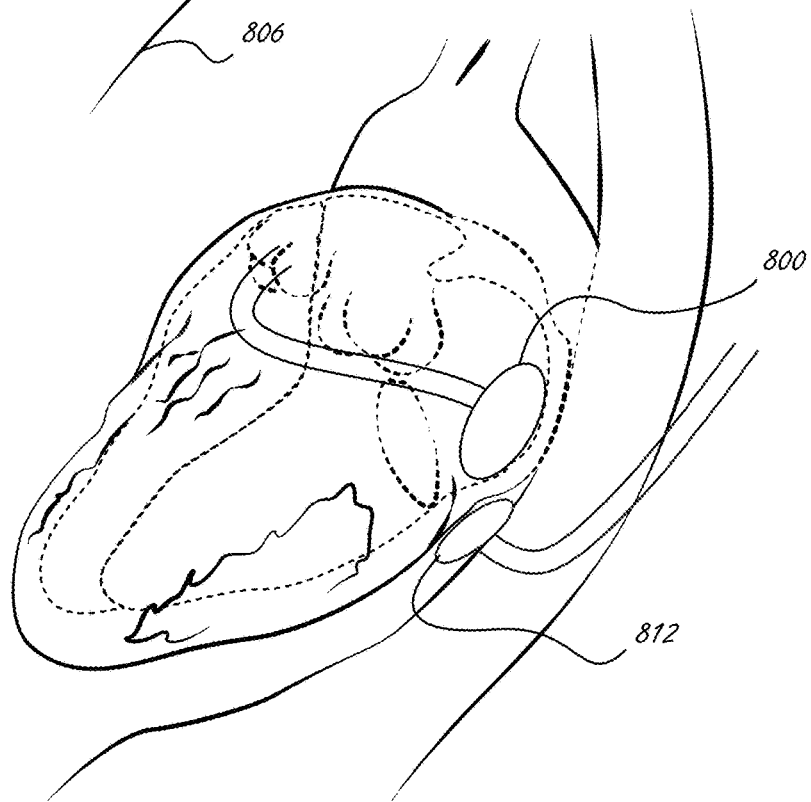
FIG. 45 illustrates an embodiment that includes an endocardial catheter and an epicardial catheter.

FIG. 45 illustrates an embodiment that includes an endocardial catheter and an epicardial catheter. The catheters have electrodes on their bodies and/or on their distal ends, such as described herein. The endocardial electrodes are positioned inside a chamber of the heart and the epicardial electrodes are positioned outside such chamber on the epicardium tissue. The electrodes are positioned opposite each other across the wall defining the chamber the heart. The combination of electrodes is energized in such a way that electrical current flows from the epicardial electrode to the endocardium electrode or vice-versa. FIG. 45 illustrates a method of positioning an endocardial catheter and an epicardial catheter.

In some embodiments herein one or more layers of the flexible circuit can have a discontinuity formed therein. The discontinuity can result in the flexible circuit having less relatively stiff material than without the discontinuity, which can result in a more flexible flex circuit. Enhanced flexibility can make the flexible circuit more easily deformable and less likely to damage one or more components of the expandable member during deformation, such as when deforming the expandable member for sheathing it within a sheath. As used herein, the term "discontinuity" includes a gap and an aperture, examples of which are described herein.

In some embodiments, if the flexible circuit includes an optional substrate layer, the substrate layer can have a discontinuity formed therein.

FIGS. 46A-46C illustrate an embodiment in which the flexible circuit includes a layer with a discontinuity formed therein, and in this embodiment the substrate layer includes a discontinuity. The flexible circuit includes a conductor in electrical communication with an ablation electrode. FIG. 46A illustrates a view from inside the inflatable balloon member 3000 (looking outward) of a portion of flexible circuit in which the substrate includes a discontinuity. FIG. 46B shows the cross section A-A shown in FIG. 46A. Section A-A shown in FIG. 46B includes inflatable balloon 3002, substrate layer 3004 with a discontinuity formed therein, conductive layer 3006, reflection adjuster 3008 (described generally above) in this embodiment being a black paint, and ablation electrode 3010. In this embodiment conductor 3006, which is disposed directly on top of substrate 3004, also includes a discontinuity therein. In this embodiment substrate layer 3004 and conductor 3006 thus both have a discontinuity formed therein.

In this particular embodiment the configuration of discontinuity in substrate 3004 is a hole, that is, the discontinuity is completely surrounded by substrate material, and the shape of the hole defines the shape of the discontinuity. The configuration of the hole in this embodiment can be seen in FIG. 46A, which illustrates the aperture filled with a reflection adjuster 3008, which is described in more detail herein. As can be seen in FIG. 46A, the discontinuity is generally circular in this embodiment, with a protrusion of substrate extending distally into the generally circular aperture.

In this embodiment a reflection adjuster 3008 is disposed within the discontinuity, and in this embodiment the reflection adjuster is a black paint, which reduces reflection by absorbing light. The black paint can be seen filled into the generally circular discontinuity in FIG. 46A, and in the cross section in FIG. 46B. If black paint is used as the reflection adjuster, the black paint can be painted onto the inflatable ablation member into the discontinuity in the substrate.

The discontinuity removes material from the substrate (which in some embodiments is a relatively stiff polyamide), thus making the flex circuit more flexible since the black paint is more flexible than the substrate material. The discontinuity provides an additional advantage in that it is also a place for the reflection adjuster to be applied to reduce reflection. The advantages of the discontinuities herein include that they result in less relatively stiffer substrate material for a more flexible circuit, and are convenient locations for a reflection adjuster (e.g., black paint) to be applied to the inflatable ablation member. While FIGS. 46A and 46B illustrate aspects of a single ablation electrode 3010, the discontinuities can be included in any of the substrates layers (or other layers) in the flexible circuit. For example, FIG. 47 illustrates an exemplary substrate layer that can be applied to the inflatable ablation member such that it is carried by an outer surface of the inflatable balloon. In FIG. 47, substrate 3004 includes a plurality of discontinuities 3005. Only two discontinuities are labeled, but eighteen are shown. In the embodiment in FIG. 47, the substrate includes six extensions extending proximally, each one directly associated with three of the discontinuities. In the exemplary embodiment in FIG. 47 there can be eighteen ablation elements, one positioned radially over each one of the discontinuities. In FIG. 47 the substrate material forms a central region 3007, which when applied to the inflatable balloon is disposed at the distal end of the balloon.

FIG. 46C illustrates an image on a console or screen, such as those described above, in which four images from four imaging elements (e.g., cameras) are superimposed, as is described above. In FIG. 46C, each region of the inflatable ablation member that has an ablation electrode has a reflection adjuster radially within the electrode. As shown in FIGS. 46A-C, the reflection adjusters 3008 do not extend all the way to the periphery of the ablation electrodes 3010.

The optional discontinuity need not be a hole, as shown in the example in FIGS. 46A-47. For example, the discontinuity need not have substrate material all the way around the discontinuity, and thus need not be a hole. For example, an edge of a discontinuity can have a general "C" shape, or a "U" shape, and still be considered a discontinuity as used herein. In some embodiments the discontinuity is formed by substrate (or other layer) material extending distally on one or more sides of the discontinuity, as is the case with a hole, or a "C" or "U" shaped discontinuity.

The flexible circuit includes irrigation ports 3012, one through each of the electrode/flexible circuit assemblies. Ports 312 are in fluid communication with the inside of the inflatable balloon, which is in fluid communication with an inflation lumen in the catheter as described above.

The embodiment in FIGS. 46A-C is an example of an ablation catheter that includes an inflatable balloon carried by a distal region of an elongate shaft, and a flexible circuit carried by an outer surface of the balloon, the flexible circuit comprising a substrate and a conductor, the substrate including a discontinuity, and at least one ablation electrode, in electrical communication with the conductor, carried by the outer surface of the balloon and disposed over the discontinuity. In FIGS. 46A-C, the discontinuity forms a hole in the substrate, and is at least partially filled with a reflection adjuster. In this embodiment the reflection adjuster is a black paint that has been painted into the discontinuity. The reflection absorber can optionally be a conductive black paint.

In alternative embodiments one or both of the substrate and conductor do not have discontinuities therein. In these embodiments the reflection adjuster (e.g., black paint) could be applied on the underside (radially within) of either the substrate layer or the conductive layer.

In alternative embodiments one or more layers can have discontinuities, but are not filled in with a reflection adjustor. For example, the electrode material could be disposed within the periphery of the discontinuity, but the flexible circuit may still be more flexible so that it is more easily deformed.

In some embodiments above, the expandable member, such as an inflatable ablation member, includes one or more visualization elements (e.g., cameras) to provide visualization of one or more aspects of the ablation procedure (see, e.g., FIG. 38). The visualization elements above can help characterize lesion formation, including quality thereof. In some embodiments the expandable member can include, either in addition to one or more cameras or instead of, a way of characterizing the quality of lesions by measuring changes in acoustic impedance in the ultrasonic pass band. The acoustic impedance of ablated tissue will be changed from that of normal tissue both as a function of temperature and denaturation. In these embodiments a forward looking ultrasound ("US") transponder ("UT") can be incorporated in the balloon or on the surface of the balloon. Such a sensor system may be embodied as an array of one or more transponders, an array of one or more transmitters and an array of one or more receivers, or a single transponder. The UT can monitor characteristics which include changes associated with: increased temperature, gas released from heating the tissue, steam associated with overheating the tissue or blood at the electrode interface, densification associated with denaturing the tissue. These changes allow for the use of a UT to monitor and control the process of an RF ablation. These characteristics may be monitored as changes in refraction, reflection, acoustic impedance, signal attenuation, back scatter from scatterers comprised in the tissue, thermal strain, timing and phasing associated with echoes arising from natural boundaries and boundaries associated with changes in the heated and ablated tissues, amongst other phenomena.

This disclosure includes an ablation catheter comprising an elongate shaft, an inflatable balloon carried by a distal region of the shaft, a flexible circuit, including a conductor in electrical communication with an ablation electrode, disposed outside of and carried by an outer surface of the inflatable balloon, and an ultrasound monitoring member, configured for use in monitoring at least one aspect of tissue ablation with the ablation electrode.

This disclosure includes an ablation catheter, comprising an elongate shaft, and an inflatable ablation member, carried by a distal region of the shaft, the inflatable ablation member including a flexible circuit, including a conductor in electrical communication with an ablation electrode, disposed outside of and carried by an outer surface of an inflatable balloon, and an ultrasound monitoring member, configured for use in monitoring at least one aspect of tissue ablation with the ablation electrode.

Any of the ultrasound monitoring members herein can optionally be carried by an outer surface of the inflatable balloon, may optionally be part of the inflatable balloon, and/or may optionally be disposed within the inflatable balloon. As used herein, "carried by" or derivatives thereof is intended to mean that an element is secured to something, either directly or indirectly. For example, a flexible circuit carried by an outer surface of a balloon can be indirectly attached to the outer surface of the balloon. That is, there can be one or more intermediate layers between the outer surface of the balloon and the flexible circuit.

Figure 48:
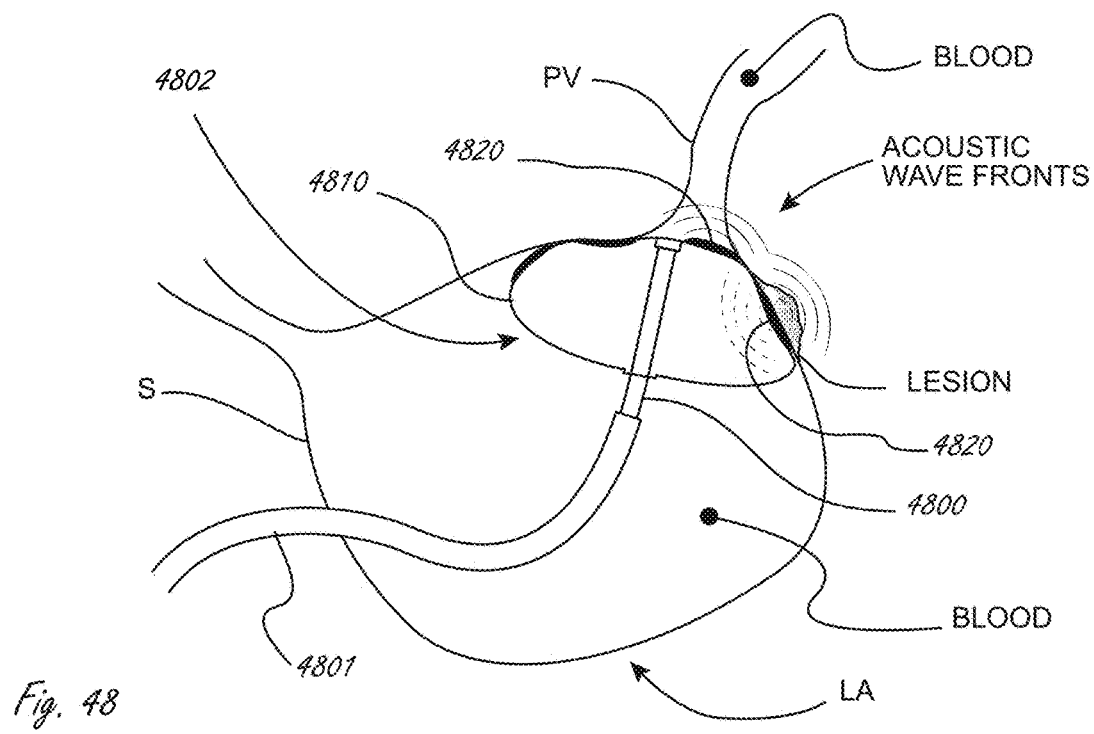
FIG. 48 illustrates an exemplary ablation catheter that includes at least one ultrasound monitoring member.

FIG. 48 illustrates an exemplary embodiment of an ablation catheter that includes an inflatable ablation member carried by a distal region of an elongate shaft, in which one or more ultrasound monitoring members are carried by an outer surface of the inflatable balloon. The one or more ultrasound monitoring members are configured for use in monitoring at least one aspect of tissue ablation. Ablation catheter 4800 can be any of the ablation catheters herein in which one or more ultrasound monitoring members are carried by an outer surface of the inflatable balloon, such as when the ultrasound monitoring member is embedded in the flex circuit elastomeric electrode assembly.

FIG. 48 illustrates a cross section of such ablation catheter 4800 extending distally from delivery catheter 4801 and positioned in a left atrium LA through septum S. Ablation catheter 4800 comprises inflatable ablation member 4802 carried by the distal region of an elongate shaft of catheter 4800. Inflatable ablation member 4803 includes inflatable balloon 4810, an outer surface of which carries at least one flex circuit and at least one ablation electrode, which are described generally herein. The assemblies of the flex circuit and an electrode can be referred to herein as flex circuit electrode assemblies 4820. The flex circuit electrode assemblies include at least one flexible circuit and at least one ablation electrode in conductive communication. Inflatable ablation member 4802 also includes one or more ultrasound transponders. The inflatable balloon and electrodes can be the same or similar to those described above, with the exception that one or more electrode assemblies 4820 can also include an ultrasound monitoring member. Inflatable ablation member 4802 illustrated is, in this exemplary embodiment, placed within a left atrium adjacent to a pulmonary vein PV. As illustrated, two of the ultrasound transponders are being ultrasonically activated, as indicated by the wave fronts emanating from the assemblies 4820 on the right in the figure. The ultrasound monitoring member that is positioned over the pulmonary vein PV can capture information indicating that it is adjacent to blood as opposed to tissue, thereby providing information to the user that the ablation electrode associated with it should not be activated for an ablation. The ultrasound monitoring member disposed within the assembly 4820 on the far right, which is adjacent to tissue comprising a lesion that was created by activation of the electrode, is optionally monitoring the increase in depth of the lesion as a function of continued activation. Additionally, the ultrasound is providing information that can be used to control the rate of energy delivery, which helps to minimize over heating of the tissue by monitoring RF tissue interactions including tissue temperature, creation of gas bubbles and/or steam at the electrode tissue boundary or within the tissue, and the denaturation of the tissue. In some embodiments information associated with the lesion and electrode contact is provided to the user to allow the user to modify the ablation controls. In other embodiments information obtained using the ultrasound monitoring member is used directly by the ablation controller to modify ablation control parameters.

Figure 49:
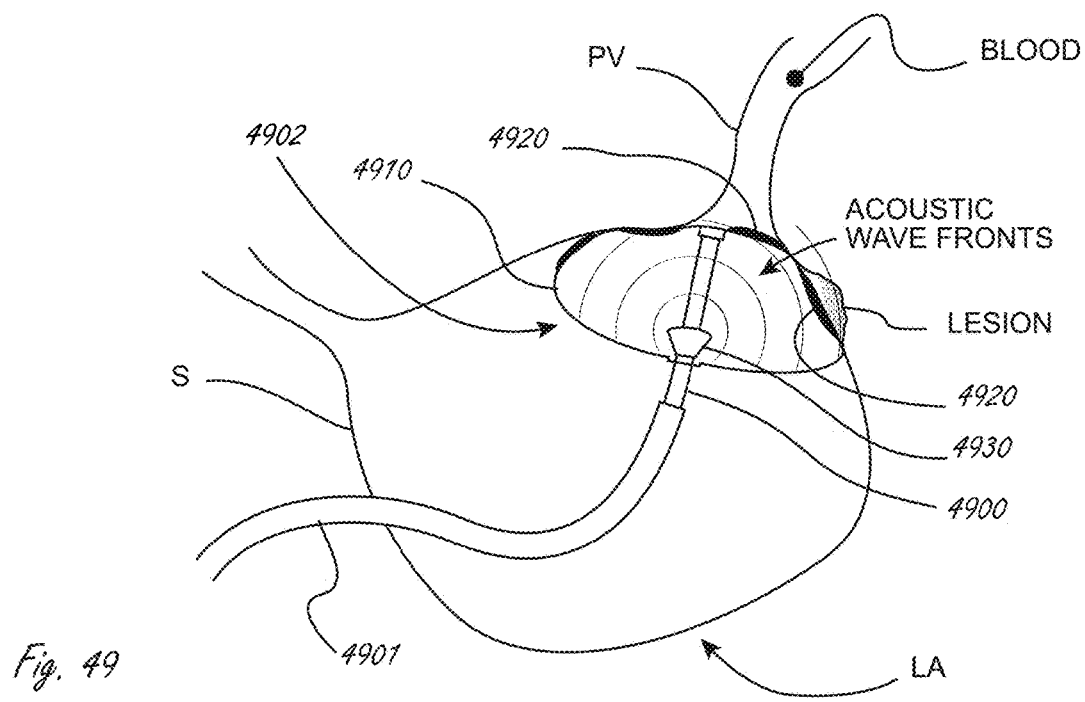
FIG. 49 illustrates an exemplary ablation catheter that includes at least one ultrasound monitoring member.

FIG. 49 illustrates a distal region of ablation catheter 4900 similar to that shown in FIG. 2A, wherein the optical camera assembly from FIG. 2A has been replaced by an ultrasound transponder imaging array 4930 within the balloon, and in this embodiment the flex circuit electrode assemblies 4920 do not comprise ultrasound transponders.

In other embodiments the catheter includes one or more cameras inside the balloon and one or more ultrasound monitoring members inside the balloon.

In an alternate embodiment to that of FIG. 49, array 4930 is replaced by an ultrasonic emitter, and an ultrasonic receiver is included in the one or more electrode flex circuit assemblies. In such an embodiment the receiver (or detector) can monitor the initial ultrasonic pressure wave signal as the signal first passes the detector carried by the balloon surface as it travels out to the tissue, and then monitor any return signals arising from interactions with the tissue adjacent the inflatable ablation member. Information associated with differences in these signals can then be used to characterize initial conditions and changes in the adjacent tissues associated with one or more aspects of the ablation procedure. In some embodiments the one or more receivers may be included in the optional flex circuit substrate. One exemplary way of accomplishing this is to use a piezoelectric material such as polyvinylidene fluoride ("PVDF") as the flex circuit substrate, and to pole and interface a subsection of the substrate for use as ultrasonic microphones. The ultrasonic emitter in such an embodiment can be a single emitter, multiple emitters each adapted to be used as individual emitters that are directed at particular areas of the balloon surface, or a phased array capable of directing energy at different areas. Such an embodiment may additionally include multiple cameras within the balloon.

In other embodiments the ultrasonic transducer within the balloon can be replaced with multiple sets of electrodes arrayed disposed around and carried by the guidewire lumen within the balloon. In such embodiments an RF signal may be applied between the electrodes to super heat the fluid in proximity to the electrodes. Alternatively, a high voltage gradient may be applied across the electrodes to create a spark within the fluid within the balloon. In either case there will be an acoustic impulse associated with the growth and collapse of the gas or plasma "bubble" created. This acoustic impulse can be used as a source and monitored as it passes through ultrasonic receivers arrayed on the surface of the balloon as it passes them on the way into the tissue monitored again as the reflections from within the tissue pass back through.

Figure 50A:
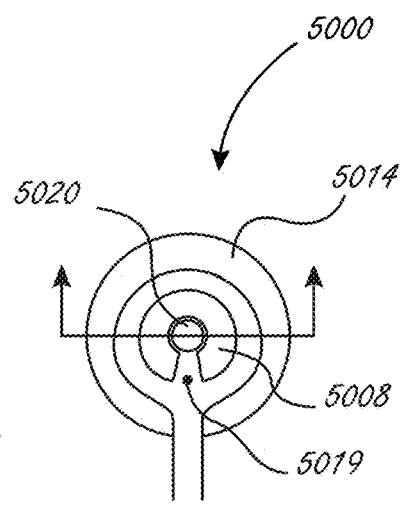
FIGS. 50A-50B illustrate an ultrasound monitoring member carried by an inflatable balloon and within the periphery of an ablation electrode.
Figure 50B:
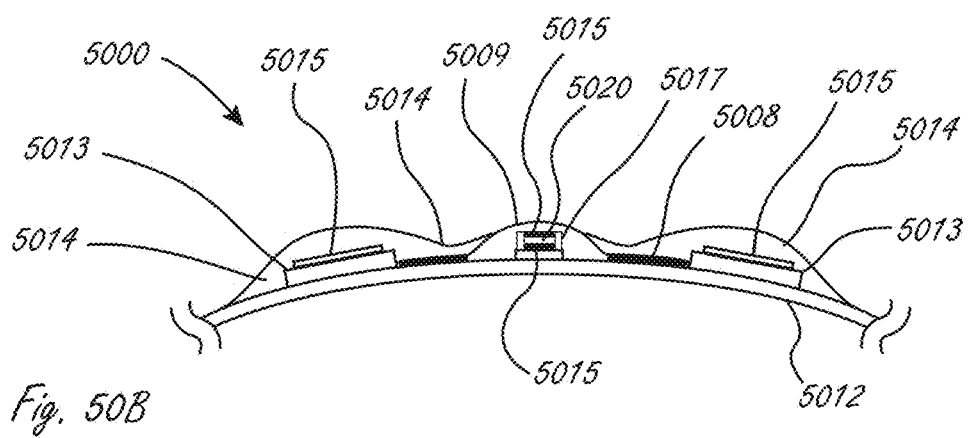
Figure 50C:
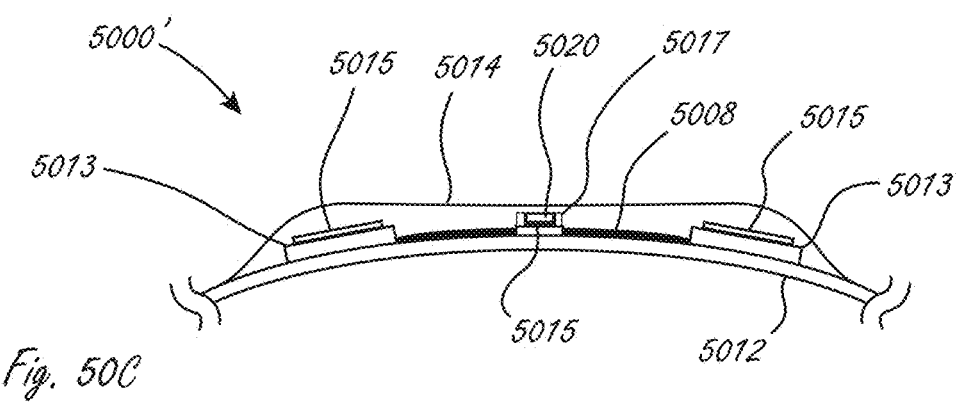
FIG. 50C illustrates an ultrasound monitoring member carried by an inflatable balloon and within the periphery of an ablation electrode, wherein the ultrasound monitoring member is radially within the electrode.

FIGS. 50A-C illustrates an exemplary flex circuit elastomeric electrode assemblies 5000 and 5000' similar to that of FIG. 46 where UTs 5020, irrigation aperture 5019, and associated control lines, have been incorporated into the flex circuit and the UT 5020 is carried by the balloon, included in the electrode flex circuit assembly, and is disposed within the periphery of the elastomeric electrode. The position within the periphery of the electrode can be seen most clearly from FIG. 50A. FIG. 50A illustrates a top view indicating the section illustrated in FIGS. 50B and 50C. FIG. 50B illustrates an exemplary embodiment of a flex circuit elastomeric electrode assembly 5000 and the structures associated with the control of the elastomeric energy delivery element and the UT comprised therein. Energy is delivered to electrode 5014 via conductor 5015 extending around and on the outer ring of the substrate layer 5013 (the substrate layer and the conductor also have a discontinuity in this embodiment). Black paint 5008 is applied in areas beneath (i.e., radially within) the electrode 5014 and within the substrate ring. The UT 5020 and associated control circuitry is carried on the central region of the substrate 5013 and coated with a nonconductive elastomer 5009. In the embodiment of assembly 5000 the single element UT requires two conductors. FIG. 50C illustrates an alternate embodiment of a flex circuit elastomeric electrode assembly 5000' wherein the UT assembly is encapsulated in (radially within) the conductive energy delivery element 5014 which, along with its support conductor, comprises one aspect of its control circuitry. In FIG. 50B the ultrasound monitoring member is not radially within the electrode, but in FIG. 50C the ultrasound monitoring member is radially within the electrode.

Figure 51A:
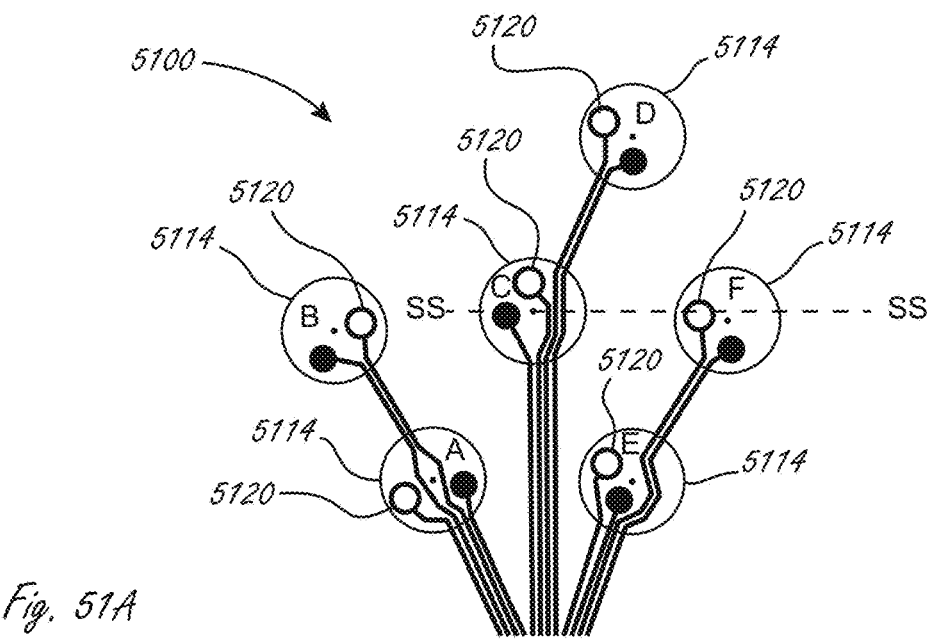
FIGS. 51A-51C illustrate an exemplary flex circuit ablation electrode assembly comprising at least one ultrasound monitoring member.
Figure 51B:
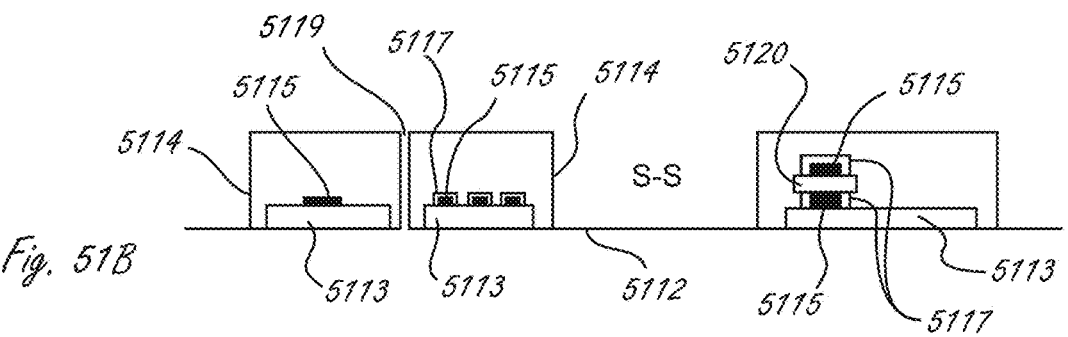
Figure 51C:
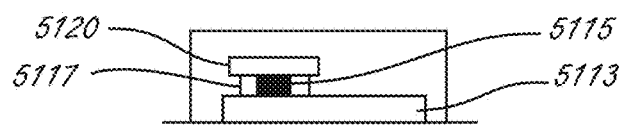

FIGS. 51A-C illustrate exemplary features of an alternate flex circuit elastomeric electrode assembly 5100 similar to that of FIG. 9, where UTs 5120, and associated control lines, have been incorporated into the assemblies at locations within the periphery of the elastomeric electrodes 5114. FIG. 51A illustrates one third of a flex circuit elastomeric electrode assembly 5100 for use on an ablation balloon as described elsewhere herein. FIG. 51B illustrates a cross section, from FIG. 51A, of two of the electrode structures. On the left is illustrated a cross section showing structures associated with driving an elastomeric RF electrode and control of a single element UT. On the left is the cross section through the middle of a flex circuit electrode assembly that includes an irrigation aperture 5119, where no UT is visible. Substrate layer 5113 is carried by and on the surface of balloon membrane 5112 with a section of conductor 5115 exposed, on the left of the irrigation aperture, such that it transmits power conductively to elastomeric electrode 5114. On the right of the irrigation aperture is a substrate layer 5113 carrying three conductors 5115 covered with insulation layers 5117. These conductors provide power and control for the electrode carried by the balloon that is distal to where the cross section was taken, which can be seen in FIG. 51A. All of these flex circuit elements are covered by an elastomeric conductor that includes the energy delivery element 5114. On the right in FIG. 51B is a cross section of a flex circuit elastomeric electrode assembly 5100 comprising a UT 5120 and associated control circuit elements comprised of conductors 5115 and insulator 5117. These elements are affixed to substrate 5113 which in turn is affixed to the outer surface of balloon 5112. As illustrated in FIG. 51B, the UT comprises a single element transponder with two conductors for control.

FIG. 51C illustrates an alternate embodiment of the cross section on the right in FIG. 51B, where the ablation electrode and associated conductor is used as a circuit element in the control of the UT 5120. When the elastomeric electrode is used to drive the UT circuit element, it can be used as an individual source, or alternatively the elastomeric electrodes may be used as common return.

Figure 52A:
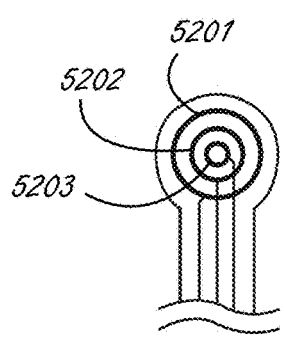
FIG. 52A illustrates a 3 element array comprised of concentric rings.
Figure 52B:
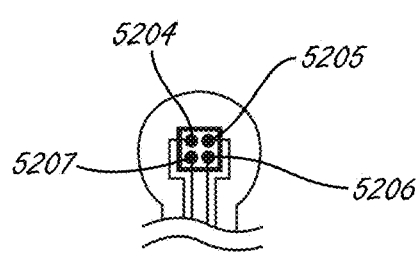
FIG. 52B illustrates a rectilinear 4 element array.

In yet other embodiments the UT carried by the surface of the balloon may comprise more than one transponding element for use in a phased array configuration. FIG. 52 illustrate two such configurations. FIG. 52A illustrates a 3 element array comprised of concentric rings 5201, 5202, 5203. FIG. 52B illustrates a rectilinear 4 element array, 5204-5207. Although FIGS. 51A-C illustrate control circuitry associated with single element UTs one skilled in the art can easily modify the disclosure herein to accommodate the additional control circuitry required to control the additional elements. Other configurations incorporating more or fewer UT elements are also conceived herein.

Figure 53:
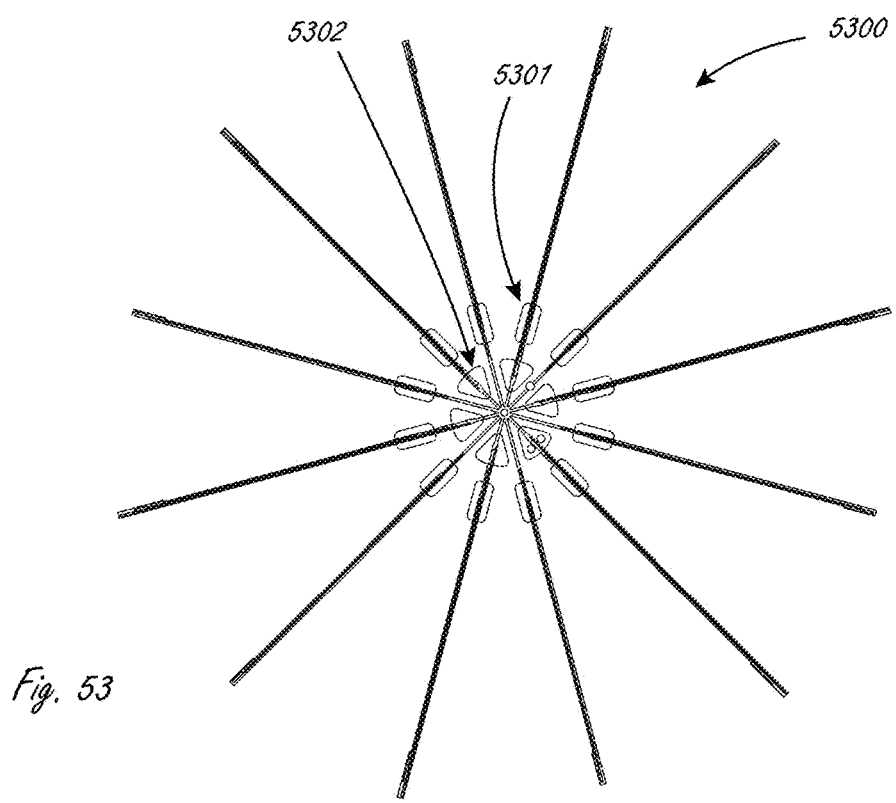
FIG. 53 illustrates an exemplary flexible circuit and ablation electrode configuration, including at least one ultrasound monitoring member.
Figure 54A:
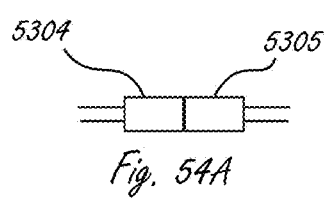
FIGS. 54A-B illustrate exemplary arrangements of ultrasound monitoring members supported by a trace of a flex circuit that passes between adjacent electrodes.
Figure 54B:
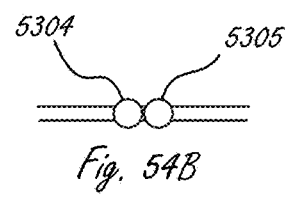
Figure 54C:
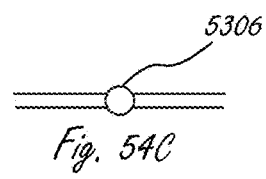
FIG. 54C illustrates an ultrasound transponder mounted on a trace that passes between adjacent electrodes.

In some embodiments the ultrasonic sensing may be facilitated by ultrasonic emitters and receivers carried by and adjacent one another on the surface of the balloon. A number of such arrangements are illustrated in FIGS. 53 through 55. FIG. 53 illustrates a flex circuit 5300 pattern similar to that of FIG. 47, which supports two sets of concentric ablation electrodes 5301 and 5302. FIGS. 54A-B illustrate exemplary arrangements of emitter 5304 detector 5305 pairs supported by traces of the flex circuit that pass between adjacent electrodes, which can be seen in FIG. 53. FIG. 54C illustrates a transponder 5306 mounted in the same position relative to the adjacent electrodes. In such configurations the ultrasonic monitoring elements are not within the RF electrodes and the ablation progress is monitored between the adjacent electrodes providing information on the continuity of the burn pattern.

Figure 55A:
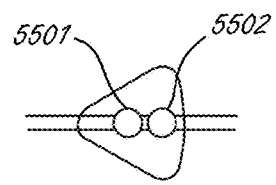
FIGS. 55A and 55B illustrate two exemplary emitter and receiver patterns wherein the emitter and receiver pairs are mounted within the periphery of the ablation electrode.
Figure 55B:
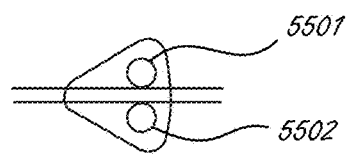

FIGS. 55A and 55B illustrate two exemplary emitter and receive patterns wherein the emitter and receiver pairs are mounted within the periphery of the ablation electrode.

Figure 56:
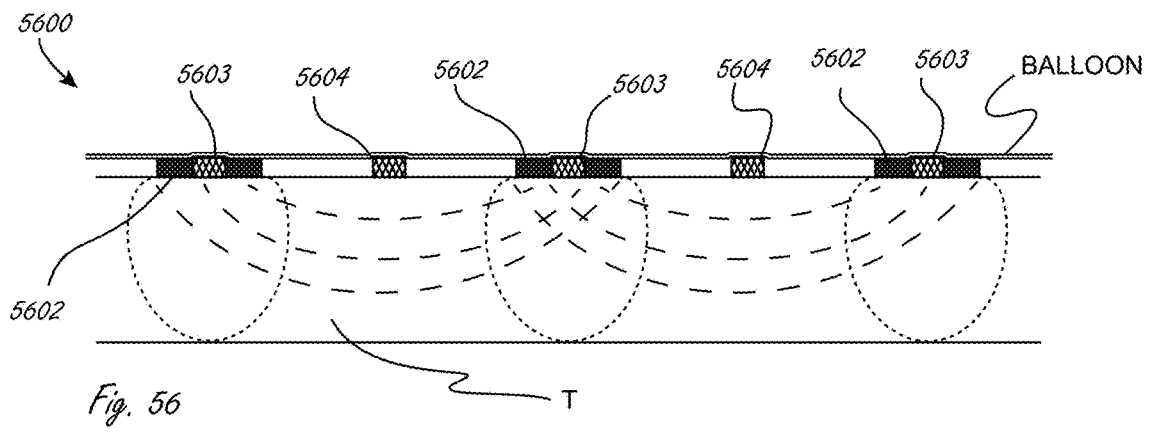
FIG. 56 illustrates an exemplary inflatable ablation member comprising a plurality of ablation electrodes and a plurality of ultrasound monitoring members.

FIG. 56 illustrates a cross sectional view of an inflatable ablation member 5600 that includes a flex circuit, elastomeric ablation electrodes 5602, and ultrasonic transducers 5603 and 5604 all carried by a surface of a balloon, and a section of adjacent tissue "T". Exemplary burn patterns within the tissue associated with a monopolar activation, dotted lines, and bipolar activation, dashed lines, of the ablation electrodes 5602 have been illustrated. Transducers in this embodiment are placed both within the elastomeric electrodes 5603 and between the elastomeric electrodes 5604. In this configuration the progress of burns associated both with monopolar activation beneath and elastomeric electrode and bipolar activation between adjacent electrodes can be monitored independent of each other.

Figure 57:
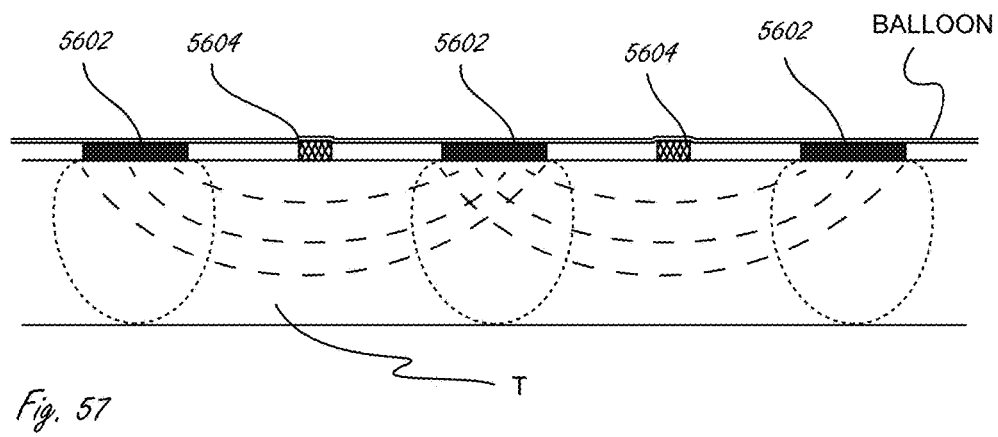
FIG. 57 illustrates an exemplary inflatable ablation member comprising a plurality of ablation electrodes and a plurality of ultrasound monitoring members carried by the balloon and disposed between electrodes.

FIG. 57 illustrates an alternate embodiment in which the ultrasonic transducers 5604 are mounted only between the elastomeric electrodes. In such an embodiment, when using transducers individually, the field of view will be limited to areas between electrodes.

Using an alternate procedure, wherein some transducers are set to listen and other transducers are set to receive, the transducer arrangements described in FIG. 56 and FIG. 57 can provide information over a broader field of view. In yet other embodiments, sender and receiver pairs may be used in place of the transducers just described.

In still other embodiments the senders and receivers may be distributed as opposed to used in pairs. Such an embodiment is comprised in the following alternate description of FIG. 56, where 5603 are senders and 5604 are receivers.

Figure 58:
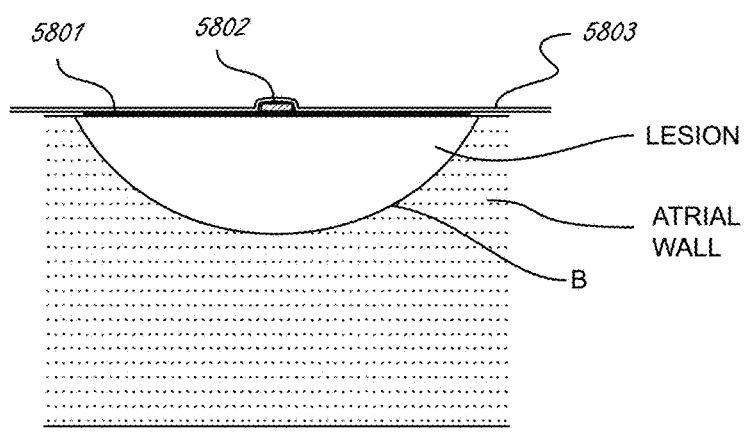
FIG. 58 illustrates an exemplary method of using an inflatable ablation member herein that includes an ultrasound monitoring member.

FIG. 58 illustrates a cross sectional view of a flex circuit ablation assembly comprising elastomeric ablation electrode 5801, ultrasonic transducers 5802, all carried by and mounted on balloon 5803, and a section of adjacent tissue comprising a portion of an atrial wall near a pulmonary vein. The transducer 5802 can be used to monitor local tissue prior to, during, and/or after a burn generated by electrode 5801, and/or adjacent electrodes not shown. Acoustic energy delivered into the tissue from the transducer 5802 will propagate through the tissue and be affected by the properties of the tissue in its path. Some of the energy delivered will be returned to the transducer via reflections off of boundaries "B" between materials with differing acoustic impedances. Such boundaries associated with native tissues include those associated with the boundary between the atrial wall and the pericardial fluid or that between the pericardial fluid and the pericardia.

Additional boundaries will be created when a burn is effected where the acoustic impedance of the denatured and or desiccated tissue will have a different acoustic impedance than that of the native tissue. As described here and in the preceding paragraph, these reflections associate with tissue features which are considerably larger than the wavelength of the acoustic energy used to query the tissue.

In addition to the reflections just described energy will also be returned via reflection or scattering by features of the tissue which are of a size comparable with the wavelength of the acoustic energy used to query the tissue. Given the characteristic size of features associated with muscle, such scattering will occur over frequencies in the range of about 5 MHz to about 50 MHz. As muscle is denatured and or desiccated the features associated with the characteristic wavelengths will either change in size or disappear altogether.

In the model as described in FIG. 58, the amount of energy returned from a burst of energy delivered at a given frequency, and the time at which it is returned, will additionally be dependent on the absorption properties of the intervening tissues. The attenuation via absorption in tissue increases as a function of frequency.

In some embodiments scanning, multi-frequency, chirp, or broadband excitation may be used to follow changes in the queried volume of tissue during a burn. Such an embodiment would be of particular use if the scattering properties of the muscle were a primary determinant of the quality and progress of a burn. In such embodiments individual transmitters and receivers may provide additional merit in that each can be designed to optimize different characteristics.

Figures 59, 60:
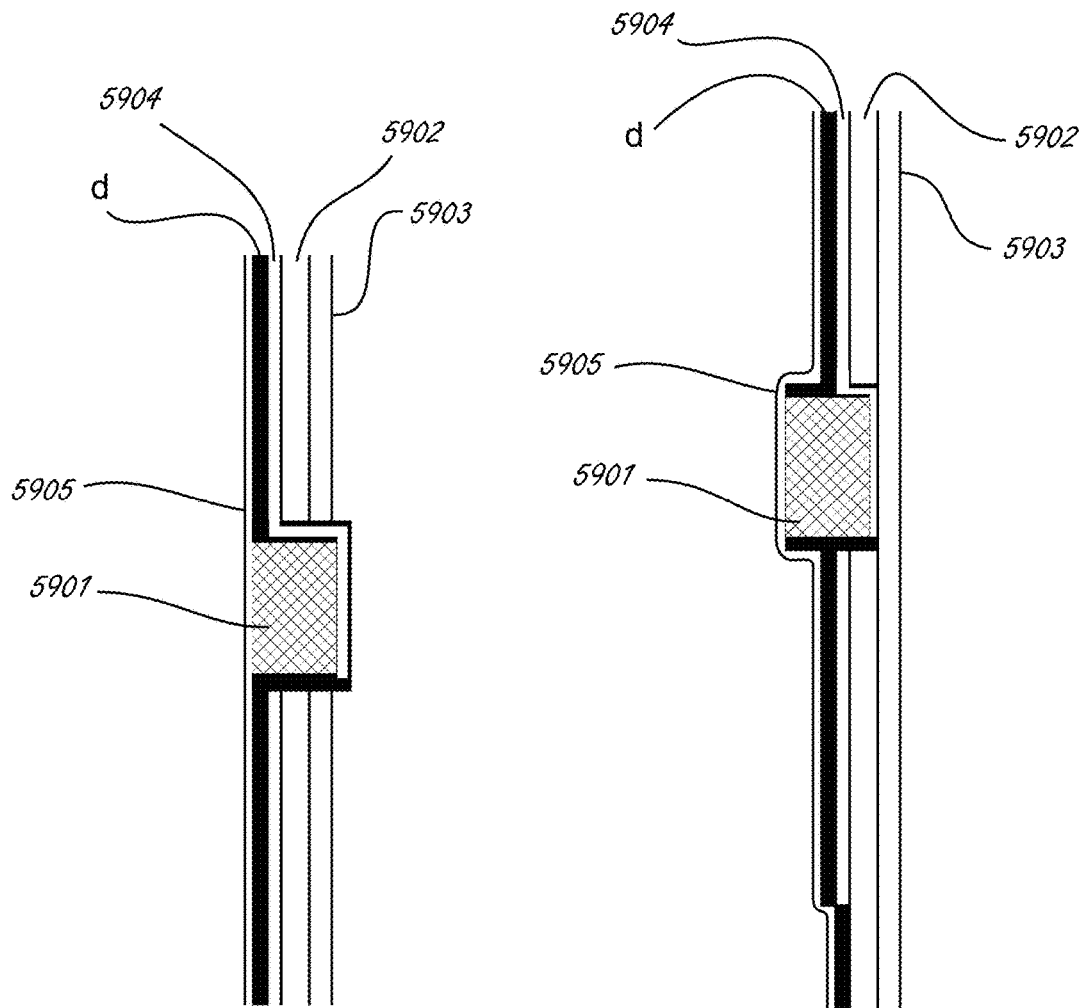
FIG. 59 illustrates an exemplary configuration of an ultrasound monitoring member in an inflatable ablation member.
FIG. 60 illustrates an exemplary configuration of an ultrasound monitoring member in an inflatable ablation member.

FIGS. 59 and 60 illustrate two variations of how a PZT transducer 5901 may be implemented in a flex circuit electrode assembly that that includes an elastomeric electrode mounted on a balloon. As illustrated, the various thicknesses are close to scale for a PZT transducer tuned to about 30 MHz. FIG. 59 illustrates an embodiment in which the transducer 5901 sits in a hole in the substrate 5902 and balloon 5903 thereby creating no change in contour of the elastomeric electrode. Conductors 5904 and the elastomeric electrode 5905 are used to both power and query the UST 5901. In FIG. 60 the bottom surface of the UST 5901 sits on the balloon 5903 and thereby, given the required thickness, creates a change in the contour of the elastomeric electrode.

Any of the visualization procedures described herein may be enhanced when gated to portions of the cardiac cycle. In particular, when monitoring a burn in progress within an atrial wall, the wall thickness and density, therefore acoustic impedance, will change as a function of where in the cycle it is measured. Gating to a particular portion of the cardiac cycle will lessen artifacts and increase signal to noise in the image associated with the changing thickness. Such improvements associate with one or more of the following amongst others. Information on the progress of a burn boundary to will be measured against a more constant wall thickness. Attenuation of signal returning from the distal aspect of the wall will not vary as a function of the changing wall thickness. Gating also provides the opportunity to measure variation in the thickness of the wall along the contraction cycle. As a burn progress this variation will diminish.

In an alternate embodiment temperature of the lesion may be monitored by microwave radiometry.

Figure 61:
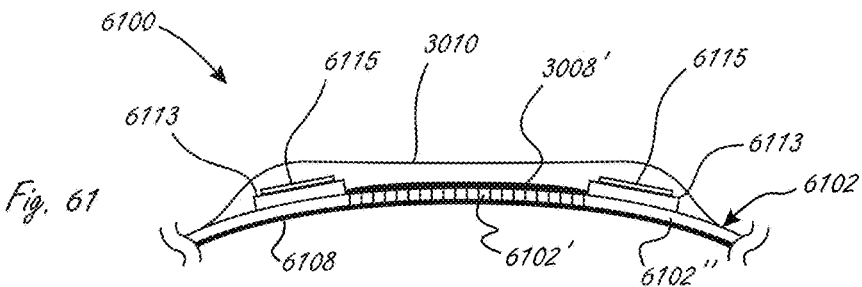
FIG. 61 illustrates an exemplary inflatable ablation member that includes a conductive ink.

FIG. 61 illustrates features of an alternate embodiment for incorporation of an ultrasonic transducer and/or alternately just a sensor carried by the surface of a balloon incorporating a flex circuit electrode assembly that includes an elastomeric electrode. The device illustrated in FIG. 61 comprises the flex circuit electrode assembly 6100 comprising an elastomeric electrode 3010, as illustrated in FIG. 50, with the exception that the black ink 3008 in the discontinuity is replaced with a conductive ink 3008'. Such inks may comprise carbon black, or graphene, or other nano carbon structures. Substrate 6113 and conductors 6115 are included in the flex circuit. In this embodiment the balloon 6102 includes the sensor or transducer. In such an embodiment the balloon can be comprised of a PVDF, or similar flexible polymer with piezoelectric qualities. Regions of the balloon to be used as sensors or transducers 6102' are poled during manufacture and those not intended for use as transducers or sensors 6102" are left un-poled. Alternatively, the entire balloon may be poled and regions de-poled by heating them after the poling process. In some instances the entire balloon will be poled and only those sections interfaced to conductive regions will be poled. In such an embodiment transparent conductor(s) 6108 are deposited on the inner surface of the balloon. The transparent conductor comprised within the balloon can be configured such that there are multiple transparent conductors within the balloon or a single common transparent conductor depending on the desired protocol for polling the poled regions. The flex circuit structures 6113 and 6115, black ink 3008', and elastomeric electrode 3010 provide the conductive path to the other side of the transducer or sensor. When multiple transparent conductors are desired on the balloon, the entire surface of the balloon may be coated and then after coating, sections may be ablated away via laser ablation.

Figures 62A, 62B:
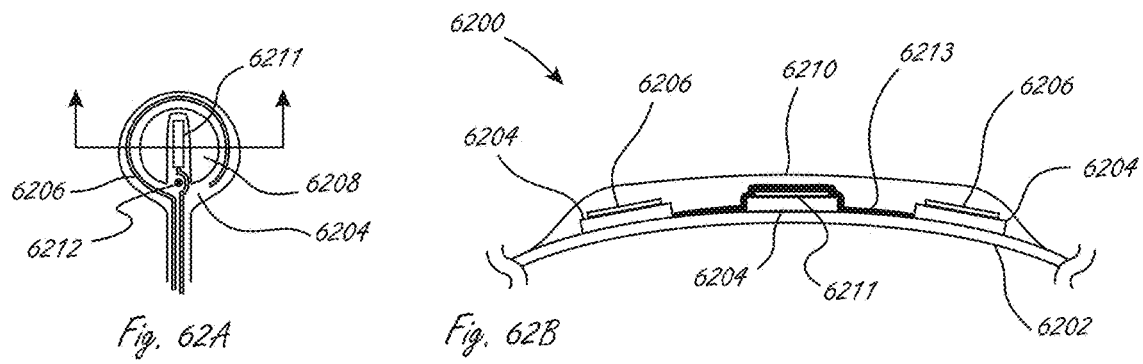
FIGS. 62A-62C illustrate an exemplary embodiment in which an expandable member includes an electrophoretic ink for electrode identification.
Figure 62C:
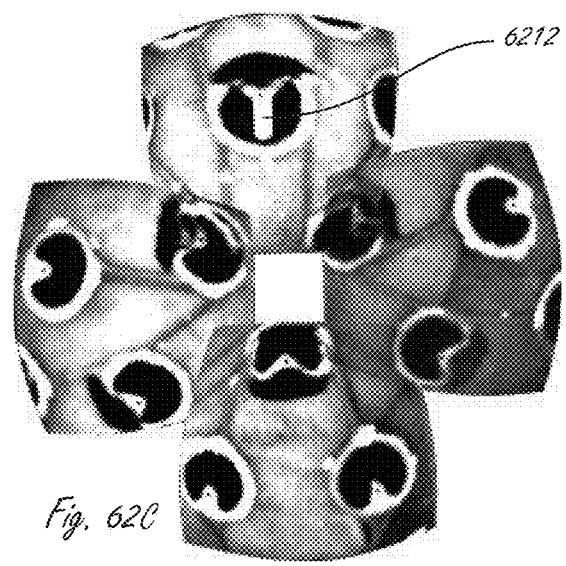

The disclosure above describes some exemplary devices and methods for identifying a particular electrode via markings, shapes, or thermochromic inks. Such markings help the user identify which electrodes to activate during an ablation. Using the markings previously described there is the possibility of misidentifying an electrode and only becoming aware of the fact after the burn is complete for non-active markers or during the burn for active markers such as thermochromic ink. In an alternate embodiment to that described in FIG. 46, the black paint (or other reflection adjuster) is replaced by an electronic or electrophoretic ink such as those described and manufactured by E Ink Corporation of Billerica, Mass. 01821 USA. As is known in the art, electrophoretic inks are inks which change their reflective and or absorptive properties as a function of the reorganization of components comprised within the ink brought about by the application of a charge across the ink. One such embodiment is illustrated in FIGS. 62A-C. As illustrated in FIG. 62A an additional transparent conductor pad 6211 has been added to a transparent flex circuit 6204 comprising an irrigation hole 6212. The transparent conductor may be comprised of materials such as indium tin oxide, or other transparent conductive oxides, conductive polymers, metal grids, and carbon nanotube, or graphene and nanowire, or other suitable transparent electrode material. The transparent conductor pad may be fed by a standard metal trace. FIG. 62B represents a cross section A-A of the elastomeric electrode flex circuit assembly of FIG. 62A, which is carried by the outer surface of balloon 6202. The flex circuit also comprises an irrigation hole 6212 which will be adjacent to holes in underlining balloon 6202 and the elastomeric electrode within which the flex circuit is comprised. In the flex circuit elastomeric electrode assembly illustrated in FIG. 62B, the black ink has been replaced by an electrophoretic ink 6213. As illustrated in FIG. 62C, when a charge is applied across the electrophoretic ink by energizing the conductor 6211 and the elastomeric electrode 6210, the electrophoretic ink optical properties change, and the section of electrophoretic ink 6212 over the conductor 4711 becomes lighter, thus allowing the electrode to be identified with a small charge (less than applied for tissue ablation) applied. In an alternate embodiment, the charge may be applied by energizing the saline within the balloon and the elastomeric electrode (not shown), and no separate electrode for activation of the electrophoretic ink is required. In yet another alternate embodiment, the electrophoretic ink and associated transparent conductor may be disposed on the underside (i.e., radially within) of the flex circuit.

The invention claimed is:

1. An ablation catheter, comprising:
   an elongate shaft; and
   an inflatable ablation member, carried by a distal region of the elongate shaft, including
   a flexible circuit, including a conductor in electrical communication with an ablation electrode, disposed outside of and carried by an outer surface of an inflatable balloon, and
   an ultrasound receiver disposed within a periphery of the ablation electrode, carried by the outer surface of the inflatable balloon, and configured to sense at least one aspect of tissue ablation with the ablation electrode.

2. The ablation catheter of claim 1, wherein the ultrasound receiver is disposed under the ablation electrode.

3. The ablation catheter of claim 1, wherein the ablation electrode is an elastomeric electrode in electrical communication with, and configured for use in the operation of, the ultrasound receiver.

4. The ablation catheter of claim 1, wherein the flexible circuit comprises a substrate, and wherein the substrate comprises an ultrasound emitter.

5. The ablation catheter of claim 4, wherein the substrate comprises a piezoelectric material.

6. The ablation catheter of claim 1, further comprising a plurality of ultrasound emitters in a phased array configuration.

7. The ablation catheter of claim 1, further comprising an ultrasound emitter disposed within the periphery of the ablation electrode.

8. The ablation catheter of claim 7, wherein the ultrasound emitter is carried by the outer surface of the inflatable balloon.

9. The ablation catheter of claim 8, wherein the ultrasound emitter is disposed under the ablation electrode.

* * * * *